(12) United States Patent
Yashiro et al.

(10) Patent No.: US 10,765,588 B2
(45) Date of Patent: Sep. 8, 2020

(54) INFORMATION PROCESSING APPARATUS AND INFORMATION PROCESSING METHOD

(71) Applicants: SONY CORPORATION, Tokyo (JP); SONY MOBILE COMMUNICATIONS INC., Tokyo (JP)

(72) Inventors: Kumi Yashiro, Kanagawa (JP); Tetsuya Naruse, Kanagawa (JP); Junichi Kosaka, Tokyo (JP); Yasumasa Suzuki, Tokyo (JP); Hiroko Nishioka, Kanagawa (JP); Hitoshi Rikukawa, Kanagawa (JP); Kohei Takada, Tokyo (JP); Masahiko Suzuki, Kanagawa (JP)

(73) Assignees: SONY CORPORATION, Tokyo (JP); SONY MOBILE COMMUNICATIONS INC., Tokyo (JP)

( * ) Notice: Subject to any disclaimer, the term of this patent is extended or adjusted under 35 U.S.C. 154(b) by 0 days.

(21) Appl. No.: 16/315,019

(22) PCT Filed: Jun. 23, 2017

(86) PCT No.: PCT/JP2017/023239
§ 371 (c)(1),
(2) Date: Jan. 3, 2019

(87) PCT Pub. No.: WO2018/025531
PCT Pub. Date: Feb. 8, 2018

(65) Prior Publication Data
US 2019/0307632 A1    Oct. 10, 2019

(30) Foreign Application Priority Data

Aug. 5, 2016 (JP) .................................. 2016-154480

(51) Int. Cl.
*G08B 23/00* (2006.01)
*A61H 3/06* (2006.01)
(Continued)

(52) U.S. Cl.
CPC ............... *A61H 3/061* (2013.01); *A61H 3/06* (2013.01); *G06K 9/4609* (2013.01); *G06T 7/00* (2013.01);
(Continued)

(58) Field of Classification Search
CPC ........ A61H 3/061; A61H 3/06; G06K 9/4609; G06T 7/00; G08G 1/005; G09B 21/00; G10L 13/027
(Continued)

(56) References Cited

U.S. PATENT DOCUMENTS

2006/0087416 A1\* 4/2006 Kumabe ................. B60Q 1/50
340/435
2006/0183516 A1\* 8/2006 Ham .................... A61N 5/0616
455/575.3
(Continued)

FOREIGN PATENT DOCUMENTS

JP         08-066441        3/1996
JP         2006-251596      9/2006
(Continued)

OTHER PUBLICATIONS

International Preliminary Report on Patentability in PCT/JP2017/023239 dated Feb. 5, 2019.
(Continued)

*Primary Examiner* — Kerri L McNally
*Assistant Examiner* — Thang D Tran
(74) *Attorney, Agent, or Firm* — Chip Law Group

(57) ABSTRACT

There is provided a processing unit that includes a direction decision unit and a guide information generation unit. The
(Continued)

direction decision unit determines a direction in which a person who behaves without a sense of sight walks. The guide information generation unit generates guide information for the person who behaves without the sense of sight to walk in the determined direction. The present technology is applicable, for example, to a smartphone or the like used by the person who behaves without the sense of sight.

19 Claims, 45 Drawing Sheets

(51) Int. Cl.
G06K 9/46 (2006.01)
G08G 1/005 (2006.01)
G10L 13/027 (2013.01)
G06T 7/00 (2017.01)
G09B 21/00 (2006.01)

(52) U.S. Cl.
CPC ............ *G08G 1/005* (2013.01); *G09B 21/00* (2013.01); *G10L 13/027* (2013.01)

(58) Field of Classification Search
USPC ...................................... 340/573.1
See application file for complete search history.

(56) References Cited

U.S. PATENT DOCUMENTS

| | | | | |
|---|---|---|---|---|
| 2012/0062357 A1* | 3/2012 | Slamka | ................... | G01C 21/20 340/4.11 |
| 2012/0099012 A1* | 4/2012 | Ryu | ................... | H04N 5/23293 348/333.01 |
| 2012/0120237 A1* | 5/2012 | Trepess | ................... | H04N 5/144 348/143 |
| 2012/0237086 A1* | 9/2012 | Kourogi | ................... | G01C 21/20 382/103 |
| 2012/0245839 A1* | 9/2012 | Syed | ................... | G01C 25/005 701/408 |
| 2012/0327203 A1* | 12/2012 | Oh | ................... | A61H 3/061 348/62 |
| 2013/0039416 A1* | 2/2013 | Someya | ................... | H04N 19/597 375/240.12 |
| 2013/0051611 A1* | 2/2013 | Hicks | ................... | G06T 11/60 382/103 |
| 2013/0250078 A1* | 9/2013 | Levy | ................... | A61F 9/08 348/62 |
| 2013/0258078 A1* | 10/2013 | Huang | ................... | A61H 3/061 348/62 |
| 2013/0336407 A1* | 12/2013 | Chen | ................... | H04N 19/513 375/240.16 |
| 2015/0163408 A1* | 6/2015 | Laroia | ................... | H04N 5/247 348/208.1 |
| 2015/0324646 A1* | 11/2015 | Kimia | ................... | G06F 3/005 348/62 |
| 2015/0346779 A1* | 12/2015 | Chae | ................... | G06F 1/1677 715/773 |
| 2016/0086332 A1* | 3/2016 | Chen | ................... | G06T 7/75 345/419 |
| 2016/0127698 A1* | 5/2016 | Mali | ................... | G01S 7/521 348/62 |
| 2016/0169680 A1* | 6/2016 | Lee | ................... | G01C 21/20 702/151 |
| 2016/0335917 A1* | 11/2016 | Lydecker | ................... | G09B 21/008 |
| 2017/0026069 A1* | 1/2017 | Kim | ................... | H04B 1/3888 |
| 2017/0238509 A1* | 8/2017 | Dayal | ................... | A61H 3/061 |
| 2017/0249862 A1* | 8/2017 | Border | ................... | H04N 7/183 |
| 2017/0319426 A1* | 11/2017 | Dayal | ................... | G01C 21/3679 |
| 2017/0374280 A1* | 12/2017 | Chan | ................... | H04N 1/00183 |
| 2018/0017393 A1* | 1/2018 | Willson | ................... | G01C 21/20 |
| 2018/0185232 A1* | 7/2018 | Namdar | ................... | A61H 3/061 |

FOREIGN PATENT DOCUMENTS

| | | |
|---|---|---|
| JP | 2008-117206 | 5/2008 |
| JP | 2008177206 A | 7/2008 |
| JP | 2014-137752 | 7/2014 |
| JP | 2015-213620 | 12/2015 |
| JP | 2016-067855 | 5/2016 |

OTHER PUBLICATIONS

International Search Report and Written Opinion in PCT/JP2017/023239 dated Sep. 12, 2017.

* cited by examiner

FIG. 27
(1) MOVE RIGHT ABOVE VISUALLY IMPAIRED PERSON
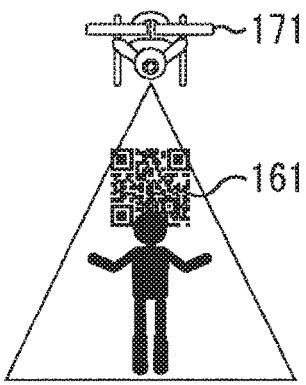
(2) IMAGE
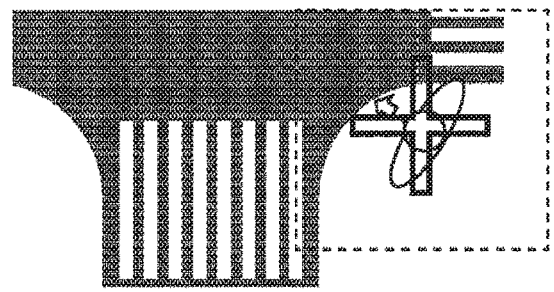
(3) DETECT DEVIATION FROM CORRECT POSITION AND INFORM OF IT
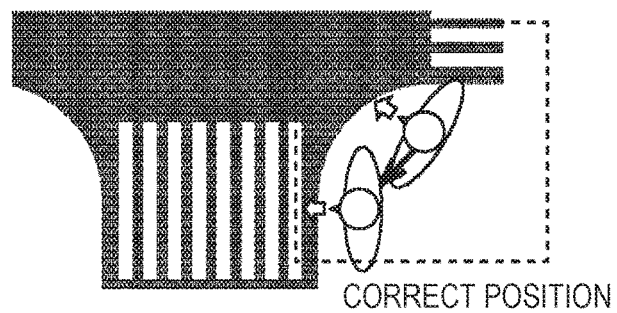
CORRECT POSITION

DETECT INFRARED LIGHT

DETECT INFRARED REFLECTOR

DETECT PERSON ACCORDING TO IMAGE RECOGNITION

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2017/023239 filed on Jun. 23, 2017, which claims priority benefit of Japanese Patent Application No. JP 2016-0154480 filed in the Japan Patent Office on Aug. 5, 2016. Each of the above-referenced applications is hereby incorporated herein by reference in its entirety.

TECHNICAL FIELD

The present technology relates to an information processing apparatus, an information processing method, and a program. In particular, the present technology relates to an information processing apparatus, an information processing method, and a program that allow those who behave without the sense of sight to safely walk in a correct direction.

BACKGROUND ART

The visually impaired, who behave without the sense of sight, use white canes and rely on Braille blocks or the like built on sidewalks to walk to destinations. A leading system that helps the visually impaired move to destinations has been developed (see, for example, Patent Literature 1).

CITATION LIST

Patent Literature

Patent Literature 1: JP H8-66441A

DISCLOSURE OF INVENTION

Technical Problem

However, it is difficult for the visually impaired to grasp a correct direction, for example, when they walk on a wide crosswalk having four lanes or more with no acoustic traffic lights or escort zones, or a wide and flat road with no Braille blocks. Accordingly, the visually impaired feel anxiety because they do not know whether they are walking in a correct direction. There has been nothing that can remove such anxiety.

The present technology has been devised in view of such a circumstance, and allows those who behave without the sense of sight to safely walk in a correct direction.

Solution to Problem

An information processing apparatus according to an aspect of the present technology includes: a direction decision unit configured to decide a direction in which a person who behaves without a sense of sight walks; and a first guide information generation unit configured to generate guide information for the person who behaves without the sense of sight to walk in the decided direction.

An information processing method according to an aspect of the present technology includes, by an information processing apparatus: a step of deciding a direction in which a person who behaves without a sense of sight walks; and a step of generating guide information for the person who behaves without the sense of sight to walk in the decided direction.

A program according to an aspect of the present technology causes a computer to function as: a direction decision unit configured to decide a direction in which a person who behaves without a sense of sight walks; and a guide information generation unit configured to generate guide information for the person who behaves without the sense of sight to walk in the decided direction.

According to an aspect of the present technology, a direction in which a person who behaves without the sense of sight walks is decided, and guide information for the person who behaves without the sense of sight to walk in the decided direction is generated.

Note that the program may be transmitted via a transmission medium and provided or may be recorded in a recording medium and provided.

Moreover, the information processing apparatus may be an independent apparatus or an internal block that constitutes a single apparatus.

Advantageous Effects of Invention

According to an aspect of the present technology, those who behave without the sense of sight can safely walk in a correct direction.

Note that the advantageous effects described here are not necessarily limited and may be any of the advantageous effects described in the present disclosure.

BRIEF DESCRIPTION OF DRAWINGS

FIG. 27 is a diagram describing an overview of a second visually impaired person walking support system.

MODE(S) FOR CARRYING OUT THE INVENTION

The following describes an example for implementing the present technology (which will be referred to as embodiment below). Note that description will be made in the following order.
1. First Visually Impaired Person Walking Support System
1.1 Overview of First Visually Impaired Person Walking Support System
1.2 Configuration Example of Information Processing Apparatus
1.3 Basic Principle of Crossing Direction Decision Process
1.4 Use Example in Which Smartphone Is Used
1.5 Functional Block Diagram of Processing Unit
1.6 Ref Image Registration Process
1.7 Crosswalk Guide Process
1.8 Modification of Ref Image Registration Process and Crosswalk Guide Process
2. Entire Route Guide Function
2.1 Overview of Entire Route Guide Function
2.2 Configuration Example of Information Processing Apparatus
2.3 Functional Block Diagram of Processing Unit
2.4 Voice Registration Process
2.5 Checkpoint Guide Reproduction Process
3. Second Visually Impaired Person Walking Support System
3.1 Overview of Second Visually Impaired Person Walking Support System
3.2 Configuration Example of Second Visually Impaired Person Walking Support System
3.3 Functional Block Diagram of Processing Unit
3.4 Image Transmission Process of Drone at Time of Registration Mode
3.5 Image Reception Process of Information Processing Apparatus at Time of Registration Mode
3.6 Image Transmission Process of Drone at Time of Guide Mode
3.7 Image Reception Process of Information Processing Apparatus at Time of Guide Mode
3.8 Modification of Second Visually Impaired Person Walking Support System
4. Smartphone Cover
4.1 External Appearance Example of Smartphone Cover
4.2 Block Diagram
4.3 Cover Close Detection Process
4.4 Cover Open Detection Process
4.5 Registration App Execution Operation Detection Process
4.6 Another Example of Registration App Execution Operation Detection Process
4.7 Another Example of Seal Pasted to Small Window
4.8 Another Example of UI App Disposition Allocated to Small Window
5. Hardware Configuration Example of Information Processing Apparatus <1. First Visually Impaired Person Walking Support System>

<1.1 Overview of First Visually Impaired Person Walking Support System>

First, with reference to FIGS. 1A and 1B, the overview of a first visually impaired person walking support system according to the present disclosure will be described.

The first visually impaired person walking support system according to the present disclosure includes at least two types of walking support processes that help the visually impaired (those who behave without the sense of sight) walk on a crosswalk.

Figure 1B:
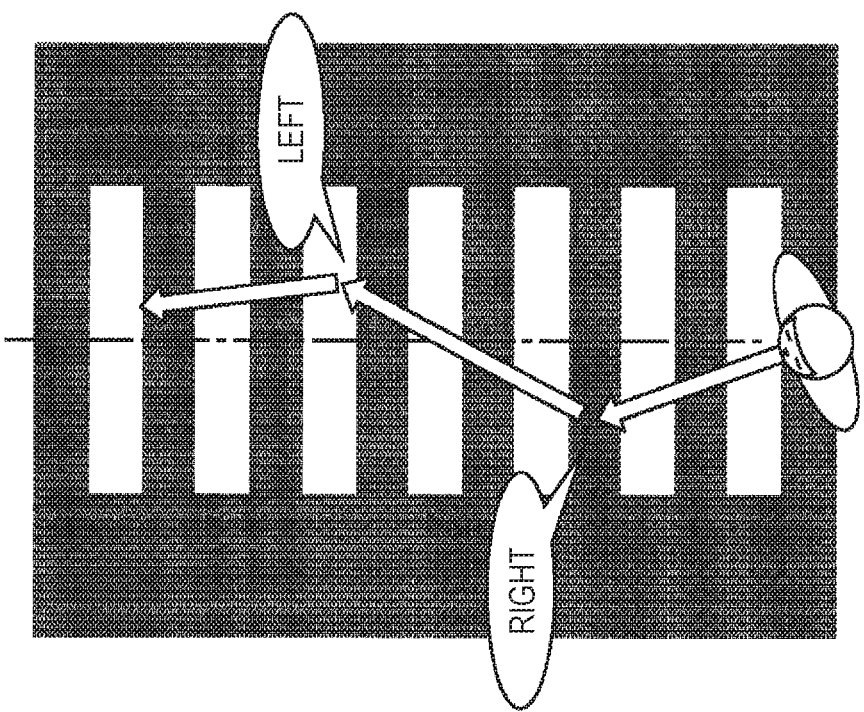
FIGS. 1A and 1B are diagrams describing an overview of a first visually impaired person walking support system according to the present disclosure.
Figure 1A:
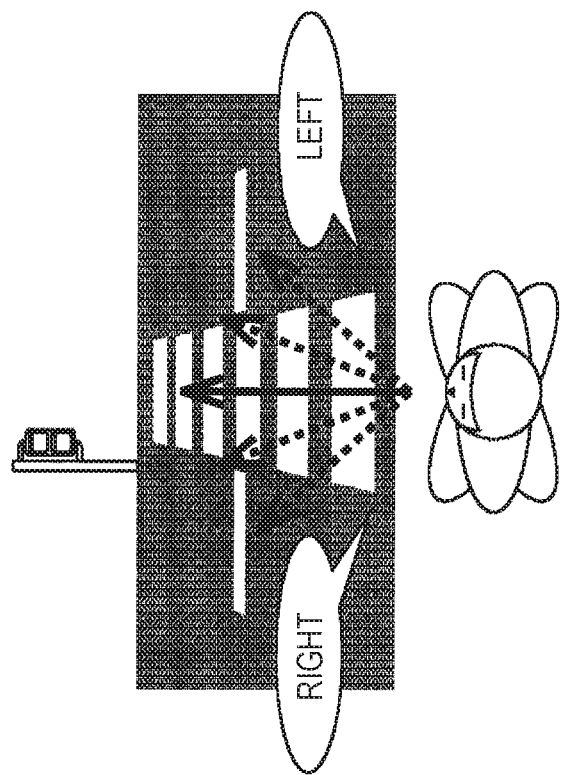

As illustrated in FIG. 1A, one of the walking support processes is a crossing direction decision process of deciding a walking direction such that, when a visually impaired person walks on a crosswalk, the visually impaired person faces in a correct crossing direction. The crossing direction decision process informs a visually impaired person, for example, like "right" and "left" at a position (which will be referred to as crossing point below) in front of a crosswalk on which the visually impaired person should walk to help the visually impaired person face in a correct crossing direction.

As illustrated in FIG. 1B, the other walking support process is a guide information generation process that generates guide information for a visually impaired person to walk in a correct crossing direction while the visually impaired person is walking on a crosswalk after the crossing direction decision process described above allows the visually impaired person to face in the correct crossing direction. The guide information generation process informs a visually impaired person, for example, like "right" and "left" to help the visually impaired person walk on a crosswalk without deviating from a correct crossing direction.

The following describes the details of the first visually impaired person walking support system according to the present disclosure.

<1.2 Configuration Example of Information Processing Apparatus>

Figure 2:
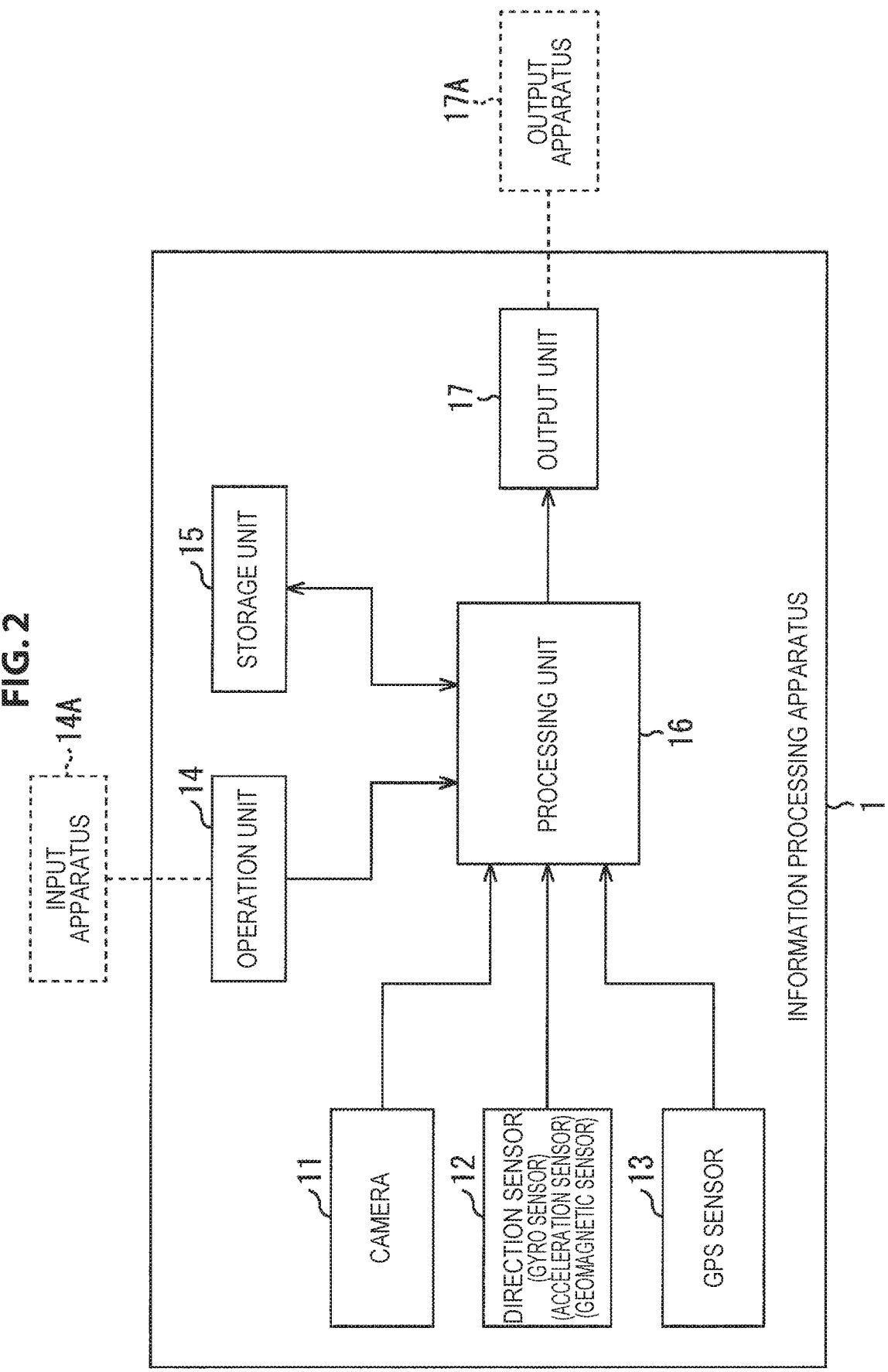
FIG. 2 is a block diagram illustrating a configuration example of an information processing apparatus that implements the first visually impaired person walking support system.

FIG. 2 is a block diagram illustrating a configuration example of an information processing apparatus that implements the first visually impaired person walking support system according to the present disclosure.

An information processing apparatus 1 in FIG. 2 can include, for example, a mobile terminal such as a smartphone, and includes a camera 11, a direction sensor 12, a global positioning system (GPS) sensor 13, an operation unit 14, a storage unit 15, a processing unit 16, and an output unit 17

The camera 11 includes, for example, an image sensor such as a complementary metal oxide semiconductor (CMOS) sensor or a charge coupled device (CCD), images an object such as a crosswalk, and supplies a resultant image to the processing unit 16.

The direction sensor 12 is a sensor that detects the direction in which the information processing apparatus 1 faces and the direction in which the information processing apparatus 1 moves, and supplies a detection result to the processing unit 16. The direction sensor 12 includes, for example, one or two or more of a gyro sensor (angular velocity sensor), an acceleration sensor, an inertia sensor, a geomagnetic sensor, and the like. A direction that can be detected by the direction sensor 12 may be an absolute direction like a geomagnetic sensor or a relative direction based on a predetermined direction.

The GPS sensor 13 sequentially acquires latitude and longitude data indicating the position of the GPS sensor 13 at fixed time intervals (e.g., interval of fifteen seconds), and supplies the acquired data to the processing unit 16.

The operation unit 14 includes, for example, an operation button, a touch sensor and the like, detects an operation of a user, and supplies an operation signal corresponding to the detected operation to the processing unit 16. Note that the operation unit 14 can also operate, for example, in cooperation with a short-range wireless communication function for Bluetooth (registered trademark) or the like, and an external input apparatus 14A including a wristband remote controller and the like including an operation button through short-range wireless communication.

The storage unit 15 includes, for example, a hard disk drive (HDD), a semiconductor memory and the like, and stores a program to be executed in the processing unit 16 and various kinds of data necessary to allow each component such as the camera 11 or the direction sensor 12 to operate. In addition, the storage unit 15 also stores an image or the like captured by the camera 11.

The processing unit 16 includes, for example, a central processing unit (CPU), a micro processing unit (MPU) and the like, and executes a predetermined program read out from the storage unit 15 to execute the crossing direction decision process and the guide information generation process described above.

The output unit 17 outputs an image, sound, force (vibration and motion), and the like on the basis of control from the processing unit 16. The output unit 17 includes, for example, an image output unit such as a liquid crystal display (LCD) or an organic electro-luminescence (EL) display, an audio output unit such as a speaker, a haptics output unit that outputs force, vibration, motion and the like, and the like.

Note that the output unit 17 can also operate in cooperation with a short-range wireless communication function for Bluetooth (registered trademark) or the like, and an external output apparatus 17A including an earphone, a headset, or the like including an operation button through short-range wireless communication.

<1.3 Basic Principle of Crossing Direction Decision Process>

Figure 3:
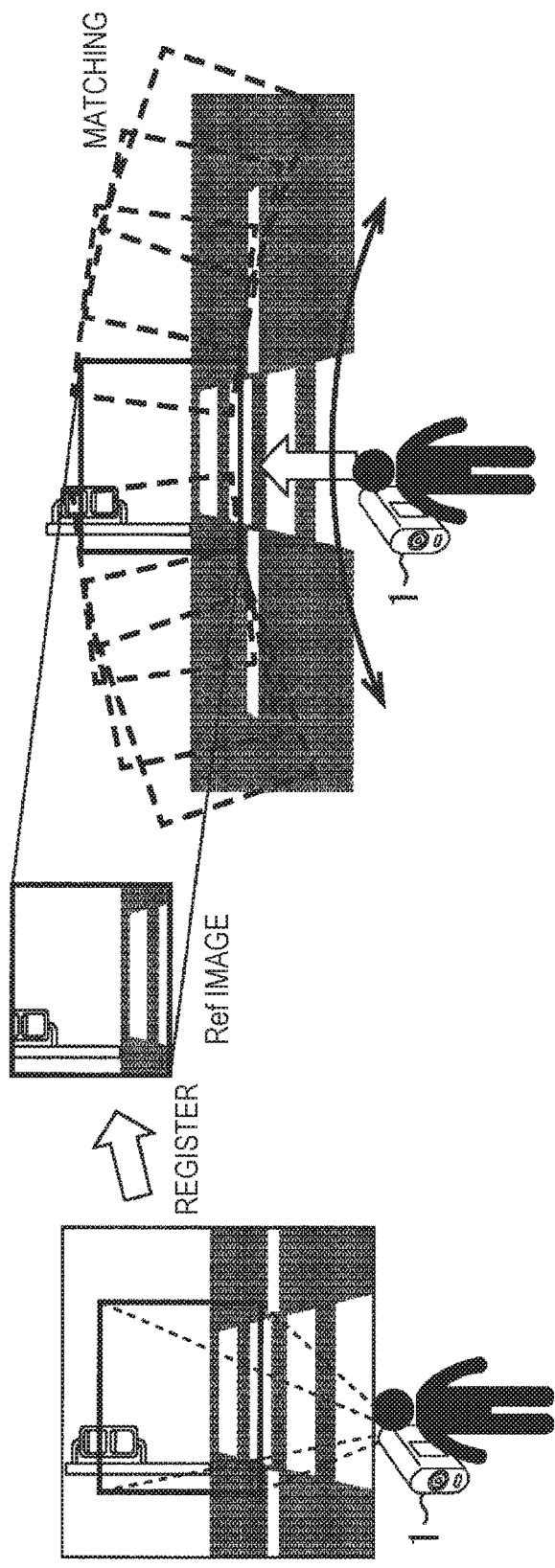
FIG. 3 is a diagram describing a basic principle of a crossing direction decision process that is performed by the information processing apparatus.

With respect to FIG. 3, a basic principle of a crossing direction decision process that is performed by the information processing apparatus 1 will be described.

When a visually impaired person walks on a moving route from a departure point to a predetermined destination, the visually impaired person first walks with an accompanying protector, captures a still image in a correct direction in which the visually impaired person wishes to walk on each crosswalk present on the moving route, and registers the captured still image in the information processing apparatus 1. The information processing apparatus 1 stores positional information of the imaging point acquired by the GPS sensor 13 along with the captured still image. The still image stored in the information processing apparatus 1 serves as a reference image (which will be referred to as Ref image below) that is to be referred to at the time of the second movement or later. The accompanying protector is a sighted person, so that the accompanying protector can check whether the Ref image is an image showing a correct direction of a crosswalk.

Then, when the visually impaired person walks alone from the departure point to the predetermined destination for the second time or later, the information processing apparatus 1 guides, at each crosswalk present on the moving route, the visually impaired person in a correct direction of a crossing direction in which the visually impaired person should walk on the basis of the Ref image. Specifically, the information processing apparatus 1 performs a process of matching a still image (which will be referred to as current image below) captured while a visually impaired person is walking and with a Ref image to decide a correct direction of a crossing direction in which the visually impaired person should walk and guide the visually impaired person.

After a correct direction of a crossing direction in which a visually impaired person should walk is decided according to the crossing direction decision process described above, guide information for the time when a visually impaired person is walking on the crosswalk is generated with the correct crossing direction set as a reference direction in the next guide information generation process, and the visually impaired person is notified.

<1.4 Use Example in Which Smartphone Is Used>

Figure 4:
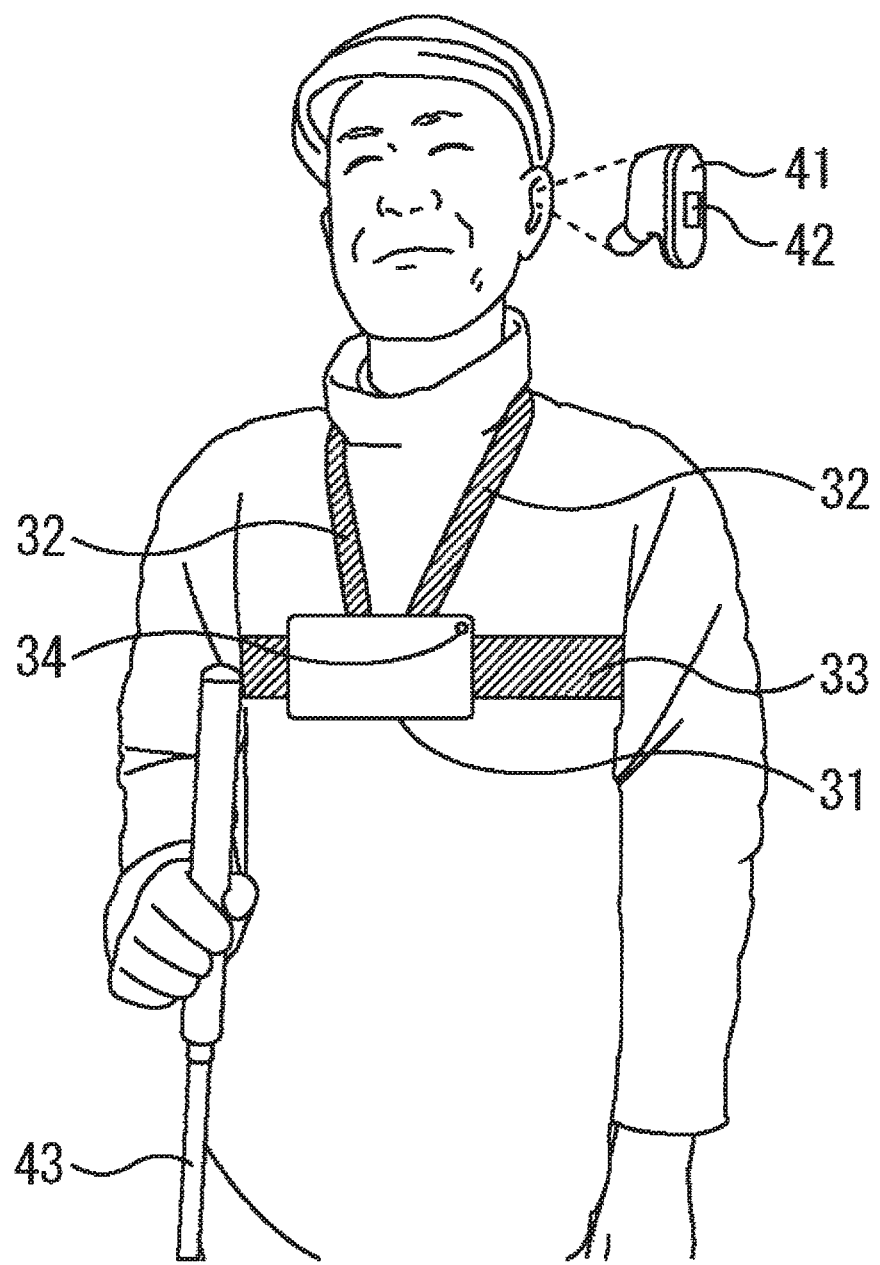
FIG. 4 is a diagram illustrating a use example of the first visually impaired person walking support system by a visually impaired person.

FIG. 4 illustrates a use example of the first visually impaired person walking support system by a visually impaired person in the case where a smartphone is used as the information processing apparatus 1.

A smartphone 31 serving as the information processing apparatus 1 is worn by a visually impaired person with a neck strap 32 and a chest strap 33. The smartphone 31 is disposed to face the imaging direction of the camera 34 in the advancing direction.

A visually impaired person wears a wireless earphone 41 on an ear. The wireless earphone 41 serves as the input apparatus 14A and the output apparatus 17A. The wireless earphone 41 receives an audio signal from the smartphone 31, for example, through short-range wireless communication such as Bluetooth (registered trademark), and outputs the received audio signal as sound. In the present embodiment, voice announcements like "right" and "left" are output.

In addition, the wireless earphone 41 includes an operation button 42, detects a visually impaired person depressing the operation button 42, and supplies the depressing operation signal to the smartphone 31. A visually impaired person can have a white cane 43 with the right hand, and operate the operation button 42 of the wireless earphone 41 with the left hand.

<1.5 Functional Block Diagram of Processing Unit>

Figure 5:
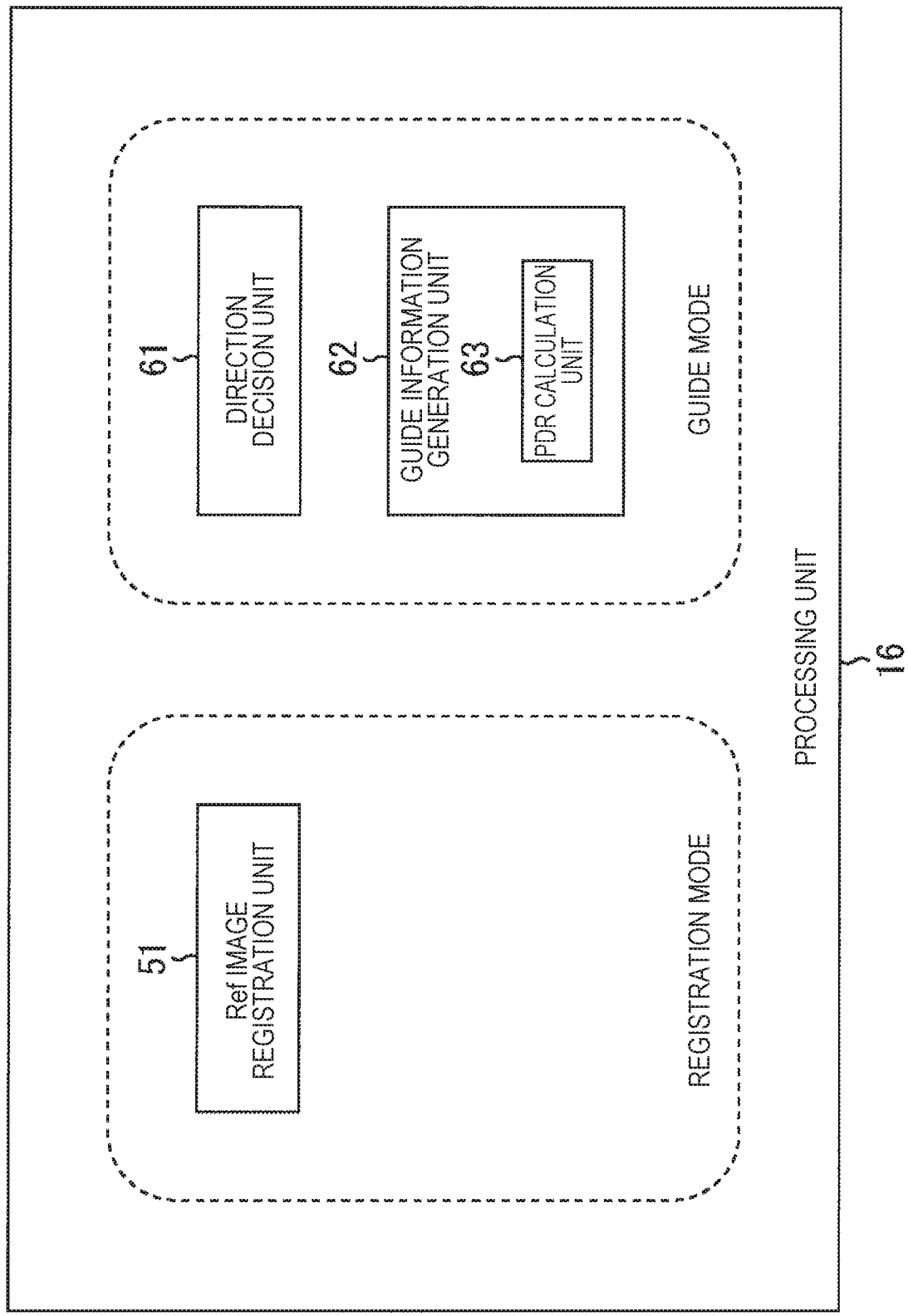
FIG. 5 is a functional block diagram of a processing unit in the first visually impaired person walking support system.

FIG. 5 is a functional block diagram of the processing unit 16 of the information processing apparatus 1.

To execute the crossing direction decision process and the guide information generation process, the processing unit 16 includes the two operation modes of a registration mode and a guide mode.

The registration mode is an operation mode executed when a Ref image is registered in walking for the first time. The processing unit 16 includes a Ref image registration unit 51 as an execution module executed at the time of the registration mode. The Ref image registration unit 51 acquires a Ref image captured by the camera 11 according to an operation of an accompanying protector, and registers the acquired Ref image in the storage unit 15.

Meanwhile, the guide mode is an operation mode executed when walking for the second time or later. The processing unit 16 includes a direction decision unit 61 and a guide information generation unit 62 as execution modules executed at the time of the guide mode.

Before a visually impaired person walks on a crosswalk, the direction decision unit 61 decides a correct crossing direction on the basis of a Ref image registered when the visually impaired person walks for the first time.

The guide information generation unit 62 generates guide information for a visually impaired person and outputs the guide information such that the visually impaired person does not deviate from a correct direction while the visually impaired person is walking on a crosswalk. More specifically, the guide information generation unit 62 sets a crossing direction decided by the direction decision unit 61 as a reference direction, calculates the amount of deviation from the reference direction while a visually impaired person is walking on a crosswalk, generates guide information on the basis of the calculated amount of deviation, and notifies the visually impaired person. The guide information generation unit 62 includes a PDR calculation unit 63 that uses a sensor signal output by the direction sensor 12 to calculate a relative position from a reference position (crossing point) in front of a crosswalk on the basis of pedestrian dead reckoning (PDR).

In the case where the processing unit 16 is implemented by an arithmetic processing apparatus such as a CPU executing a predetermined program, the entire processing unit 16 may be configured as one application program (which will be referred to simply as app below), or the registration mode and the guide mode may be separately configured as different apps. Alternatively, the Ref image registration unit 51, the direction decision unit 61, and the guide information generation unit 62 may also be configured separately as different apps.

In the present embodiment, description will be made with the registration mode and the guide mode configured separately as different apps. For example, when an operation of operating a touch panel display serving as the operation unit 14 to execute a registration app is performed, the Ref image registration unit 51 is started. When an operation of executing a guide app is performed, the direction decision unit 61 and the guide information generation unit 62 are started.

<1.6 Ref Image Registration Process>

Figure 6:
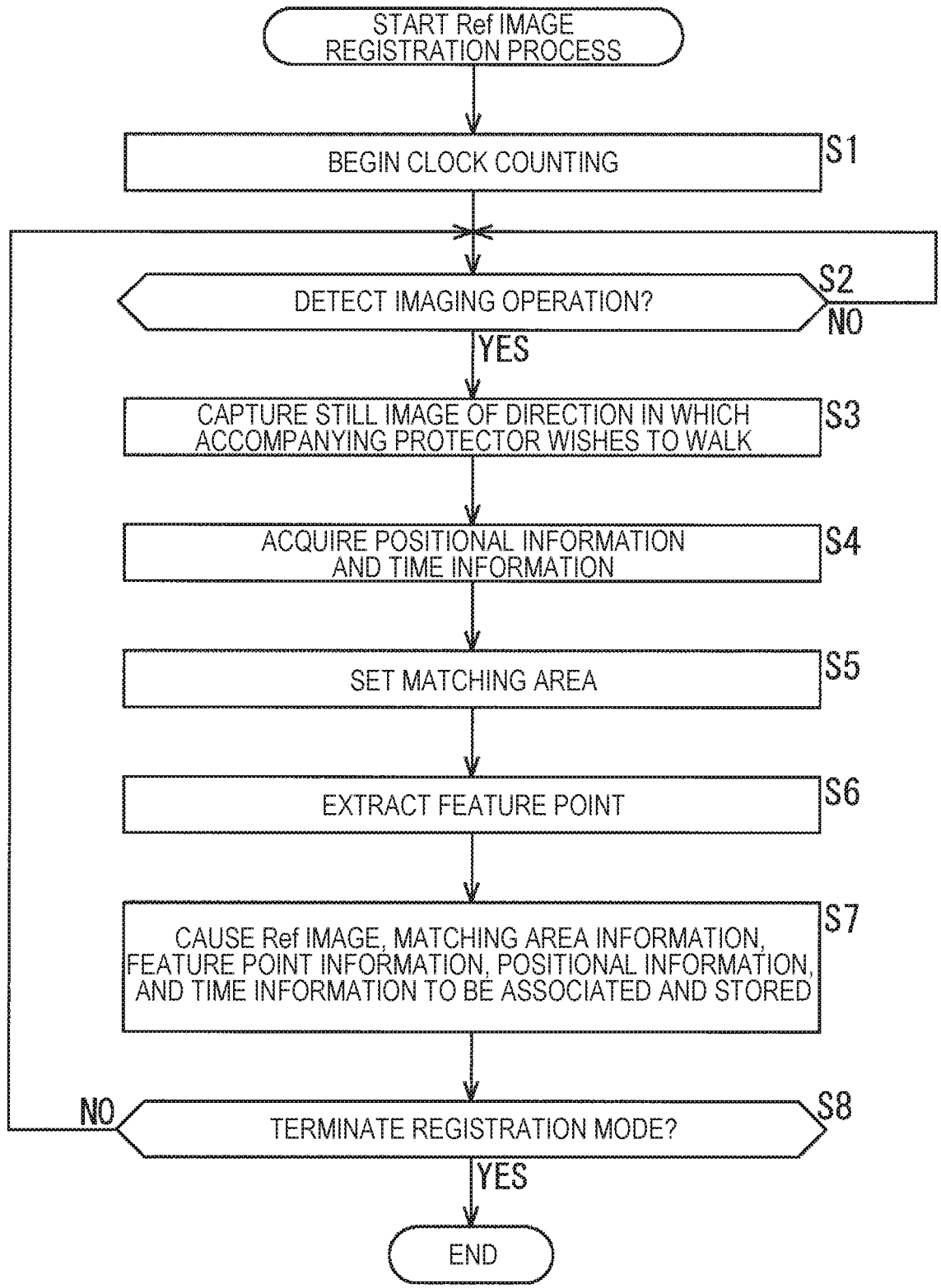
FIG. 6 is a flow chart describing a Ref image registration process.

Next, with reference to the flow chart of FIG. 6, a Ref image registration process executed by the Ref image registration unit 51 in the registration mode will be described. This process is begun, for example, when a registration app is executed at the timing at which a visually impaired person begins to move from a departure point to a predetermined destination with an accompanying protector.

First, in step S1, the Ref image registration unit 51 begins clock counting for measuring the elapsed time (necessary time) from the departure point.

The visually impaired person walks on a moving route to the predetermined destination with the accompanying protector. When the accompanying protector arrives at a crosswalk present on the moving route, the accompanying protector performs, on the information processing apparatus 1, an operation of capturing a still image in a correct direction in which the accompanying protector wishes to walk.

In step S2, the Ref image registration unit 51 determines whether an imaging operation by the accompanying protector is detected, and repeats the process of step S2 until it is determined that an imaging operation is detected.

Then, in the case where it is determined in step S2 that an imaging operation is detected, the process proceeds to step S3, and the Ref image registration unit 51 controls the camera 11 to cause the camera 11 to perform imaging. The camera 11 captures a still image in a direction in which the accompanying protector wishes to walk in accordance with the control of the Ref image registration unit 51. The still image obtained by performing imaging is supplied to the Ref image registration unit 51 as a Ref image.

Next, in step S4, the Ref image registration unit 51 acquires current positional information and time information. That is, the Ref image registration unit 51 acquires positional information that is supplied from the GPS sensor 13 and indicates the current latitude and longitude, and the elapsed time from the counting begun in step S1 as current positional information and time information.

In step S5, the Ref image registration unit 51 sets a matching area that is an area in which a process of matching a Ref image supplied from the camera 11 with a current image captured at the time of the guide mode is performed.

In step S6, the Ref image registration unit 51 extracts a feature point of the image of the matching area set in the Ref image.

Figure 7:
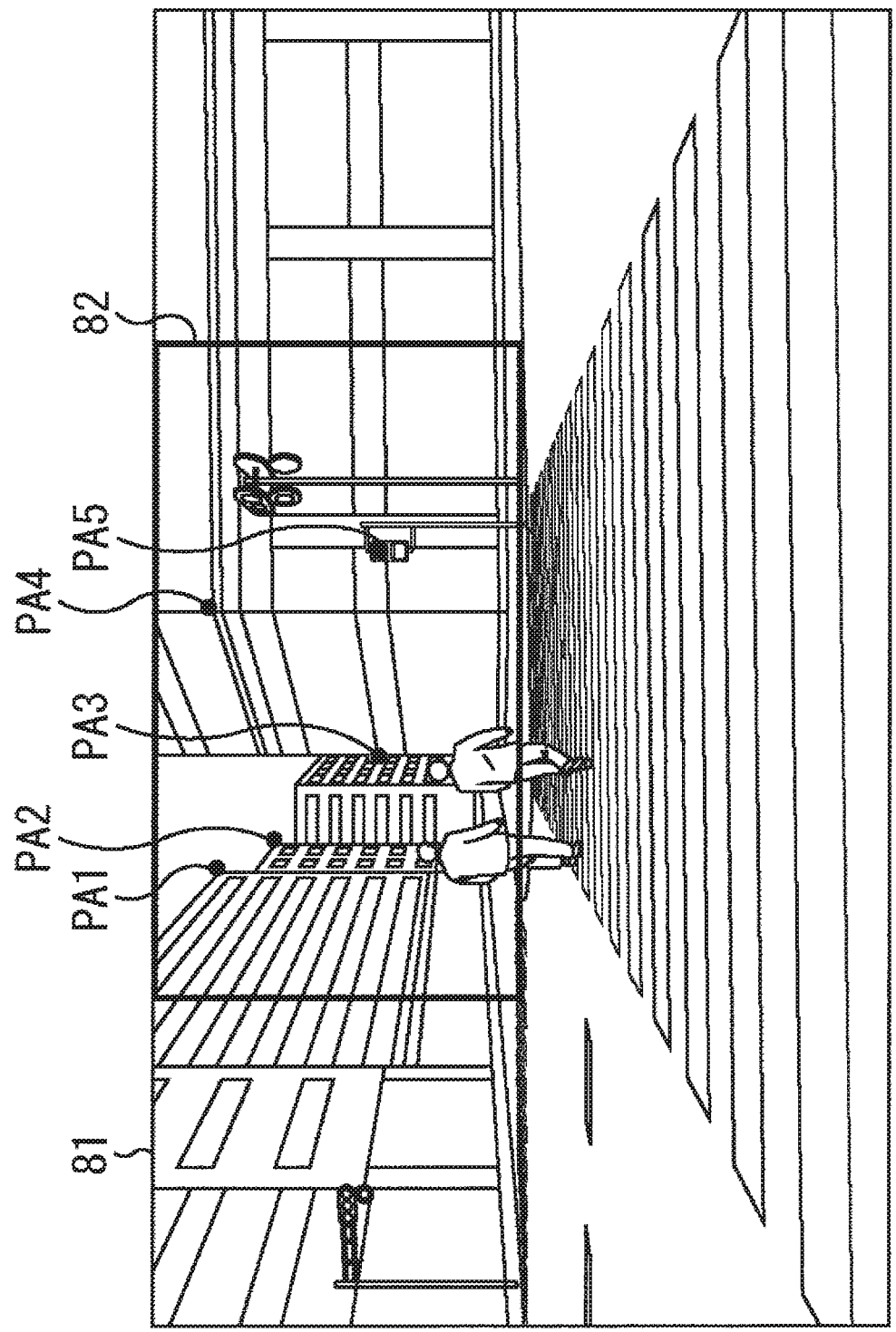
FIG. 7 is a diagram illustrating process examples of steps S5 and S6 in FIG. 6.

FIG. 7 is a diagram illustrating process examples of steps S5 and S6.

In FIG. 7, a matching area 82 is set in a Ref image 81 supplied from the camera 11. In addition, five feature points PA1 to PA5 extracted for the image of the matching area 82 are illustrated.

The matching area 82 may be automatically set by the Ref image registration unit 51 on the basis of a predetermined condition, or may also be set on the basis of an operation of an accompanying protector.

For example, in the case where the Ref image registration unit 51 automatically sets the matching area 82, for example, the lower half frequently shows a crosswalk. Accordingly, a predetermined position in the entire Ref image 81 is decided as the matching area 82 like the upper half area that is the central part having the half width of the entire Ref image 81 with respect to the horizontal direction or the like. Alternatively, a predetermined area may be decided as the matching area 82 on the basis of the position of a traffic light or a crosswalk included in the Ref image 81.

Meanwhile, in the case where the matching area 82 is set on the basis of an operation of an accompanying protector, for example, the Ref image registration unit 51 can superimpose a window that defines the matching area 82 on the Ref image 81, and ask the accompanying protector to operate the window for decision.

In addition, to extract a feature point for the image of the matching area 82, for example, an extraction algorithm such as AKAZE or ORB that uses a local feature amount can be adopted. A feature point extraction process is provided in Open Source Computer Vision Library (OpenCV). In an actual feature point extraction process, a large number of feature points are detected, but in the example of FIG. 7, only the five feature points PA1 to PA5 are illustrated for the sake of simplicity.

FIG. 6 will be referred to again. In step S7, the Ref image registration unit 51 associates the Ref image supplied from the camera 11 with matching area information, feature point information, positional information, and time information, and causes the storage unit 15 to store them. The matching area information is information indicating a matching area in a Ref image, and is, for example, the coordinates of the four corners of the matching area. The feature point information is information indicating the position of each feature point detected in a matching area. The positional information and the time information are information indicating the position and the time at which the Ref image acquired in step S4 is captured.

In step S8, the Ref image registration unit 51 determines whether to terminate the registration mode. For example, in the case where a visually impaired person and an accompanying protector arrive at a destination, it is determined with an operation of the accompanying protector to terminate a registration app that the registration mode is terminated.

In the case where it is determined in step S8 that the registration mode is not still terminated, the process returns to step S2, and the processes of steps S2 to S8 described above are repeated. When the accompanying protector arrives at a crosswalk (crossing point) present on a moving route, this causes a Ref image captured according to an operation of the accompanying protector to be stored in the storage unit 15 and also causes the position and the time at which the Ref image is captured and information regarding a matching area and a feature point of the Ref image to be stored in the storage unit 15.

In the case where it is determined in step S8 that the registration mode is terminated, the Ref image registration process terminates.

According to the Ref image registration process described above, a Ref image is stored in the storage unit 15 for each crossing point of a crosswalk present on a moving route from a departure point to a destination along with matching area information and feature point information, and positional information and time information of the Ref image.

<1.7 Crosswalk Guide Process>

Next, with reference to the flow chart of FIG. 8, a crosswalk guide process executed by the direction decision unit 61 and the guide information generation unit 62 in the guide mode will be described. This process is begun, for example, when the guide app is executed at the timing at which movement is begun at a departure point in the case where a visually impaired person walks alone on a moving route registered in the registration mode. The direction decision unit 61 and the guide information generation unit 62 can mutually exchange and execute necessary information at necessary timing.

First, in step S21, the direction decision unit 61 begins clock counting for measuring the elapsed time (necessary time) from the departure point.

In step S22, the direction decision unit 61 acquires current positional information from the GPS sensor 13, and determines, on the basis of the acquired current positional information and the elapsed time from the departure point, whether a crossing point whose Ref image is stored in the storage unit 15 is approached. More specifically, the direction decision unit 61 compares the positional information and the time information stored in association with a Ref image stored in the storage unit 15 with the current positional information and the elapsed time to determine whether a Ref image associated with a position within a predetermined range from the current positional information is registered in the storage unit 15. It depends on the positional accuracy of the GPS sensor 13, but, for example, when a visually impaired person arrives within a range of 50 to 100 m from a crossing point, it is determined that the crossing point is approached. A crossing point is basically found with positional information, and time information is referred to.

Until it is determined in step S22 that the crossing point is approached, the process of step S22 is repeated.

Then, in the case where it is determined in step S22 that the crossing point is approached, the process proceeds to step S23, the direction decision unit 61 causes the output unit 17 to output the voice message of, for example, "There is a crosswalk registered therearound," and notifies a visually impaired person that the registered crossing point is nearby.

In step S24, the direction decision unit 61 reads out a Ref image corresponding to the crossing point from the storage unit 15.

When the visually impaired person moves to a crosswalk, the visually impaired person depresses the operation button of the operation unit 14 or the operation button 42 of the wireless earphone 41.

In step S25, the direction decision unit 61 determines whether a button operation of the visually impaired person is detected, and waits until it is determined that a button operation is detected.

Then, in the case where it is determined in step S25 that a button operation is detected, the process proceeds to step S26, and the direction decision unit 61 executes a direction detection process. The direction decision process is a process of capturing a still image (current image) at the current position, extracting a feature point corresponding to a feature point of the Ref image from the captured current image, and detecting a direction on the basis of a matching result obtained by matching the corresponding feature points.

Figure 8:
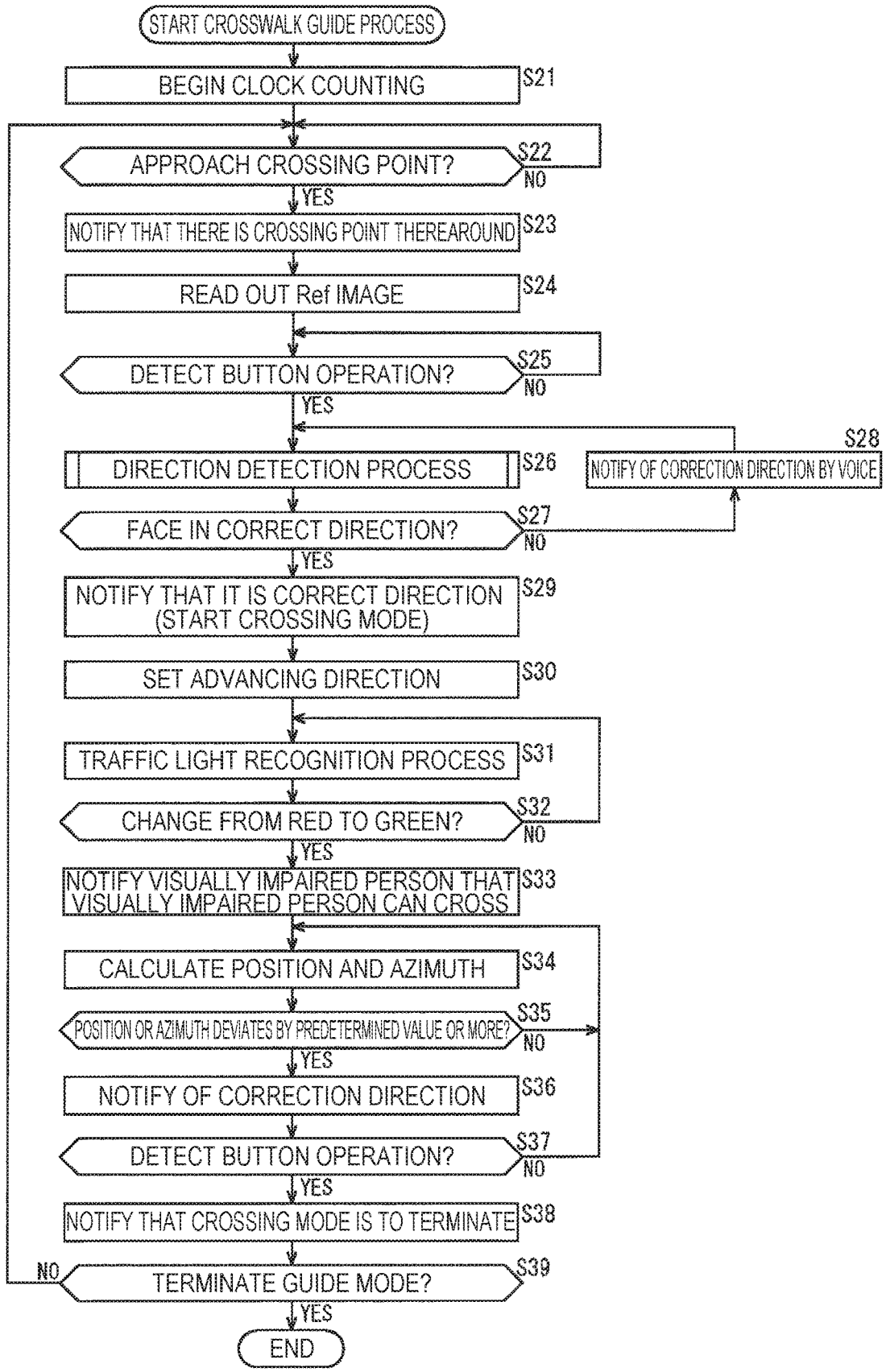
FIG. 8 is a flow chart describing a crosswalk guide process.
Figure 9:
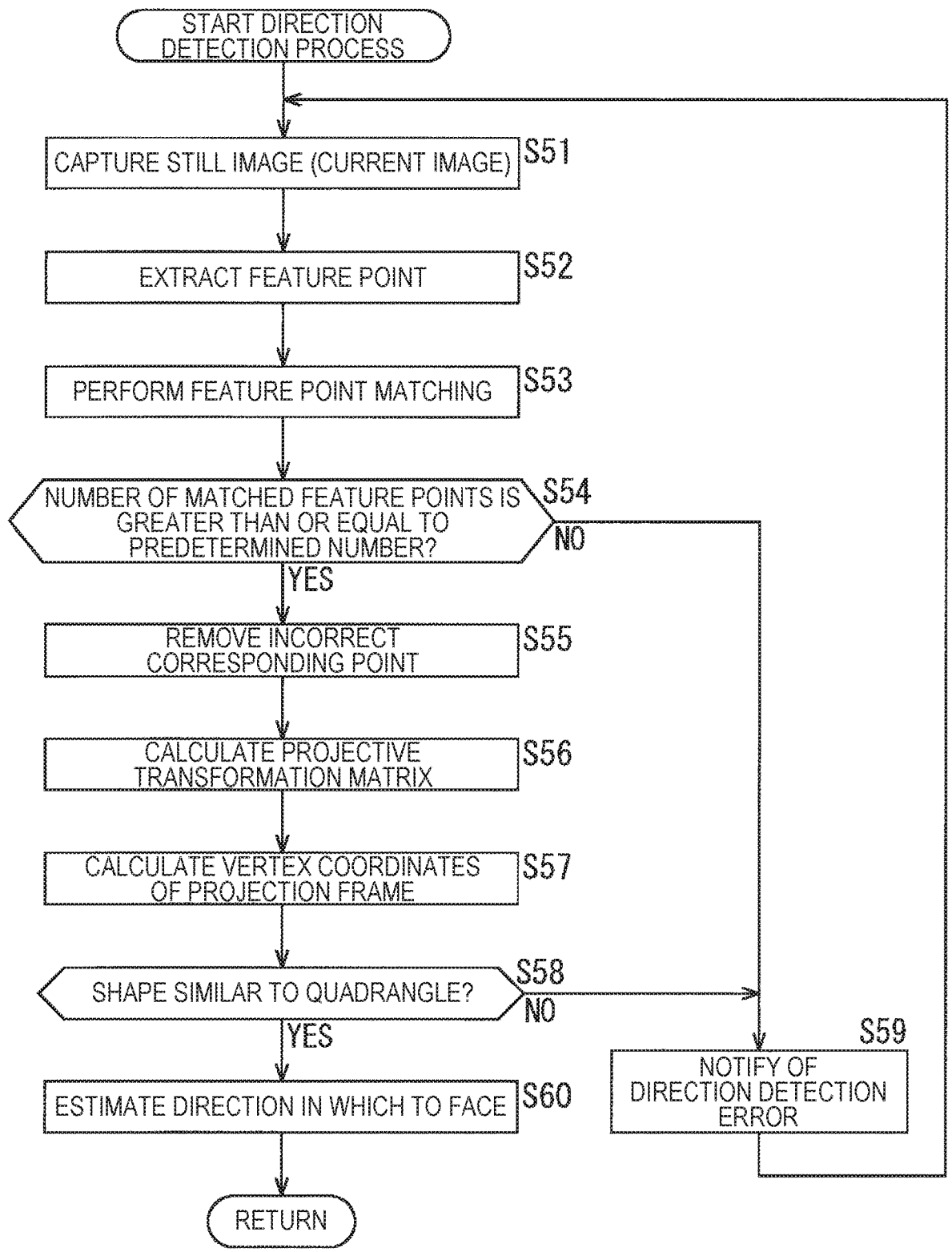
FIG. 9 is a detailed flow chart of a direction detection process of step S26 in FIG. 8.

FIG. 9 is a detailed flow chart of the direction detection process of step S26 in FIG. 8.

In the direction detection process, first, in step S51, the direction decision unit 61 controls the camera 11 and causes the camera 11 to capture a still image. The camera 11 captures a still image in accordance with the control of the direction decision unit 61. The still image captured in step S51 serves as a current image while moving.

In step S52, the direction decision unit 61 uses the same feature extraction algorithm as the feature extraction algorithm executed in the Ref image registration process for the current image obtained by performing imaging to extract a feature point.

In step S53, the direction decision unit 61 uses the feature point extracted for the current image and feature point information of the Ref image corresponding to the crossing point to perform feature point matching that detects the corresponding feature points. For example, a feature point having the shortest feature point distance such as Hamming distance to a feature point of a Ref image is detected as the corresponding feature point of the current image.

In step S54, the direction decision unit 61 determines whether the number of feature points matched in the current image is greater than or equal to a predetermined number.

In the case where it is determined in step S54 that the number of matched feature points is less than the predetermined number, it is determined that it is impossible to accurately determine a direction and the process proceeds to the error notification process of step S59 described below.

In contrast, in the case where it is determined in step S54 that the number of matched feature points is greater than or equal to the predetermined number, the process proceeds to step S55, and the direction decision unit 61 removes an incorrect corresponding point from the detected feature points. For example, feature points having motion vectors with constant distance or more to a mean vector obtained by averaging motion vectors connecting feature points of a Ref image to the corresponding feature points of a current image with respect to all the feature points of the current image are removed as incorrect corresponding points.

In step S56, the direction decision unit 61 uses a feature point after an incorrect corresponding point is removed, and calculates a projective transformation matrix for projectively transforming a Ref image into the current image. If there are four or more feature points, it is possible to calculate a projective transformation matrix. For feature points used to calculate a projective transformation matrix, the image portion of a traffic light (for pedestrians or vehicles) can be preferentially used. It is possible to sense a traffic light (for pedestrians or vehicles) day and night on the basis of luminance information, so that a robust projective estimation is possible. If one image shows four or more traffic lights, it is possible to calculate a projective transformation matrix with only the motion vectors of the traffic lights without using a feature point detected according to a local feature amount. Traffic lights are not limitative, but, for example, billboards, traffic signs, and the like may also be used.

In step S57, the direction decision unit 61 uses the obtained projective transformation matrix to transform matching area information of a Ref image, and calculates the vertex coordinates of the four corners of a projection frame obtained by projecting the matching area of the Ref image on the current image.

In step S58, the direction decision unit 61 calculates the inner products of the respective sides of the projection frame to determine whether the obtained projection frame has a shape similar to a quadrangle.

In the case where it is determined in step S58 that the projection frame does not have a shape similar to a quadrangle, the process proceeds to step S59, and the direction decision unit 61 determines that it is not possible to accurately determine a direction, causes the output unit 17 to output the voice message of, for example, "It is not possible to detect a direction" or the like and notifies a visually impaired person of a direction detection error.

After step S59, the process returns to step S51, and the processes of steps S51 to S58 described above are repeated. Thus, in the case where it is not possible to detect a direction, a still image is captured again.

In contrast, in the case where it is determined in step S58 that the projection frame has a shape similar to a quadrangle, the process proceeds to step S60, and the direction decision unit 61 uses a captured current image to estimate the direction in which a visually impaired person faces.

Figure 10:
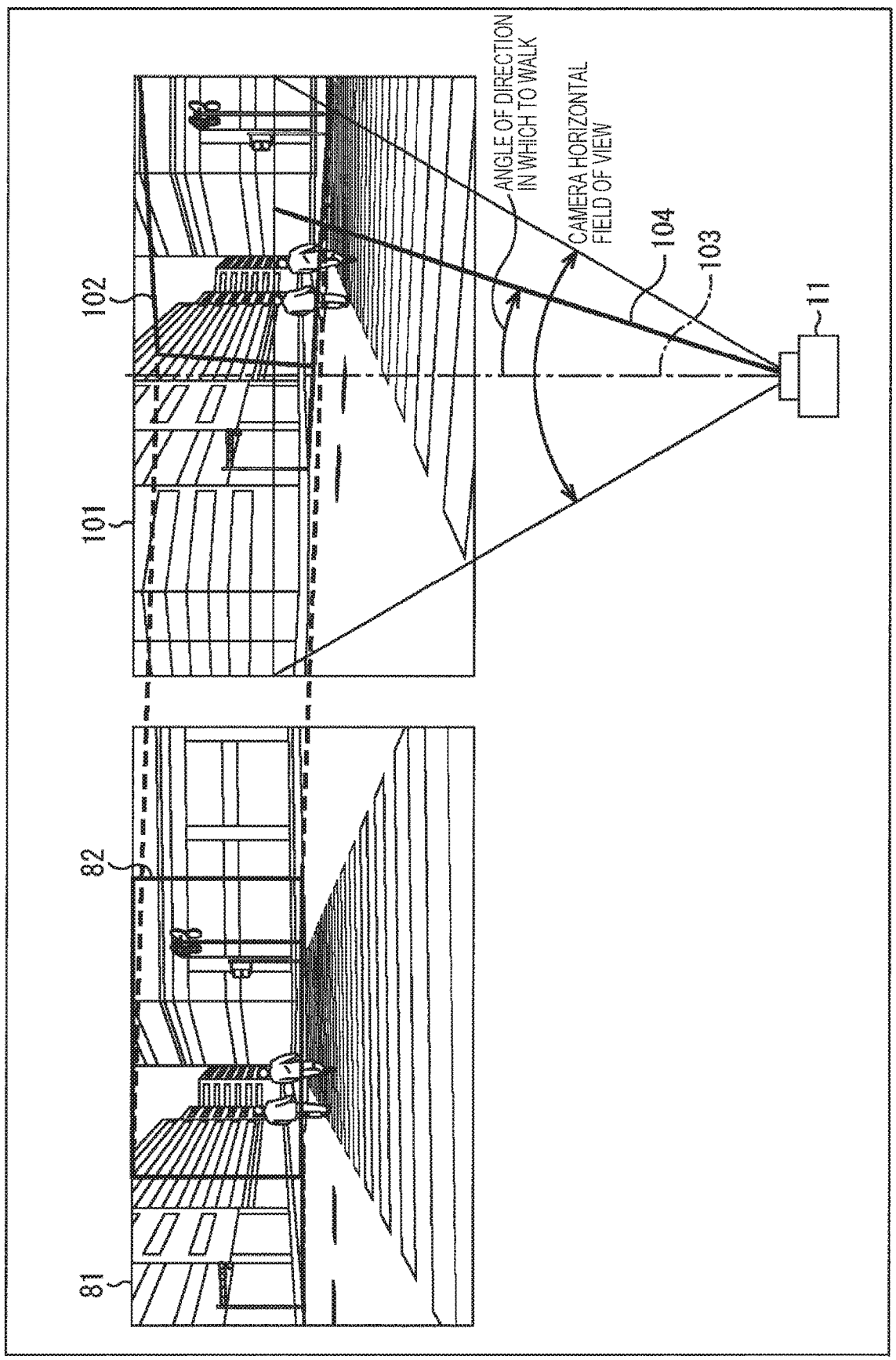
FIG. 10 is a diagram illustrating a process example of step S60.

FIG. 10 illustrates an example of a process of estimating the direction in which a visually impaired person faces, which is executed in step S60.

A current image 101 is captured, and a feature point is extracted. The extracted feature point is matched with a feature point of the Ref image 81 corresponding to the current position to calculate a projection frame 102 for the current image 101.

A central direction 104 of the projection frame 102 is estimated as a direction in which a visually impaired person should walk. It is possible to calculate an angle for each pixel on the basis of the relationship between the field-of-view range and the number of pixels of the camera 11, so that the direction in which a visually impaired person should walk can be calculated as the angle between an imaging center 103 of the camera 11 worn by the visually impaired person and the central direction 104 of the projection frame 102 which is based on the number of pixels in the horizontal direction. To more accurately calculate an angle, the direction in which a visually impaired person should walk may be estimated by taking even calibration information such as the lens distortion of the camera into consideration.

Once the process of step S60 to estimate a direction in which a visually impaired person faces terminates, the direction detection process of step S26 in FIG. 9 terminates. With reference to FIG. 8 again, the process proceeds to step S27.

In step S27 of FIG. 8, the direction decision unit 61 determines, on the basis of a result estimated in the direction detection process, whether the visually impaired person faces in a correct direction. For example, in the case where an angle estimated in the direction detection process falls within a predetermined range, it is determined that the visually impaired person faces in a correct direction.

In the case where it is determined in step S27 that the visually impaired person does not face in a correct direction, the process proceeds to step S28, and the direction decision unit 61 causes the output unit 17 to output the voice message of, for example, "right, right, right a little bit more, . . . " or "left, left, left a little bit more, . . . ," and notifies the visually impaired person of a correction direction by voice.

After step S28, the process returns to step S26, and the direction detection process is executed again. Thus, a new current image is captured again with respect to the direction in which the orientation of the body of the visually impaired person is changed in accordance with the voice message, and the direction in which the visually impaired person faces is detected.

Current images can be captured at intervals, for example, approximately one image every second. However, it is difficult to output the voice message of "left, left, . . . " whenever a current image is captured. Therefore, the direction decision unit 61 can cause the voice message of "left" or "right" to be output once for some current images. At the same time as the voice message, in the case where a visually impaired person faces in a correct direction, a high-toned electronic sound like "beep, beep, beep," can be output. In the case where a visually impaired person faces in a different direction, a low-toned electronic sound like "chug, chug, chug," can be output.

In the case where it is determined in step S27 that the visually impaired person faces in a correct direction, the process proceeds to step S29, and the direction decision unit 61 causes the output unit 17 to output the voice message of "It is a correct direction" along with the electronic sound of, for example, "ding ding" and notifies the visually impaired person that it is a correct direction. In addition, in step S29, the direction decision unit 61 issues, by voice via the output unit 17, a notification that the process of deciding a correct crossing direction terminates, and a crossing mode for guidance about a deviation caused while walking on a crosswalk begins.

In step S30, the guide information generation unit 62 regards, as the advancing direction of the visually impaired person, the central direction 104 of the projection frame 102 of the last current image in which the visually impaired person is determined to face in a correct direction in the direction detection processes of step S26 which are repeatedly executed once or more, and sets the advancing direction of the crossing direction for the PDR calculation unit 63. That is, the actual orientation of the body of the visually impaired person is not strictly the same as a correct crossing direction of the Ref image. Accordingly, the guide information generation unit 62 sets a correct advancing direction on the basis of not the direction in which the visually impaired person actually faces, but the Ref image. In the PDR calculation unit 63, the direction sensor 12 uses a sensor signal to be output to initialize a position and a direction for calculating a relative position from a crossing point.

In step S31, the guide information generation unit 62 causes the camera 11 to perform imaging, and executes a traffic light recognition process of recognizing the color of a traffic light for pedestrians on the basis of the captured image.

In step S32, the guide information generation unit 62 determines, on the basis of a result of the traffic light recognition process, whether the color of the traffic light for pedestrians changes from red to green. In the case where it is not determined in step S32 that the traffic light changes from red to green, the process returns to step S31, and the processes of steps S31 and S32 are repeated. It is possible that the traffic light for pedestrians is already green at the time when a correct crossing direction is decided. However, the time before the traffic light turns red can also be short. Then, the process of step S32 detects the timing at which the traffic light for pedestrians changes from red to green, and attempts to secure as much crossing time as possible.

In the case where it is determined in step S32 that the color of the traffic light for pedestrians changes from red to green, the guide information generation unit 62 causes, in step S33, the output unit 17 to output the voice message of "The traffic light turns green. You can cross the road." and notifies the visually impaired person that the visually impaired person can cross the road.

In step S34, the PDR calculation unit 63 calculates the position and the azimuth from the crossing point. The guide information generation unit 62 acquires the position and the azimuth calculated by the PDR calculation unit 63.

Figure 11:
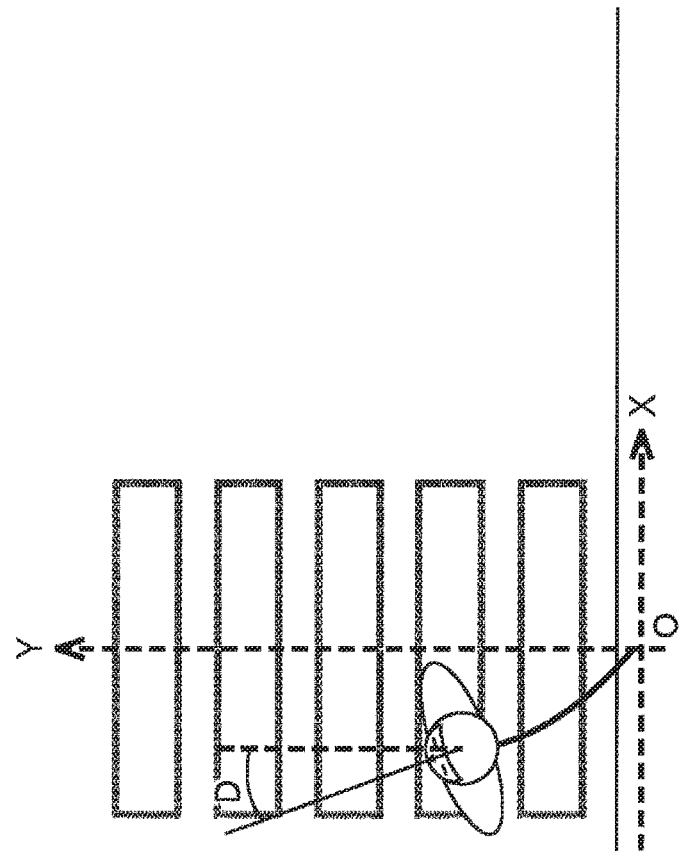
FIG. 11 is a diagram describing an output of a PDR calculation unit.

The PDR calculation unit 63 calculates movement distance Y in a crossing direction, movement distance X in the vertical direction with respect to the crossing direction, and an angular deviation amount D from the crossing direction as illustrated in FIG. 11 on the basis of a crossing point O, and outputs them to the guide information generation unit 62. The movement distance X in the vertical direction is a positional deviation in the horizontal direction in a sense. The angular deviation amount D from the crossing direction is a body orientation deviation in a sense. Accordingly, the following refers to them as the positional deviation X in the horizontal direction, and the body orientation deviation D.

In step S35, the guide information generation unit 62 determines whether the position or the azimuth deviate by a predetermined value or more.

Specifically, the guide information generation unit 62 uses the positional deviation X in the horizontal direction, and the body orientation deviation D which are supplied from the PDR calculation unit 63, and calculates a parameter $P=aX+kD$ (a and k represent predetermined constants). On the basis of whether or not the calculated parameter P is greater than or equal to a predetermined threshold, the guide information generation unit 62 determines whether the position or the azimuth deviates by a predetermined value or more.

In the case where it is determined in step S35 that the position or the azimuth does not deviate by the predetermined value or more, the process returns to step S34, and the processes of steps S34 and S35 described above are repeated.

In contrast, in the case where it is determined in step S35 that the position or the azimuth deviates by the predetermined value or more, the process proceeds to step S36, and the guide information generation unit 62 causes the output unit 17 to output the voice message of "right" or "left" and notifies a visually impaired person of a correction direction.

In step S37, the guide information generation unit 62 determines whether a button operation for the time when a visually impaired person finishes walking to the other side of a crosswalk is detected. When the visually impaired person finishes walking to the other side of a crosswalk, the visually impaired person depresses the operation button of the operation unit 14 or the operation button 42 of the wireless earphone 41.

In the case where it is determined in step S37 that the button operation for the time when a visually impaired person finishes walking to the other side of a crosswalk has not yet been detected, the process returns to step S34, and the processes of steps S34 to S37 described above are repeated.

Thus, according to the processes of steps S34 to S37, in the case where a visually impaired person is walking in a correct direction while the visually impaired person is walking on a crosswalk, no voice message is output. In the case where the advancing direction deviates at a certain level or more, the voice message of "right" or "left" is output. Note that electronic sound may be output like "beep, beep" at constant intervals to notify a visually impaired person that the direction is being detected and reassure the visually impaired person even in the case where the visually impaired person is walking in a correct direction.

In the case where it is determined in step S37 that the button operation for the time when a visually impaired person finishes walking to the other side of a crosswalk is detected, the guide information generation unit 62 issues a notification that the crossing mode is to terminate by voice via the output unit 17 in step S38.

In step S39, the guide information generation unit 62 determines whether to terminate the guide mode. For example, when a visually impaired person performs an operation of terminating the guide app in the case where the visually impaired person arrives at a destination, it is determined to terminate the guide mode.

In the case where it is determined in step S39 that the guide mode is not terminated, the process returns to step S22, and the processes described above are repeated. That is, it is monitored whether or not the next crossing point whose Ref image is registered is present nearby, and the processes from step S23 are executed on the detected next crossing point.

In contrast, in the case where it is determined in step S39 to terminate the guide mode, the crosswalk guide process terminates.

According to the crosswalk guide process described above, at each crosswalk (crossing point) whose Ref image is registered, the direction detection process of deciding a correct crossing direction on the basis of a matching result obtained by matching a Ref image stored in advance with a still image (current image) captured at the current time point is performed by the Ref image registration unit 51. In addition, in the case where, while a visually impaired person is walking on a crosswalk, the advancing direction deviates from the crossing direction at a certain level or more, a process of notifying the visually impaired person of a correction direction is executed by the guide information generation unit 62. As a result, it is possible to safely walk on the crosswalk in the correct direction.

<1.8 Modification of Ref Image Registration Process and Crosswalk Guide Process>

A modification of the Ref image registration process and the crosswalk guide process described above will be described.

When it is determined at a crossing point whether or not a visually impaired person faces in a correct direction, attitude information of the visually impaired person which is detected by the direction sensor 12 may be referred to. In this case, when a Ref image is registered, azimuth information detected by the direction sensor 12 when the Ref image is captured is also stored as attitude information in the storage unit 15 along with the Ref image.

In the Ref image registration process described above, time information stored along with a Ref image is taken to be the elapsed time from a departure point. However, in the case where a visually impaired person leaves a departure point at the same time every day, not elapsed time, but absolute time of the 24-hour clock may be used.

In the crosswalk guide process described above, the deviation amount of a visually impaired person walking on a crosswalk is determined by calculating the parameter P=aX+kD without distinguishing between the positional deviation X in the horizontal direction and the body orientation deviation D. However, the positional deviation X in the horizontal direction and the body orientation deviation D may each have a threshold, and may be separately determined. In this case, the guide information generation unit 62 may use different electronic sounds for the positional deviation X in the horizontal direction and the body orientation deviation D to notify a visually impaired person of a correction direction. For example, with respect to the positional deviation X in the horizontal direction, the large positional deviation X causes a low-pitched electronic sound, and the small positional deviation X causes a high-pitched electronic sound. With respect to the body orientation deviation D, facing in a correct direction causes a low-toned electronic sound, and facing a deviate direction causes a high-toned electronic sound.

Figure 12:
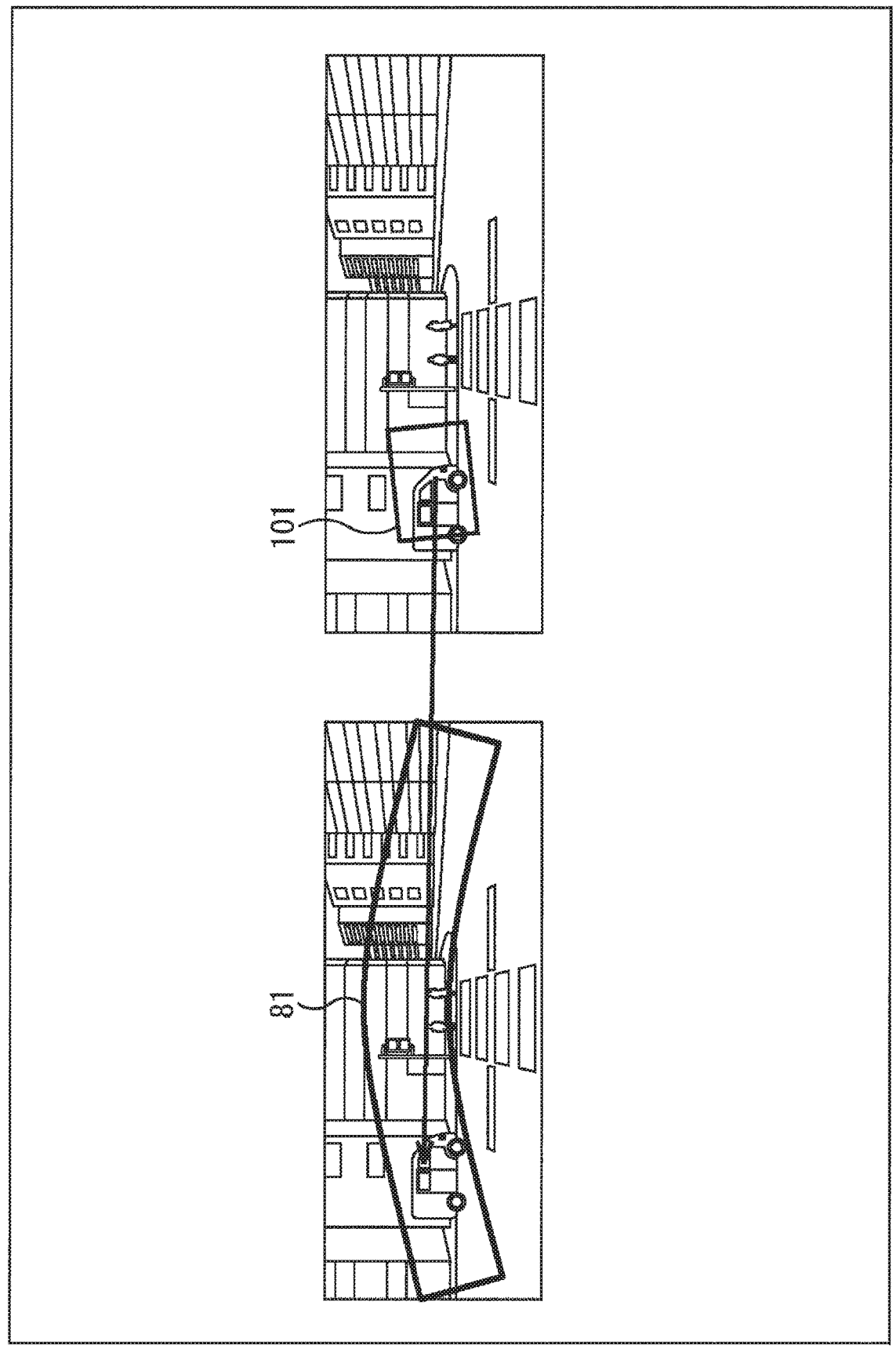
FIG. 12 is a diagram illustrating a modification of a Ref image.

In the Ref image registration process described above, as a Ref image registered in the storage unit 15, a panoramic image whose imaging range is wide in the horizontal direction may be captured and registered. This facilitates matching even in the case where a visually impaired person faces in a considerably oblique direction with respect to a crosswalk as illustrated in FIG. 12. In addition, in this case, azimuth information for the time of capturing a panoramic image may also be added and stored as attitude information. Moreover, instead of a panoramic image, a moving image captured by panning may be used as a Ref image.

Figure 13:
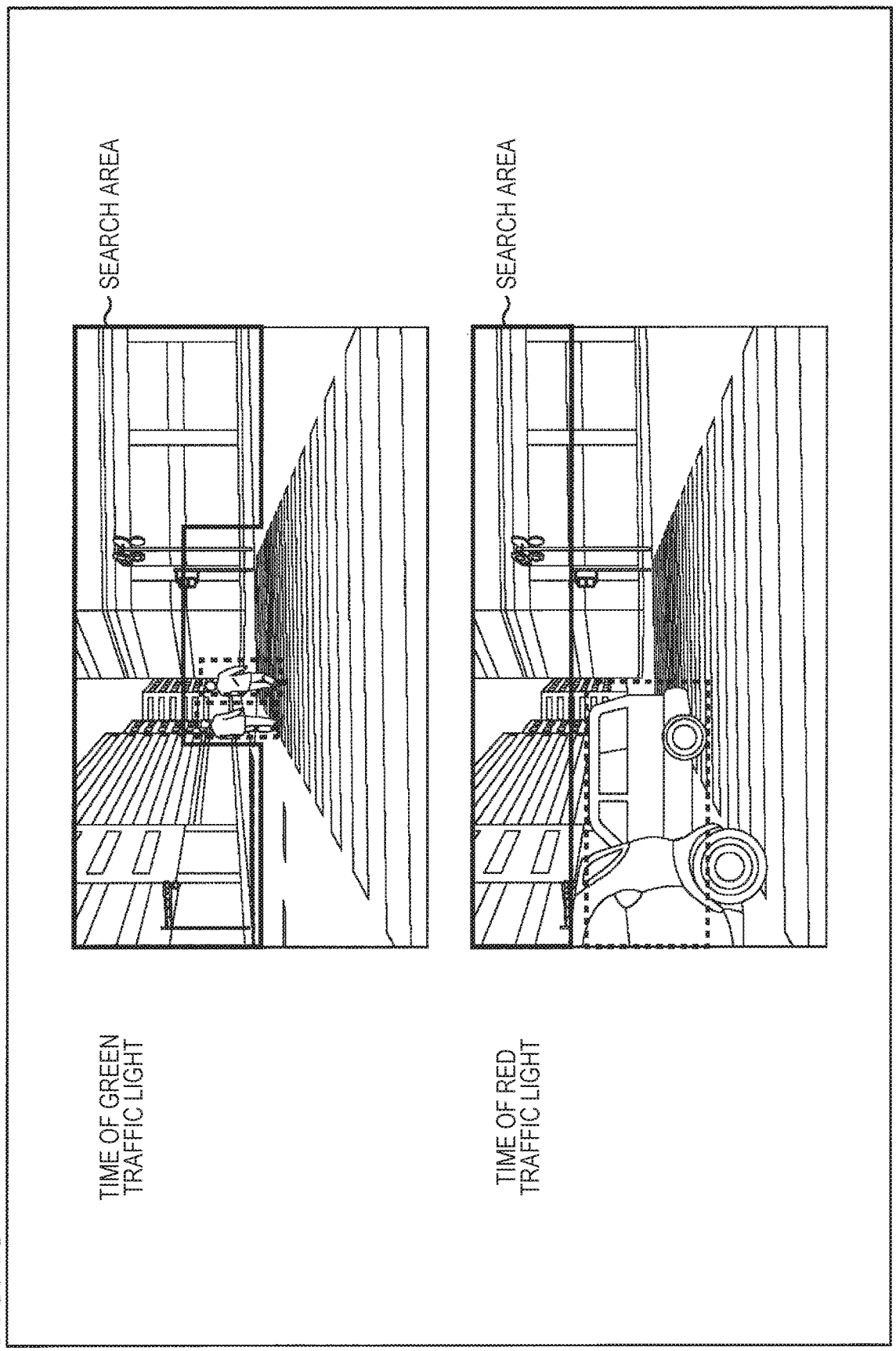
FIG. 13 is a diagram illustrating a modification of a search area.

In the crosswalk guide process described above, a search area of a current image in the case of feature point matching to detect a feature point corresponding to a feature point of a Ref image is taken to be the entire range of the current image, but the search area may be taken to be a partial area of the current image, and may be further changed as illustrated in FIG. 13 in accordance with whether the color of the traffic light for pedestrians is green or red.

When the traffic light for pedestrians is green, the current image is likely to show a crossing pedestrian. Meanwhile, when the traffic light for pedestrians is red, a vehicle crossing a crosswalk is likely to appear. Therefore, to eliminate these pedestrian and vehicle, the direction decision unit 61 can exclude the lower side area of a current image a large portion of which is occupied by a road as illustrated in FIG. 13 from the search area, and set different areas for a green traffic light for pedestrians and a red traffic light for pedestrians. With respect to a current image in which the color of the traffic light for pedestrians is red, the feature point extraction or the matching process itself may be stopped.

Figure 14:
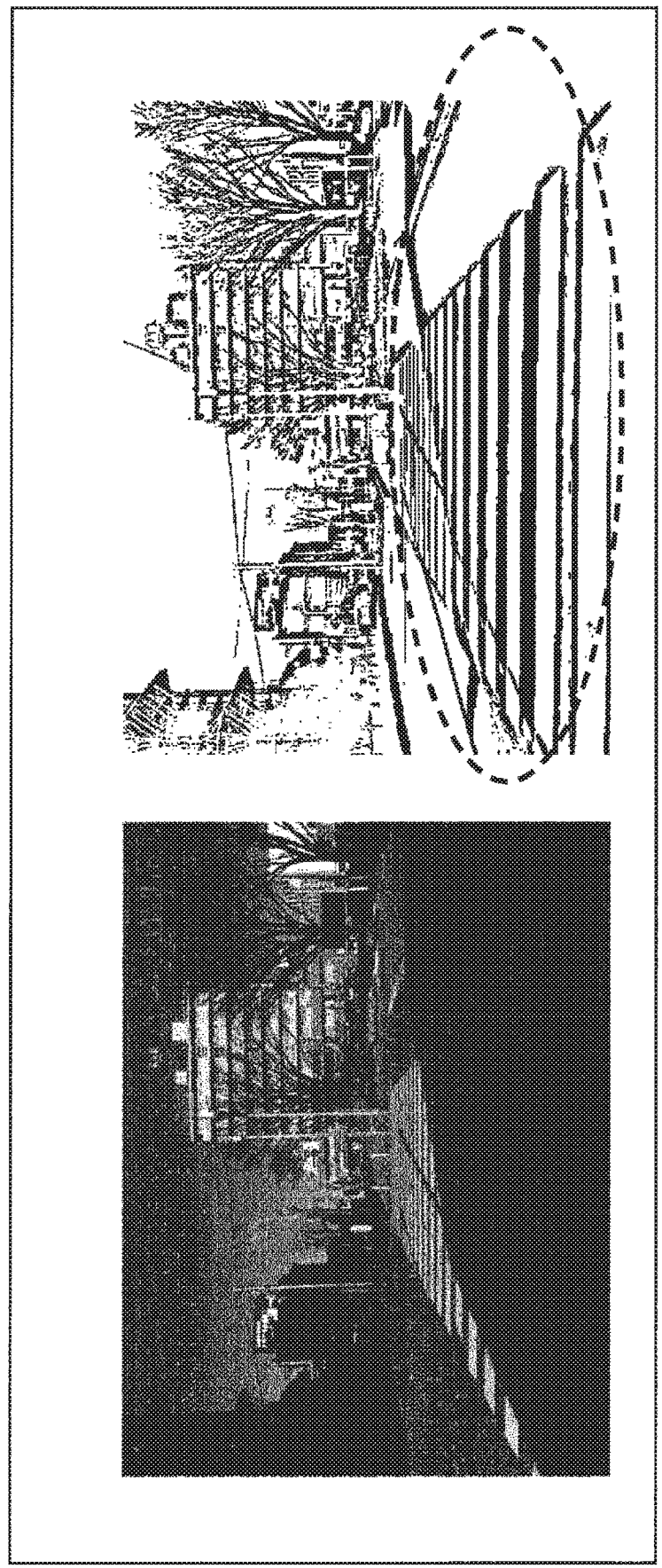
FIG. 14 is a diagram illustrating a modification of a matching process.

When the time of registering a Ref image in the registration mode is different from the time of capturing a current image in the guide mode, sunshine makes different shadows and it is not possible in some cases to match local feature amounts. In such a case, as illustrated in FIG. 14, it is also possible to exclude shadows by binarizing an image, and then perform the matching process. In the example of FIG. 14, a large shadow on a road indicated by a dashed line is excluded, and it is possible to eliminate the influence of the position of the shadow.

In the direction detection process described above, the direction in which a visually impaired person faces is detected on the basis of the number of pixels of a captured current image in the horizontal direction. This direction is the detection of a direction using a so-called relative azimuth with a current image used as the center, but the direction in which a visually impaired person faces can also be detected using a direction with an absolute azimuth on the basis of a reference coordinate (e.g., on the basis of a magnetic azimuth).

Figure 15:
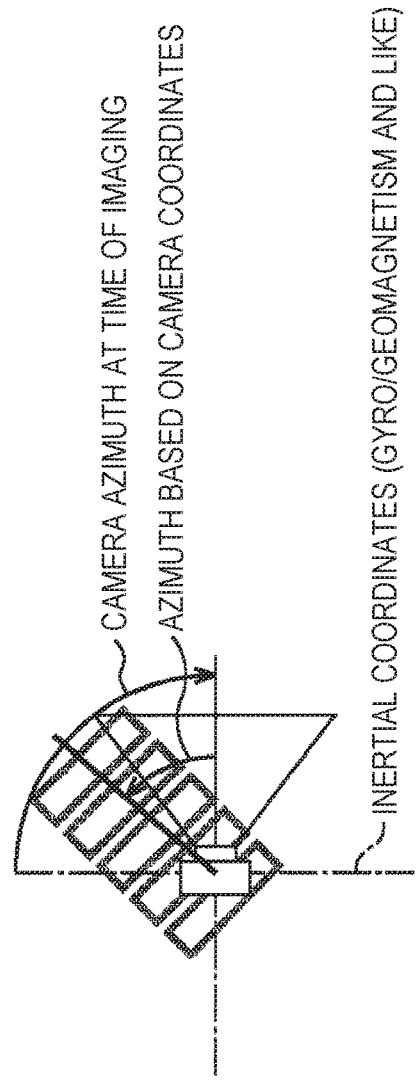
FIG. 15 is a diagram illustrating a modification of the direction detection process.

The estimated azimuth based on a reference coordinate can be calculated, as illustrated in FIG. 15, by adding an azimuth (azimuth based on the center of an image) based on a camera coordinate to a camera azimuth (azimuth of the camera 11 when a still image is captured) at the time of imaging.

Figure 16:
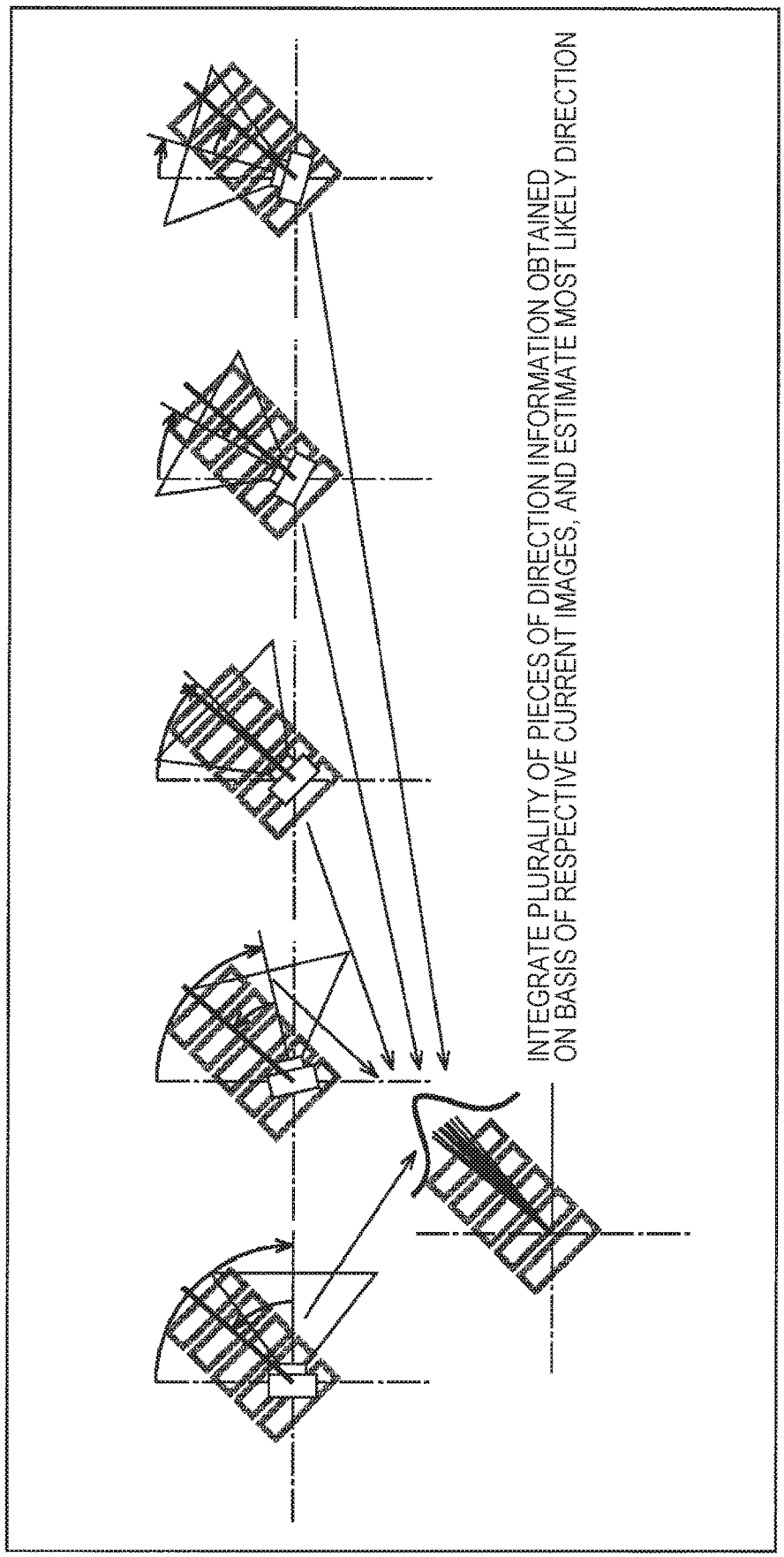
FIG. 16 is a diagram illustrating a modification of the direction detection process.

In addition, in the direction detection process described above, a feature point is extracted, the direction in which a visually impaired person faces is estimated, and an audio output is made as guide information whenever one current image is captured. However, as illustrated in FIG. 16, the direction in a visually impaired person faces may be generally determined on the basis of a result detected in each of a plurality of current images, and a final direction may be estimated.

In other words, the direction decision unit 61 repeats the direction detection process of FIG. 9 a plurality of times (plurality of images), and integrates a plurality of pieces of direction information that are each detected to make one detection result regarding the direction in which a visually impaired person faces.

For example, the direction decision unit 61 can calculate the average value of a plurality of pieces of direction information detected in each of a plurality of current images, and use a resultant direction as the direction in which a visually impaired person faces.

Alternatively, a predetermined weighted averaging process may be performed on a plurality of directions detected in each of a plurality of current images to detect a final direction.

For example, a projection frame of a current image closer to the image center leads to higher accuracy. Accordingly, among a plurality of current images, a current image in which the position of a projection frame is closer to the image center is weighted more, and it is possible to decide a direction in which a plurality of directions detected in each of the plurality of current images are integrated.

For example, a plurality of current images may be weighted on the basis of an inlier match amount. That is, among a plurality of current images, a current image having more feature points used to calculate a projective transformation matrix is weighted more, and it is possible to decide a direction in which a plurality of directions detected in each of the plurality of current images are integrated.

Alternatively, a plurality of current images may be weighted in accordance with geometric information of a projection frame. Among a plurality of current images, a current image whose projection frame has a shape more similar to a quadrangle is weighted more, and it is possible decide a direction in which a plurality of directions detected in each of the plurality of current images are integrated.

Alternatively, a current image in which the color of the traffic light for pedestrians is blue considered to show less vehicles and make it possible to detect an accurate azimuth. Accordingly, a current image in which the color of the traffic light for pedestrians is blue is weighted more, and a current image in which the color of the traffic light for pedestrians is red is weighted less. This makes it possible to decide a direction in which a plurality of directions detected in each of the plurality of current images are integrated.

Figure 17:
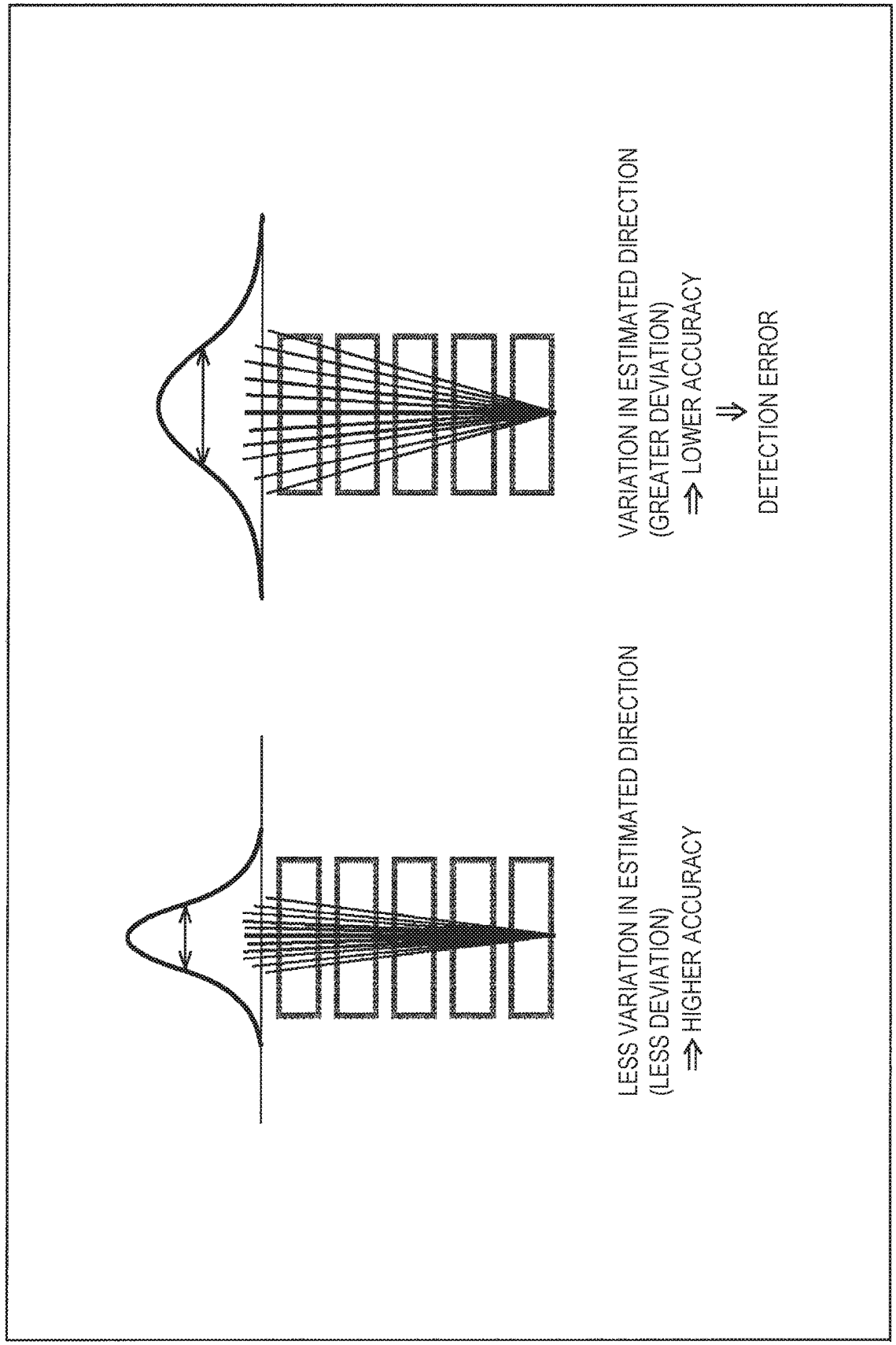
FIG. 17 is a diagram illustrating a modification of the direction detection process.

In addition, in the case where a plurality of directions detected in each of a plurality of current images are integrated to finally decide a direction as illustrated in FIG. 17, the deviation of the plurality of detected directions is calculated. In the case where the deviation is greater than or equal to a predetermined threshold, a voice message that announces a correction direction may be prevented from being output as a detection error. In addition, in the case where a detection error is determined, the voice message of "Stay still" may be output to wait until the deviation becomes less than or equal to the predetermined threshold, or the number of current images to be integrated may be increased. This can improve the estimation accuracy. In the case where the accuracy is low, no announcement of a correction direction is output, and it is thus possible to prevent danger.

Figure 18:
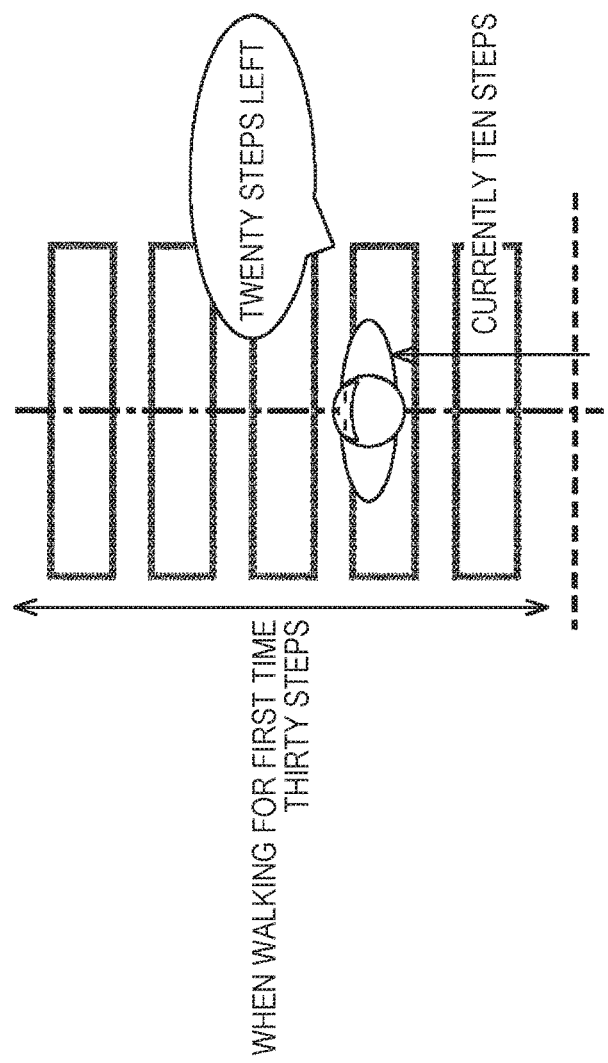
FIG. 18 is a diagram illustrating a modification of the crosswalk guide process.

In the crosswalk guide process described above, as illustrated in FIG. 18, while a visually impaired person is walking on a crosswalk, the guide information generation unit 62 may count the number of steps walked by the visually impaired person from the crossing point and cause information regarding the remaining distance to the other side of the crosswalk to be output as a voice message, for example, like "twenty steps left" or "one meter left". With respect to the information regarding the distance of the entire crosswalk, the number of steps may be automatically counted in the registration mode when a visually impaired person walks on the crosswalk, or an accompanying protector may be asked to input the number of steps after the visually impaired person walks to the other side of the crosswalk. Alternatively, a Ref image is captured to include the entire crosswalk, and it is also possible to estimate the distance of the entire crosswalk from the number of black and white lines of the crosswalk included in the Ref image and store the distance of the entire crosswalk.

<2. Entire Route Guide Function>

<2.1 Overview of Entire Route Guide Function>

Next, an entire route guide function that the information processing apparatus 1 further includes in addition to the crosswalk walking guide function described above will be described.

The crosswalk walking guide function described above is a guide function that focuses on only a crosswalk on a moving route from a departure point to a predetermined destination. However, with respect to a moving route except for a crosswalk, the information processing apparatus 1 can provide an entire route guide function described below.

Figure 19:
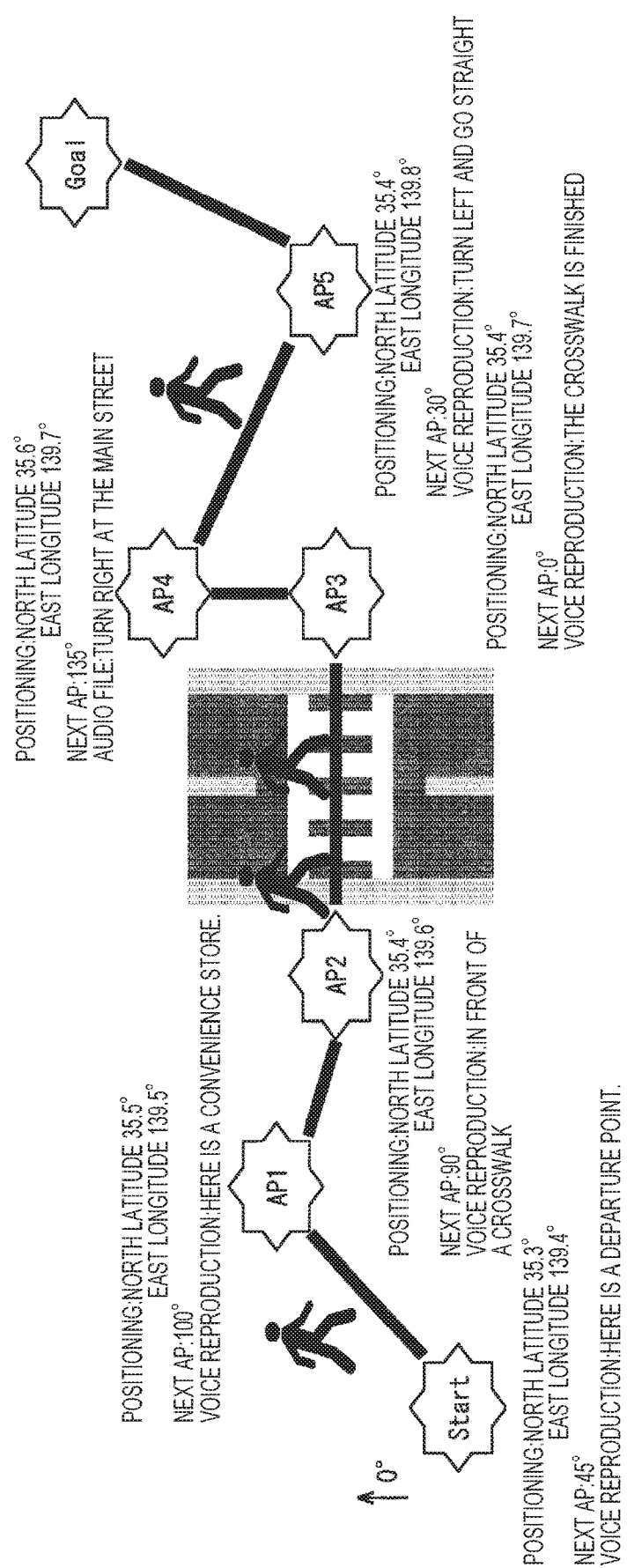
FIG. 19 is a diagram describing an overview of an entire route guide function.

FIG. 19 is a diagram describing the overview of the entire route guide function.

When a visually impaired person moves to a destination for the first time, the visually impaired person records guide information regarding a checkpoint as serving as a walking reference by his or her voice at a main checkpoint on a moving route from a departure point to a predetermined destination for each checkpoint.

The information processing apparatus 1 stores the voice uttered by the visually impaired person, and positional information and time information indicating the place (latitude and longitude) in which the voice is recorded in the storage unit 15 for each checkpoint. Then, the information processing apparatus 1 reproduces (outputs) the voice recorded as guide information for each checkpoint when moving to the destination for the second time or later. The recording of guide information in the movement for the first time is executed in the registration mode. The reproduction of the recorded voice for the second time or later is executed in the guide mode.

FIG. 19 illustrates an example in which guide information is registered for a departure point, a destination, and five checkpoints.

First, when, at a departure point Start, a visually impaired person begins to execute the guide mode of the entire route guide function, the information processing apparatus 1 outputs the voice message of "Here is a departure point." recorded in advance by the visually impaired person at the departure point Start.

Next, when the visually impaired person moves near a checkpoint AP1 at which voice is next recorded, the information processing apparatus 1 outputs the voice message of "Here is a convenience store." recorded in advance by the visually impaired person at the checkpoint AP1.

Next, when the visually impaired person moves near a checkpoint AP2 at which voice is next recorded, the information processing apparatus 1 outputs the voice message of "In front of a crosswalk." recorded in advance by the visually impaired person at the checkpoint AP2.

Next, when the visually impaired person moves near a checkpoint AP3 at which voice is next recorded, the information processing apparatus 1 outputs the voice message of "The crosswalk is finished." recorded in advance by the visually impaired person at the checkpoint AP3.

Next, when the visually impaired person moves near a checkpoint AP4 at which voice is next recorded, the information processing apparatus 1 outputs the voice message of "Turn right at the main street." recorded in advance by the visually impaired person at the checkpoint AP4.

Next, when the visually impaired person moves near a checkpoint AP5 at which voice is next recorded, the information processing apparatus 1 outputs the voice message of "Turn left and go straight." recorded in advance by the visually impaired person at the checkpoint AP5.

Next, when the visually impaired person moves near a destination Goal at which voice is next recorded, the information processing apparatus 1 outputs the voice message of "I have arrived at the destination." recorded in advance by the visually impaired person at the destination Goal.

In addition, the information processing apparatus 1 may output the rough direction of the next checkpoint by voice with recorded voice at each checkpoint on the basis of positional information stored in association with the voice message.

For example, at the departure point Start, the direction toward the next checkpoint AP1 is a 45-degree direction. Accordingly, the voice message of "Next, 45-degree direction." may be output along with the voice message of "Here is a departure point." The same applies to the other checkpoints.

When walking for the first time, a visually impaired person records, as a voice message, information noticed by the visually impaired person including, for example, a feature such as sound and smell at each point on a moving route, a congestion situation of a sidewalk, a feature of a road, information (such as turning left, going straight, and turning right) serving as a hint to prevent the visually impaired person from losing his or her way at a crossroad, a difference in situation on each day, and the like.

Figure 20:
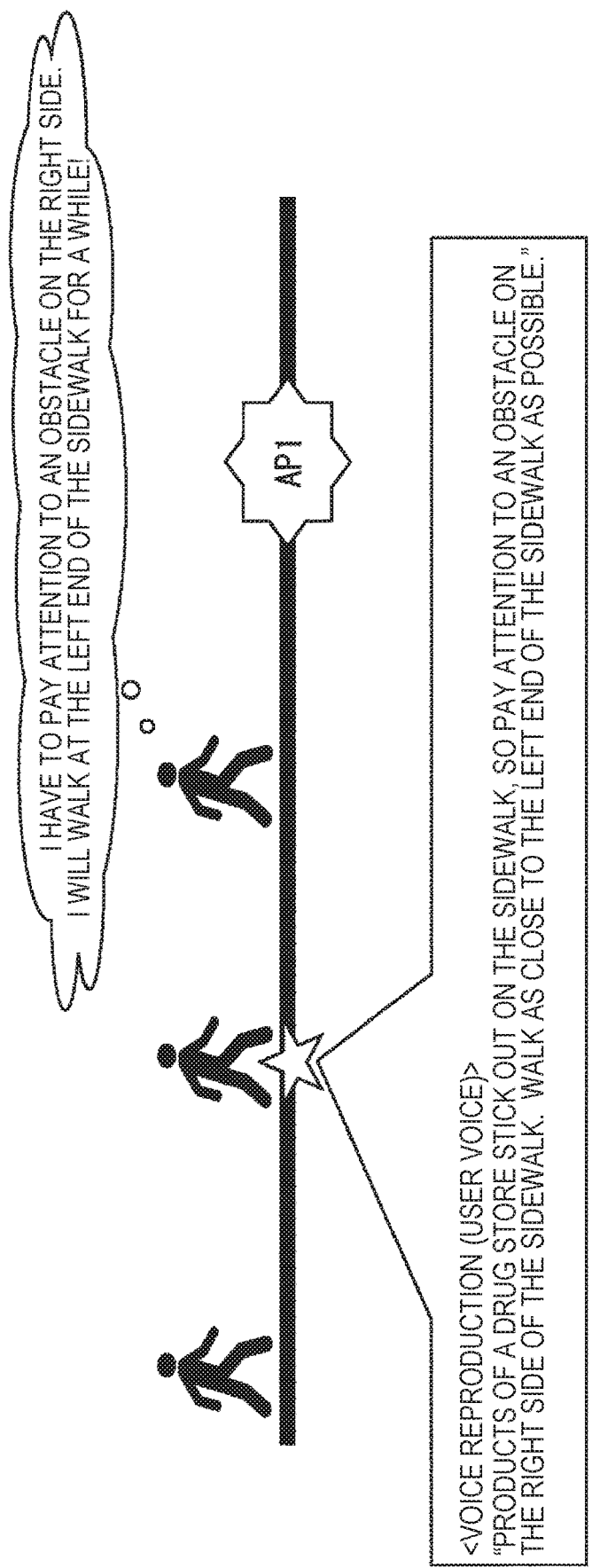
FIG. 20 is a diagram illustrating an example in which obstacle information is recorded as guide information.

FIG. 20 illustrates an example in which obstacle information is recorded as guide information.

When walking for the first time, a visually impaired person records, for example, the voice of "Products of a drug store stick out on the sidewalk, so pay attention to an obstacle on the right side of the sidewalk. Walk as close to the left end of the sidewalk as possible." for the checkpoint AP1 in the information processing apparatus 1. When walking for the second time or later, the visually impaired person can pay attention to an obstacle on the right side and walk at the left end of the sidewalk because this voice message is reproduced.

Figure 21:
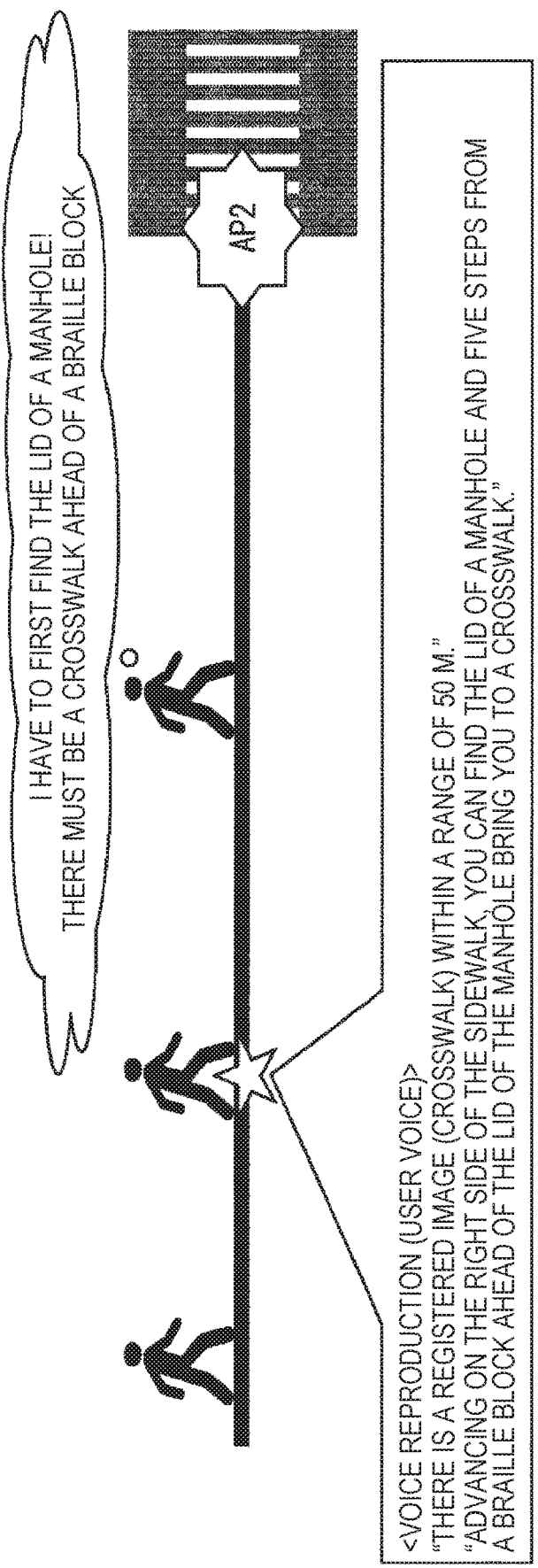
FIG. 21 is a diagram illustrating an example in which a hint of a crosswalk is recorded as the guide information.

FIG. 21 illustrates an example in which a hint of a crosswalk is recorded as guide information.

When walking for the first time, a visually impaired person records, for example, the voice of "There is a crosswalk within a range of 50 m. Advancing on the right side of the sidewalk, you can find the lid of a manhole and five steps from a braille block ahead of the lid of the manhole bring you to a crosswalk." for the checkpoint AP2 in the information processing apparatus 1. When walking for the second time or later, the visually impaired person can easily arrive at the crosswalk on the basis of the lid of the manhole and the Braille block because this voice message is reproduced.

Note that it is described in the present embodiment that a visually impaired person himself or herself records a voice message (records voice) at each checkpoint, but an accompanying protector may record a voice message.

<2.2 Configuration Example of Information Processing Apparatus>

Figure 22:
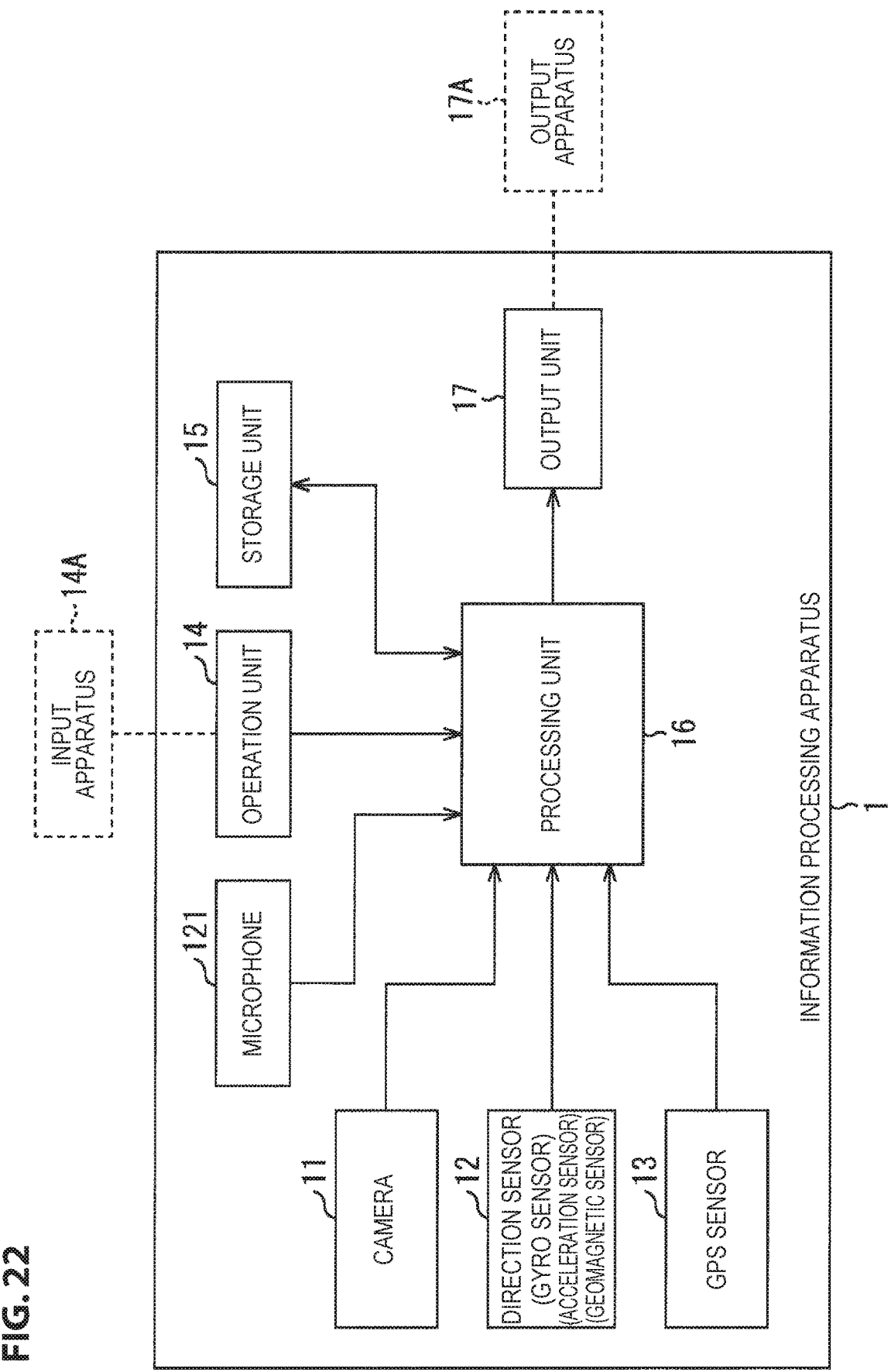
FIG. 22 is a block diagram illustrating a configuration example of the information processing apparatus in a case where the entire route guide function is executed.

FIG. 22 is a block diagram illustrating a configuration example of the information processing apparatus in the case where the entire route guide function described above is executed.

Note that the parts of FIG. 22 which correspond to the parts of FIG. 2 are denoted with the same reference numerals, and the description thereof will be omitted as appropriate. The same applies to FIG. 23 or subsequent figures.

The information processing apparatus 1 can execute the entire route guide function by adding a microphone 121 to the components illustrated in FIG. 2.

The microphone 121 picks up the voice uttered by a visually impaired person to supply the voice to the processing unit 16 as an audio signal.

<2.3 Functional Block Diagram of Processing Unit>

Figure 23:
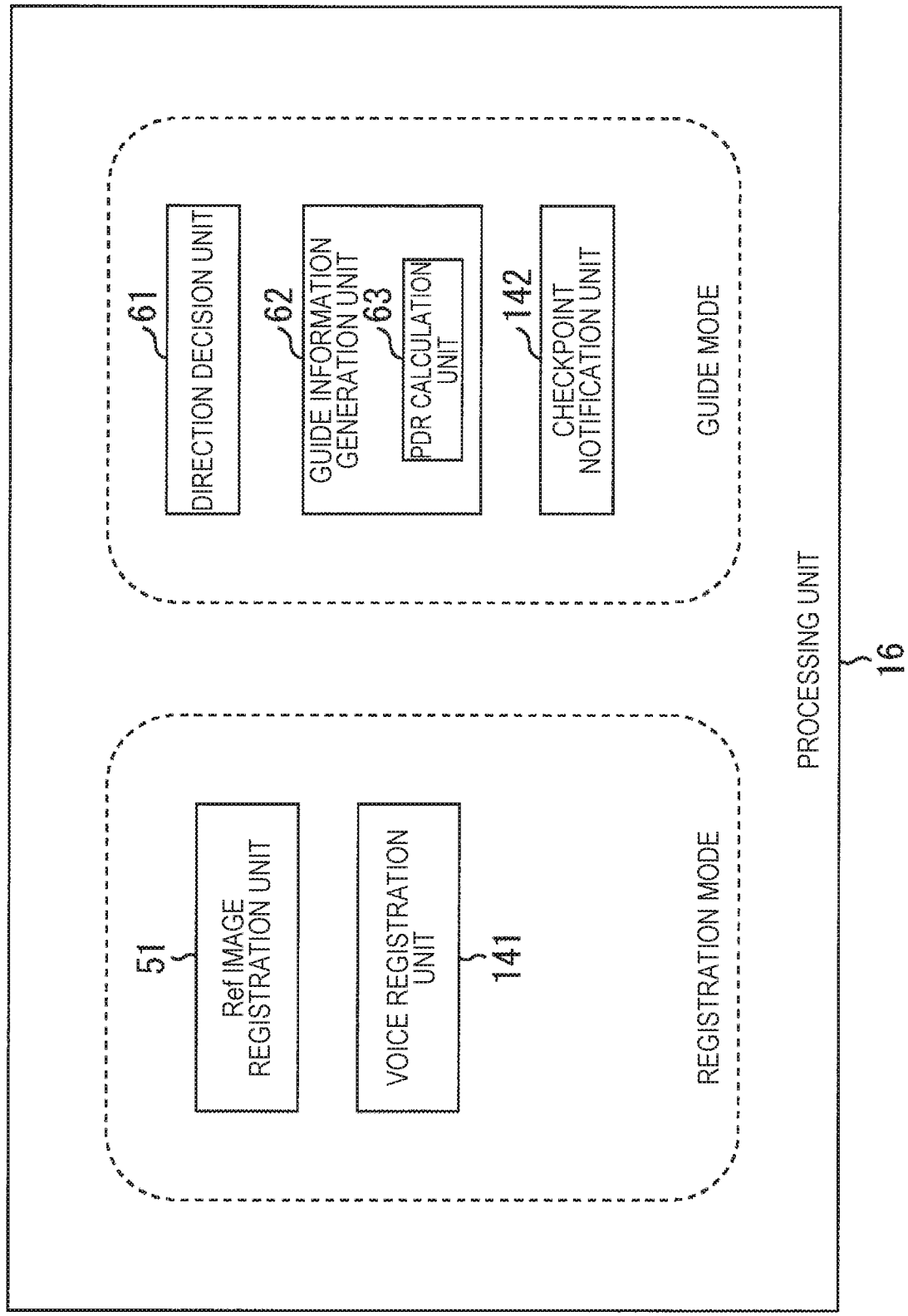
FIG. 23 is a functional block diagram of the processing unit in the case where the entire route guide function is executed.

FIG. 23 is a functional block diagram of the processing unit 16 in the case where the entire route guide function described above is executed.

The processing unit 16 includes a voice registration unit 141 as the registration mode in addition to the Ref image registration unit 51 described above.

In addition, the processing unit 16 includes a checkpoint notification unit 142 as the guide mode in addition to the direction decision unit 61 and the guide information generation unit 62 described above.

When a visually impaired person moves to a destination for the first time, the voice registration unit 141 converts an audio signal supplied from the microphone 121 in a predetermined format in accordance with a recording operation performed by the visually impaired person for each checkpoint, and causes the storage unit 15 to store the converted audio signal. In addition, when storing (data of) the voice of the visually impaired person in the storage unit 15, the voice registration unit 141 causes the storage unit 15 to store positional information and time information of the checkpoint in association with the voice.

The checkpoint notification unit 142 determines, when moving to the destination for the second time or later, whether or not a checkpoint is approached. In the case where it is determined that a checkpoint is approached, the checkpoint notification unit 142 acquires (the data of) the voice stored in association with the checkpoint from the storage unit 15 and causes the output unit 17 to output the acquired voice.

Note that, in the entire route guide function, the processes on a departure point and a destination are not different from the process on a checkpoint. Accordingly, it is assumed that the process is performed with a departure point and a destination recognized as one of checkpoints.

The registration mode and the guide mode may be each configured as one app, or the voice registration unit 141 and the checkpoint notification unit 142 may be each configured as one app. In other words, the app of the crosswalk walking guide function and the app of the entire route guide function described above may be configured as one app or different apps. Individual apps are configured in any functional units.

<2.4 Voice Registration Process>

Figure 24:
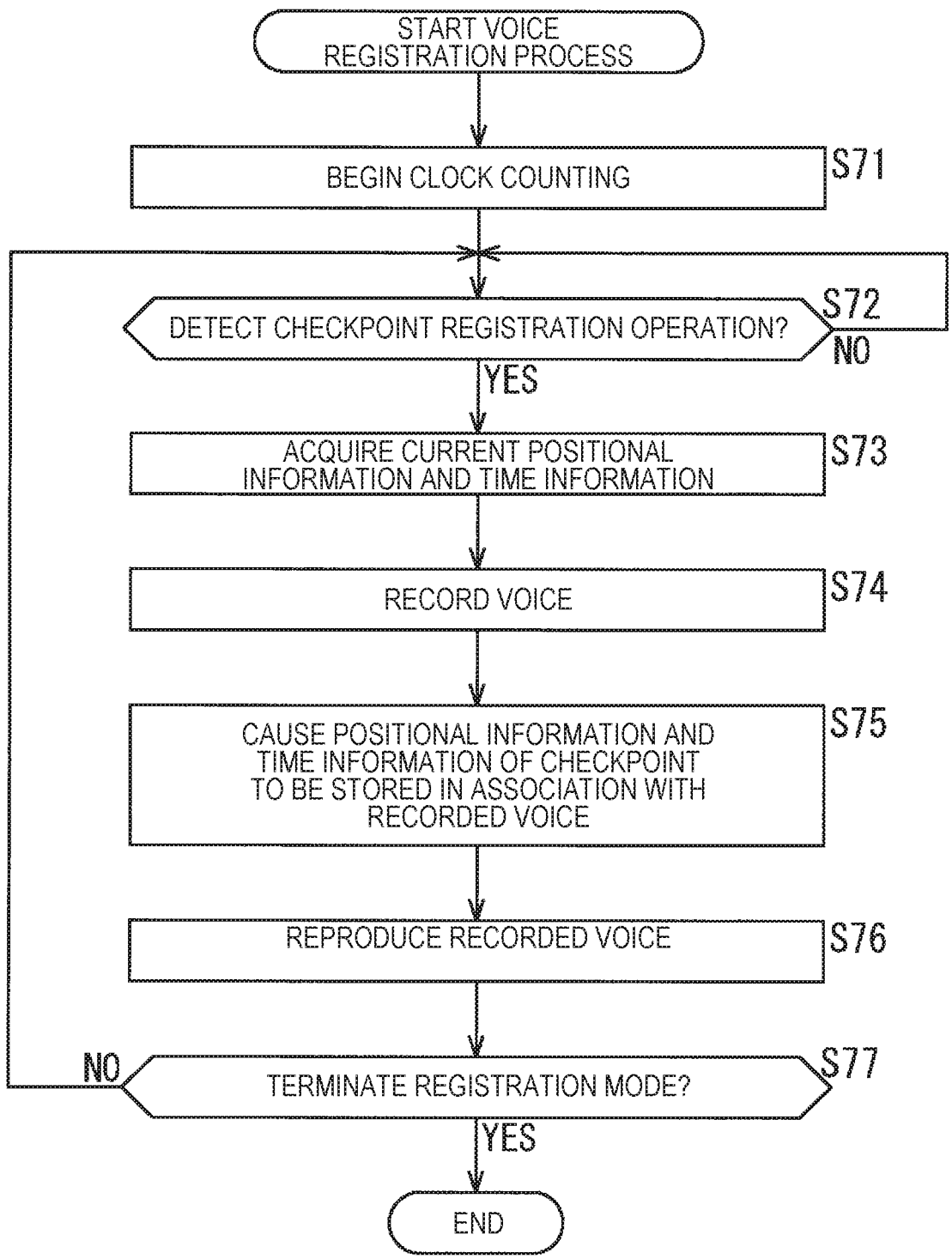
FIG. 24 is a flow chart describing a voice registration process of the entire route guide function.

With reference to the flow chart of FIG. 24, a voice registration process executed by the voice registration unit 141 in the registration mode will be described. This process is begun, for example, when a registration app is executed at the timing at which a visually impaired person begins to move from a departure point to a predetermined destination with an accompanying protector.

First, in step S71, the voice registration unit 141 begins clock counting for measuring the elapsed time (necessary time) from the departure point.

In the case where a visually impaired person wishes to record guide information as serving as a walking reference, the visually impaired person performs an operation for recording guide information regarding a checkpoint (which will be referred to as checkpoint registration operation below). Examples of the checkpoint registration operation include depressing the operation button 42 of the wireless earphone 41.

In step S72, the voice registration unit 141 determines on the basis of an operation signal from the operation unit 14 whether a checkpoint registration operation is detected, and waits until it is determined that a checkpoint registration operation is detected.

In the case where it is determined in step S72 that a checkpoint registration operation is detected, the process proceeds to step S73, and the voice registration unit 141 acquires current positional information and time information as positional information and time information of a checkpoint. That is, the voice registration unit 141 acquires positional information that is supplied from the GPS sensor 13 and indicates the current latitude and longitude, and the elapsed time from the counting begun in step S71 as positional information and time information of a checkpoint.

In step S74, the voice registration unit 141 records the voice uttered by the visually impaired person which is supplied from the microphone 121 (causes the storage unit 15 to store the voice).

In step S75, the voice registration unit 141 causes the storage unit 15 to store the positional information and the time information of a checkpoint which is acquired in step S73 in association with the recorded voice.

In step S76, the voice registration unit 141 reproduces the recorded voice to allow the visually impaired person to check the recorded content. That is, the voice registration unit 141 outputs the audio signal corresponding to the data of the voice stored in the storage unit 15 to the speaker or the earphone serving as the output unit 17.

In step S77, the voice registration unit 141 determines whether to terminate the registration mode. For example, in the case where a visually impaired person and an accompanying protector arrive at a destination, it is determined with an operation of the visually impaired person to terminate a registration app that the registration mode is terminated.

In the case where it is determined in step S77 that the registration mode is not still terminated, the process returns to step S72, and the processes of steps S72 to S77 described above are repeated. Whenever a checkpoint registration operation is performed, this causes the positional information and the time information of a checkpoint and the voice to be stored in the storage unit 15.

In contrast, in the case where it is determined in step S77 that the registration mode is terminated, the voice registration process terminates.

<2.5 Checkpoint Guide Reproduction Process>

Figure 25:
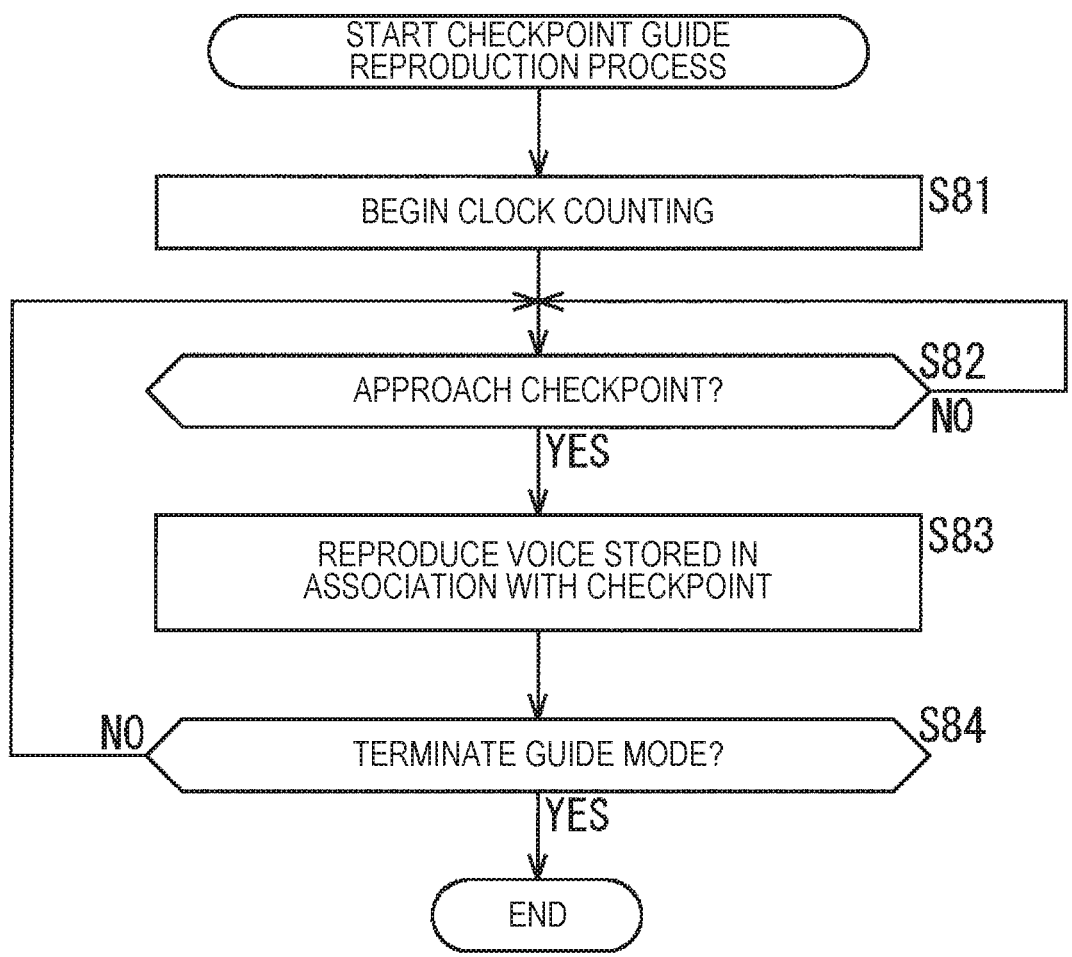
FIG. 25 is a flow chart describing a checkpoint guide reproduction process of the entire route guide function.

Next, with reference to the flow chart of FIG. 25, a checkpoint guide reproduction process executed by the checkpoint notification unit 142 in the guide mode will be described. This process is begun, for example, when the guide app is executed at the timing at which movement is begun at a departure point in the case where a visually impaired person walks alone on a moving route registered in the registration mode.

First, in step S81, the checkpoint notification unit 142 begins clock counting for measuring the elapsed time (necessary time) from the departure point.

In step S82, the checkpoint notification unit 142 acquires current positional information from the GPS sensor 13, and determines, on the basis of the acquired current positional information and the elapsed time from the departure point, whether a checkpoint for which voice is stored in the storage unit 15 is approached. More specifically, the checkpoint notification unit 142 compares the positional information and the time information of the checkpoint stored in association with voice stored in the storage unit 15 with the current positional information and the elapsed time to determine whether voice associated with a position within a predetermined range from the current positional information is registered in the storage unit 15. It depends on the positional accuracy of the GPS sensor 13, but, for example, when a visually impaired person arrives within a range of 50 to 100 m from a checkpoint, it is determined that the checkpoint is approached. A checkpoint is basically found with positional information, and time information is referred to.

Until it is determined in step S82 that the checkpoint is approached, the process of step S82 is repeated.

Then, in the case where it is determined in step S82 that a checkpoint is approached, the process proceeds to step S83, and the checkpoint notification unit 142 reproduces the voice stored in association with a checkpoint (positional information) close to the current value. That is, the checkpoint notification unit 142 acquires the data of the voice stored in association with a checkpoint (positional information) close to the current value from the storage unit 15, and causes the output unit 17 to output the acquired data.

In step S84, the voice registration unit 141 determines whether to terminate the guide mode. For example, when a visually impaired person performs an operation of terminating the guide app in the case where the visually impaired person arrives at a destination, it is determined to terminate the guide mode.

In the case where it is determined in step S84 that the guide mode is not still terminated, the process returns to step S82, and the processes of steps S82 to S84 described above are repeated. Whenever the visually impaired person passes by a checkpoint, this causes a voice message serving as the guide information corresponding to the checkpoint to be output.

In contrast, in the case where it is determined in step S84 to terminate the guide mode, the checkpoint guide reproduction process terminates.

As described above, according to the entire route guide function of the information processing apparatus 1, a visually impaired person himself or herself reproduces guide information recorded for a main checkpoint on a moving route by his or her voice when actually walking, thereby making it possible to help the visually impaired person safely walk.

Figure 26:
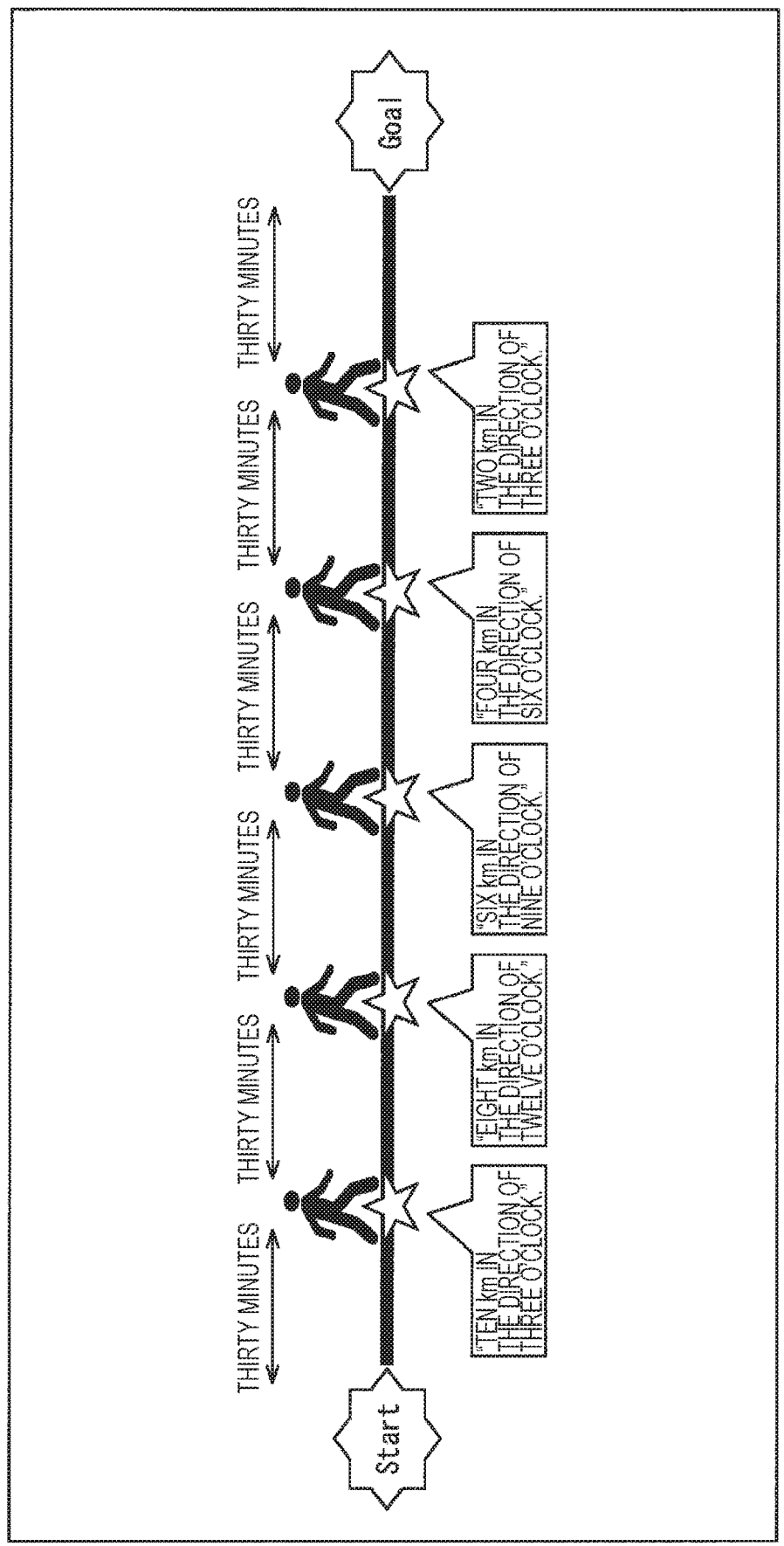
FIG. 26 is a diagram describing an additional entire route guide function.

Note that the information processing apparatus 1 can further include the entire route guide function (second entire route guide function) illustrated in FIG. 26 in addition to the entire route guide function (first entire route guide function) described above.

The entire route guide function illustrated in FIG. 26 is a function of outputting not a checkpoint set by a visually impaired person himself or herself, but the direction and the distance to a destination by voice at constant time intervals on the basis of positional information from the GPS sensor 13.

In the example of FIG. 26, every thirty minutes, the voice of the direction to a destination (such as "Direction of 3 o'clock" and "Direction of 12-o'clock") and the distance to the destination (such as "It is 10 km" and "It is 8 km") at that time point is output from the information processing apparatus 1.

<3. Second Visually Impaired Person Walking Support System>

<3.1 Overview of Second Visually Impaired Person Walking Support System>

Next, a second visually impaired person walking support system according to the present disclosure will be described.

The first visually impaired person walking support system described above is a system that can be implemented by the information processing apparatus 1 alone, but the second visually impaired person walking support system is a visually impaired person walking support system that uses an unmanned aircraft that is referred to as so-called drone.

With reference to FIG. 27, the overview of the second visually impaired person walking support system will be described.

A visually impaired person wears a hat (not illustrated) or the like having a two-dimensional code written thereon as a marker 161 to reduce erroneous recognition, and walks on a moving route. A drone 171 detects the marker 161, and moves right above the visually impaired person to image the area right below.

An image captured by the drone 171 is transferred to the information processing apparatus 1, and the information processing apparatus 1 compares a Ref image captured in advance with the image transferred from the drone 171 to detect a deviation from the correct position and inform the visually impaired person of the correct position by voice.

This second visually impaired person walking support system that uses a drone can be used to lead a visually impaired person to an accurate crossing point, for example, when the visually impaired person walks on a crosswalk.

<3.2 Configuration Example of Second Visually Impaired Person Walking Support System>

Figure 28:
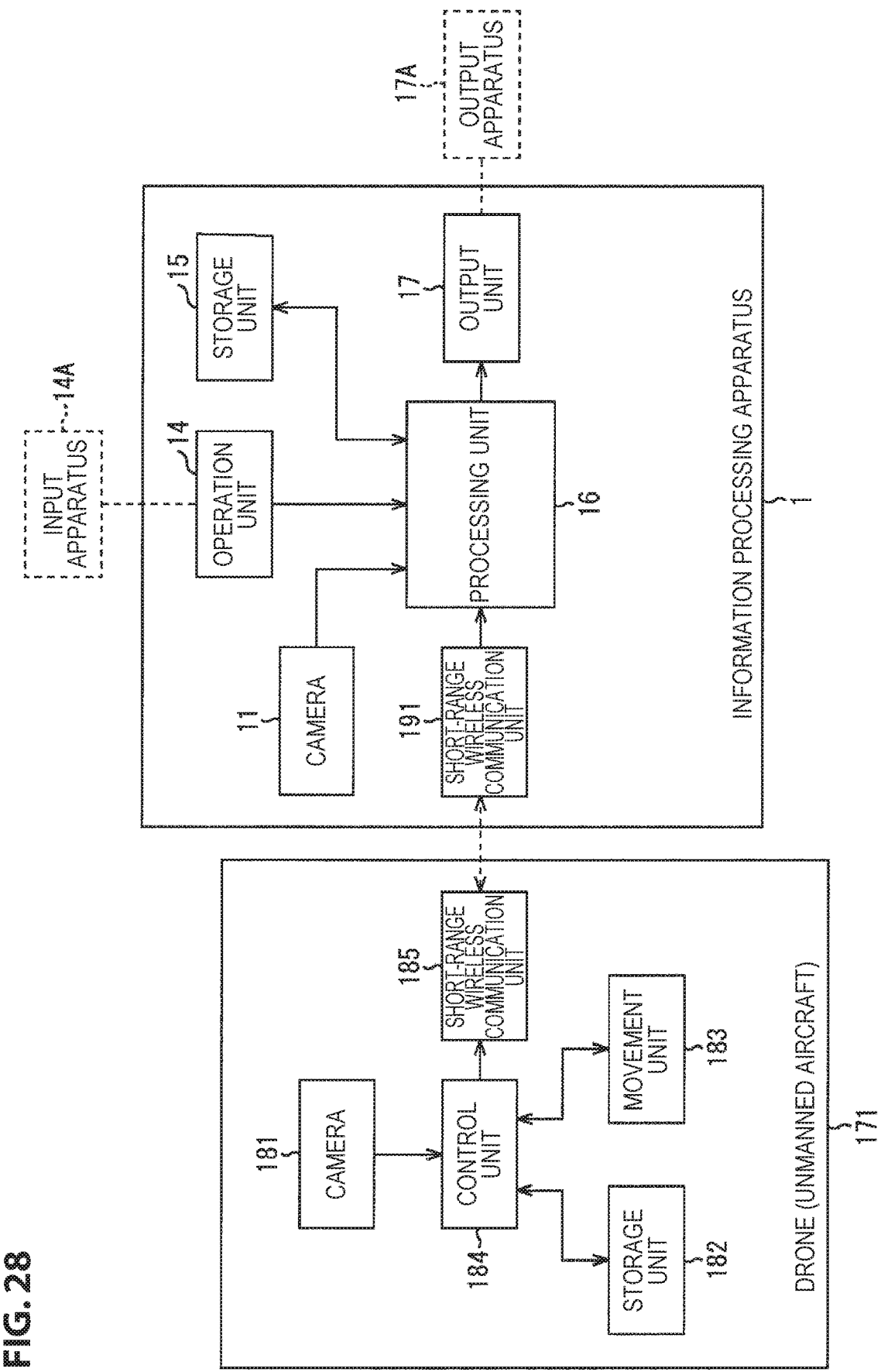
FIG. 28 is a block diagram illustrating a configuration example of the second visually impaired person walking support system.

FIG. 28 is a block diagram illustrating a configuration example of the second visually impaired person walking support system.

The second visually impaired person walking support system includes the drone 171 and the information processing apparatus 1.

The drone 171 includes a camera 181, a storage unit 182, a movement unit 183, a control unit 184 and a short-range wireless communication unit 185, and tracks a visually impaired person.

The camera 181 includes, for example, an image sensor such as a CMOS sensor or a CCD, images an object such as a crosswalk, and supplies a resultant image to the control unit 184.

The storage unit 182 includes, for example, an HDD, a semiconductor memory and the like, and stores a program to be executed in the control unit 184 and various kinds of data necessary to allow each component such as the camera 181 and the movement unit 183 to operate. In addition, the storage unit 182 stores marker information and the like for recognizing the marker 161 worn by a visually impaired person.

The movement unit 183 is a movement means for moving the drone 171 itself up, down, left, and right. For example, the movement unit 183 includes four rotor blades. The movement unit 183 moves the drone 171 itself in accordance with the control of the control unit 184.

The control unit 184 includes, for example, a CPU, an MPU and the like, and executes a predetermined program read out from the storage unit 182 to control the imaging with the camera 181 and its movement described above.

The short-range wireless communication unit 185 includes, for example, a communication device for Bluetooth (registered trademark), a wireless local area network (LAN) or the like, and transmits data such as a captured image to the information processing apparatus 1 in accordance with the control of the control unit 184.

The information processing apparatus 1 further includes a short-range wireless communication unit 191 in addition to the camera 11, the operation unit 14, the storage unit 15, the processing unit 16, and the output unit 17 described above.

The short-range wireless communication unit 191 is a communication device compliant with the short-range wireless communication unit 185 of the drone 171, and includes, for example, a communication device for Bluetooth (registered trademark), a wireless LAN or the like. The short-range wireless communication unit 191 receives data such as a captured image in accordance with the control of the processing unit 16, and supplies the received data to the processing unit 16.

<3.3 Functional Block Diagram of Processing Unit>

Figure 29:
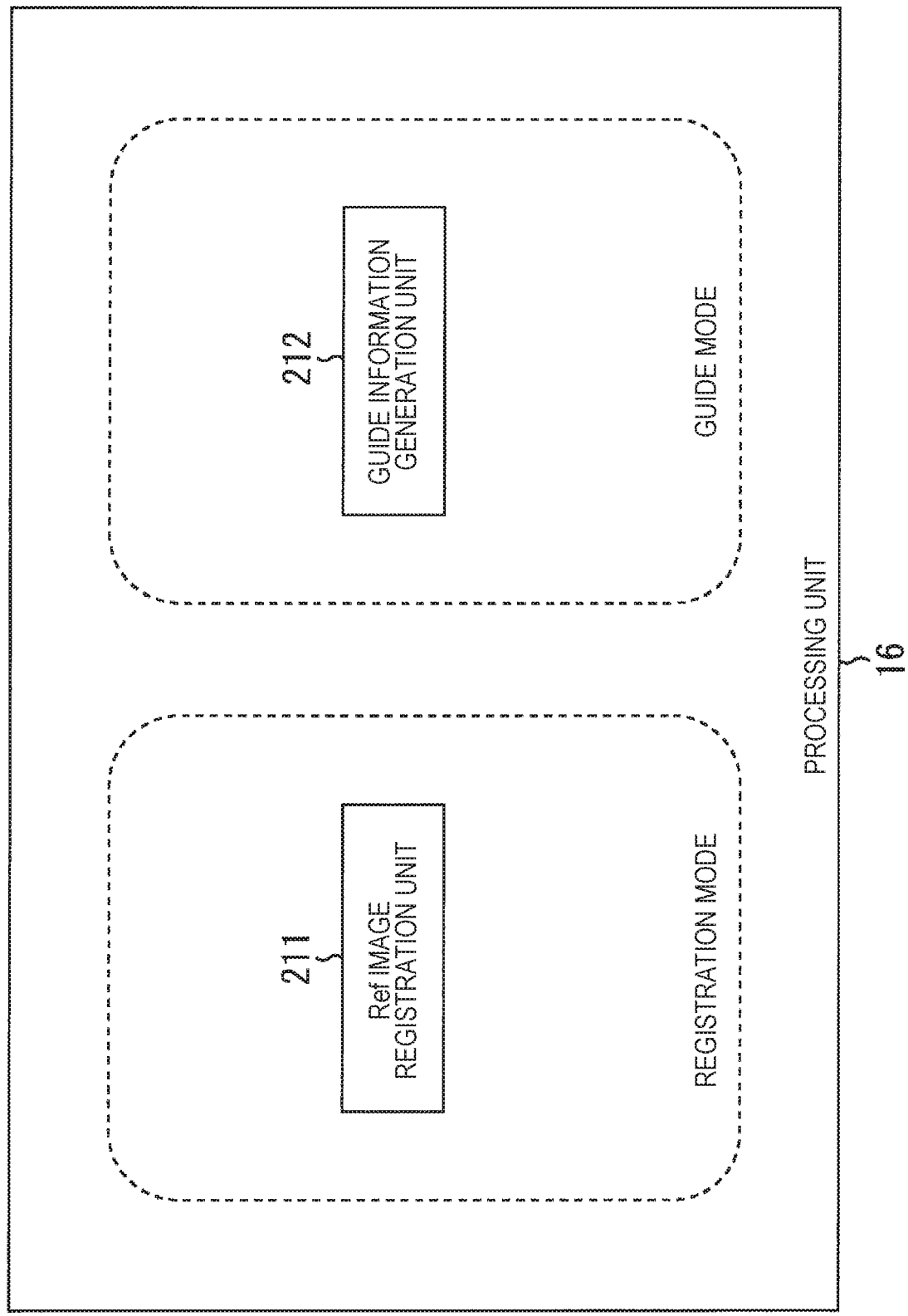
FIG. 29 is a functional block diagram of a processing unit in the second visually impaired person walking support system.

FIG. 29 is a functional block diagram of the processing unit 16 of the information processing apparatus 1 in the second visually impaired person walking support system.

The processing unit 16 includes a Ref image registration unit 211 as the registration mode.

The Ref image registration unit 211 acquires an image of a registered point (e.g., crossing point) captured from a correct place in the registration mode from the drone 171 via the short-range wireless communication unit 191. Then, the Ref image registration unit 211 registers the captured image of a registered point acquired from the drone 171 as a Ref image in the storage unit 15 (causes the storage unit 15 to store the captured image).

The Ref image registration unit 211 may be integrated with the Ref image registration unit 51 described above, or may be separate entities.

In addition, the processing unit 16 includes a guide information generation unit 212 as the guide mode. The guide information generation unit 212 recognizes the positional relationship between a visually impaired person and the drone 171, and generates guide information for guiding the visually impaired person to a correct position.

More specifically, the guide information generation unit 212 acquires an image of the current location (which will be referred to as current location image) transmitted from the drone 171 via the short-range wireless communication unit 191 in the guide mode. Then, the guide information generation unit 212 compares the current location image acquired from the drone 171 with a Ref image stored in the storage unit 15 to detect the positional deviation of a user from a correct position. Moreover, the guide information generation unit 212 generates a correction direction serving as the guide information for guiding a visually impaired person to a correct position on the basis of the detected positional deviation, and causes the generated correction direction to be output from the output unit 17 by voice.

The guide information generation unit 212 may be integrated with one or both of the direction decision unit 61 or the guide information generation unit 62 described above, or may be separate entities.

<3.4 Image Transmission Process of Drone at Time of Registration Mode>

Figure 30:
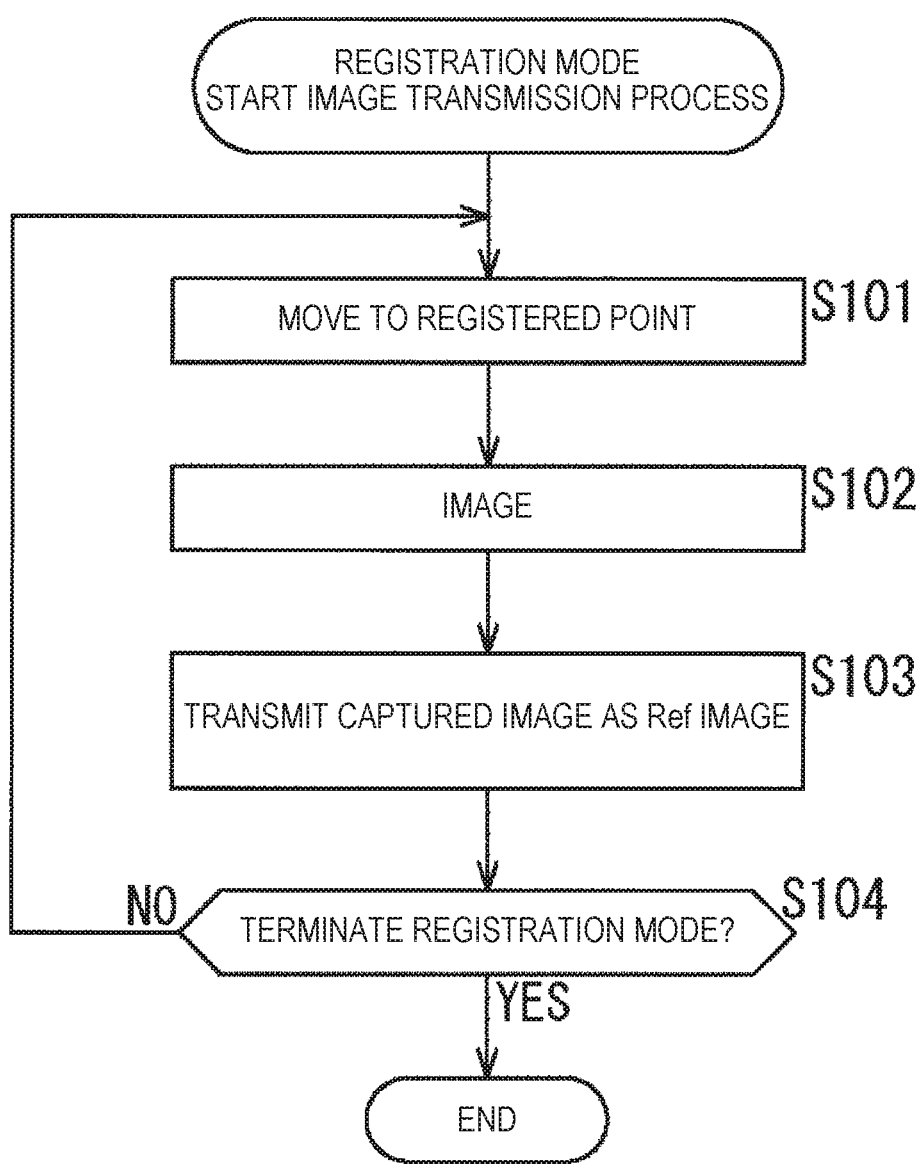
FIG. 30 is a flow chart describing an image transmission process of a drone at time of a registration mode.

Next, with reference to the flow chart of FIG. 30, an image transmission process executed by the drone 171 in the registration mode will be described.

First, in step S101, the control unit 184 controls the movement unit 183 to move to a predetermined registered point. Where to move to as a registered point may be designated, for example, via the short-range wireless communication unit 185 according to a remote operation, or movement may be autonomously performed by selecting one of a plurality of registered points that are registered in advance.

After moving to a registered point, the control unit 184 controls the camera 181, and causes the camera 181 to image the registered point in step S102. The camera 181 images the registered point in accordance with the control of the control unit 184.

In step S103, the control unit 184 transmits a captured image to the information processing apparatus 1 as a Ref image via the short-range wireless communication unit 185.

In step S104, the control unit 184 determines whether to terminate the registration mode. For example, in the case where it is determined that imaging all the registered points which are registered in advance is terminated, it is determined to terminate the registration mode.

In the case where it is determined in step S104 that the registration mode is not still terminated, the process returns to step S101, and the processes of steps S101 to S104 described above are repeated. This causes Ref images to be captured for a plurality of registered points, and to be transmitted to the information processing apparatus 1.

<3.5 Image Reception Process of Information Processing Apparatus at Time of Registration Mode>

Figure 31:
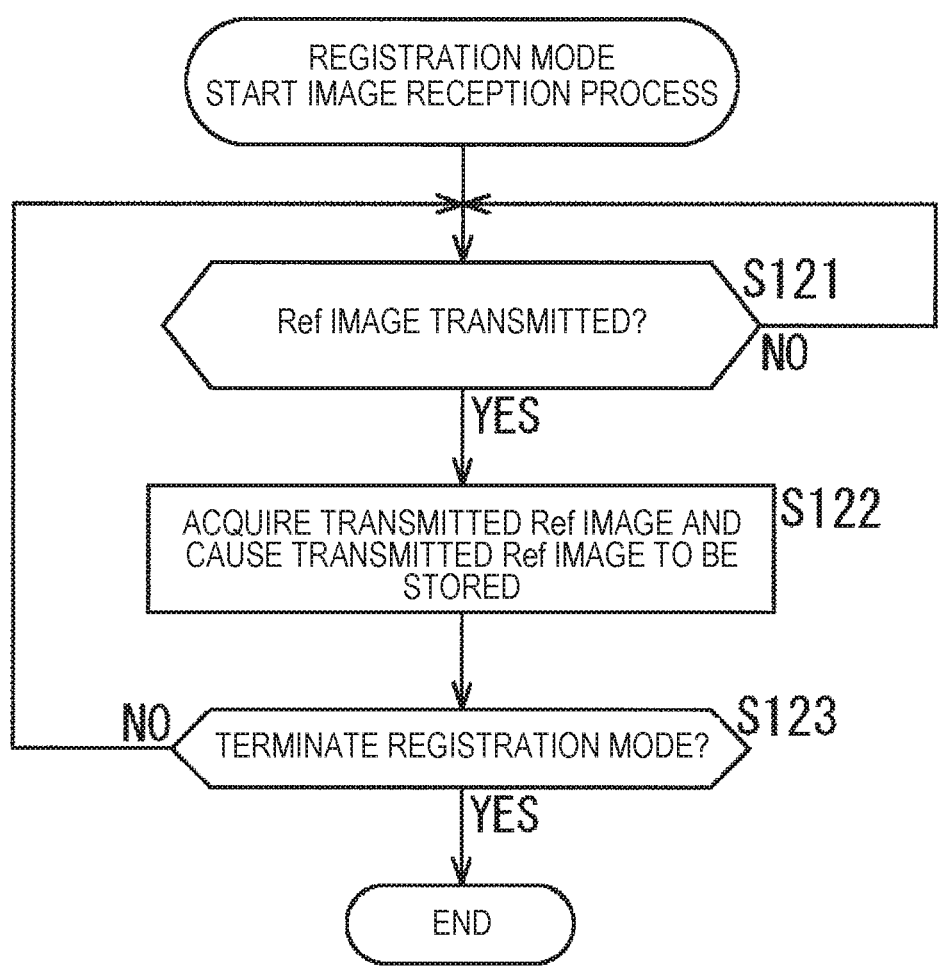
FIG. 31 is a flow chart describing an image reception process of the information processing apparatus at the time of the registration mode.

Next, with reference to the flow chart of FIG. 31, an image reception process executed by the information processing apparatus 1 in the registration mode will be described. This process is begun, for example, when the app of the Ref image registration unit 211 is executed in the registration mode.

First, in step S121, the Ref image registration unit 211 determines whether a Ref image is transmitted from the drone 171 via the short-range wireless communication unit 191, and waits until it is determined that a Ref image is transmitted.

Then, in the case where it is determined in step S121 that a Ref image is transmitted, the process proceeds to step S122, and the Ref image registration unit 211 acquires the transmitted Ref image and causes the storage unit 15 to store the acquired Ref image.

In step S123, the Ref image registration unit 211 determines whether to terminate the registration mode. For example, in the case where an operation of terminating the app of the Ref image registration unit 211 is performed, it is determined to terminate the registration mode.

In the case where it is determined in step S123 that the registration mode is not still terminated, the process returns to step S121, and the processes of steps S121 to S123 described above are repeated. This causes Ref images regarding a plurality of registered points to be acquired, and to be stored in the storage unit 15.

<3.6 Image Transmission Process of Drone at Time of Guide Mode>

Figure 32:
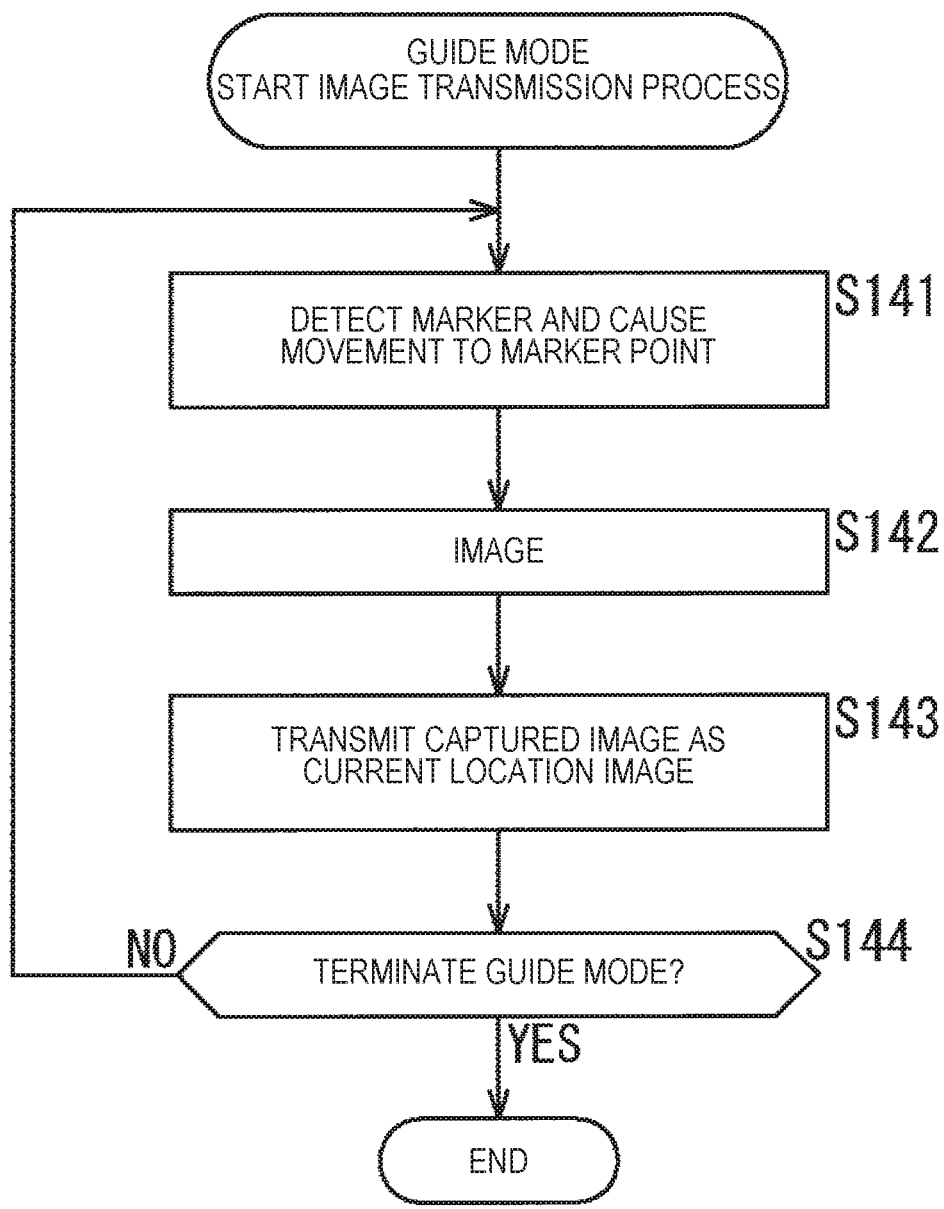
FIG. 32 is a flow chart describing an image transmission process of the drone at time of a guide mode.

Next, with reference to the flow chart of FIG. 32, an image transmission process executed by the drone 171 in the guide mode will be described.

First, in step S141, the control unit 184 detects the marker 161 worn by a visually impaired person from an image captured by the camera 181, and causes the movement unit 183 to move the detected marker 161 such that the detected marker 161 is located at the position right below the control unit 184 itself.

After moving right below the marker 161, the control unit 184 controls the camera 181, and causes the camera 181 to image the area right below in step S142. The camera 181 images the area right below in accordance with the control of the control unit 184.

In step S143, the control unit 184 transmits a captured image to the information processing apparatus 1 via the short-range wireless communication unit 185 as a current location image indicating the current location of a visually impaired person.

In step S144, the control unit 184 determines whether to terminate the guide mode. For example, when a notification indicating that the guide mode is terminated is issued from the information processing apparatus 1 through short-range wireless communication, it is determined to terminate the registration mode.

In the case where it is determined in step S144 that the guide mode is not still terminated, the process returns to step S141, and the processes of steps S141 to S144 described above are repeated. With this arrangement, a moving visually impaired person is tracked, and an image showing the visually impaired person from the right above is periodically transmitted to the information processing apparatus 1 as a current location image.

<3.7 Image Reception Process of Information Processing Apparatus at Time of Guide Mode>

Figure 33:
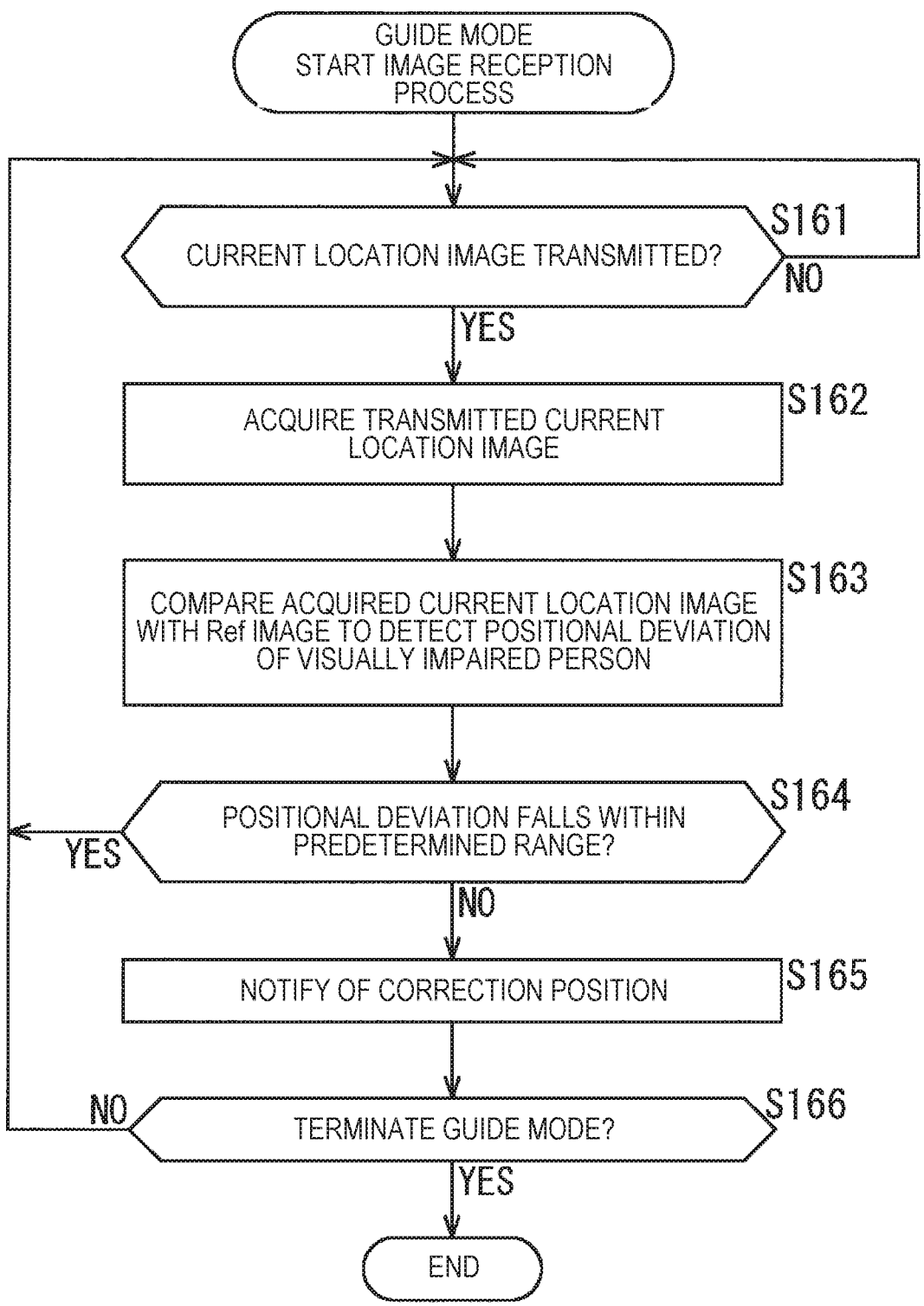
FIG. 33 is a flow chart describing an image reception process of the information processing apparatus at the time of the guide mode.

Next, with reference to the flow chart of FIG. 33, an image reception process executed by the information processing apparatus 1 in the guide mode will be described. This process is begun, for example, when the app of the guide information generation unit 212 is executed in the guide mode.

First, in step S161, the guide information generation unit 212 determines whether a current location image is transmitted from the drone 171 via the short-range wireless communication unit 191, and waits until it is determined that a current location image is transmitted.

Then, in the case where it is determined in step S161 that a current location image is transmitted, the process proceeds to step S162, and the guide information generation unit 212 acquires the transmitted current location image.

In step S163, the guide information generation unit 212 compares the acquired current location image with a Ref image stored in the storage unit 15 to detect the positional deviation of the visually impaired person from a registered point. For example, the guide information generation unit 212 detects the central area of a Ref image from a current location image in accordance with pattern matching, and detects the positional deviation between the detected position and the center of the image.

In step S164, the guide information generation unit 212 determines whether the detected positional deviation falls within a predetermined range that is defined in advance. In the case where it is determined that the detected positional deviation falls within the predetermined range, the process is returned to step S161.

In contrast, in the case where it is determined in step S164 that the detected positional deviation does not fall within the predetermined range that is defined in advance, the process proceeds to step S165, and the guide information generation unit 212 causes the output unit 17 to output the voice message of "right" or "left" which serves as guide information, and notifies the visually impaired person of a correction direction.

In step S166, the guide information generation unit 212 determines whether to terminate the guide mode. For example, in the case where an operation of terminating the app of the guide information generation unit 212 is performed, it is determined to terminate the guide mode.

In the case where it is determined in step S166 that the guide mode is not still terminated, the process returns to step S161, and the processes of steps S161 to S166 described above are repeated. This causes a current location image regarding each of a plurality of registered points to be acquired and compared with a Ref image, and the visually impaired person is notified of guide information.

According to the second visually impaired person walking support system described above, the current position of a visually impaired person is detected on the basis of an image captured by the drone 171 and a deviation from the current positional deviation is calculated, and the visually impaired person can be notified of it as guide information.

<3.8 Modification of Second Visually Impaired Person Walking Support System>

Figure 34A:
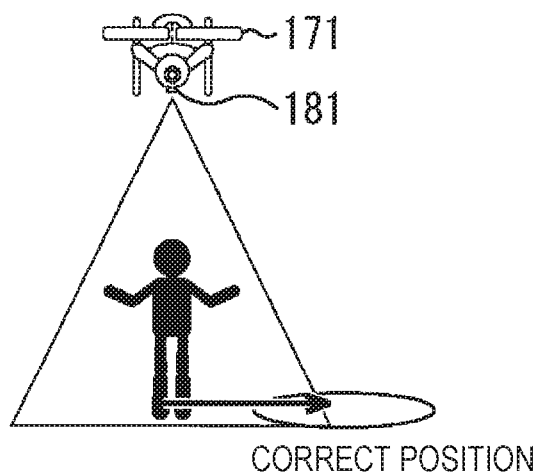
FIGS. 34A and 34B is a are diagrams illustrating a modification of the second visually impaired person walking support system.

Note that, in the embodiment of the second visually impaired person walking support system described above, as illustrated in of FIG. 34A, the drone 171 moves right above a visually impaired person, and the camera 181 images the visually impaired person right below.

Figure 34B:
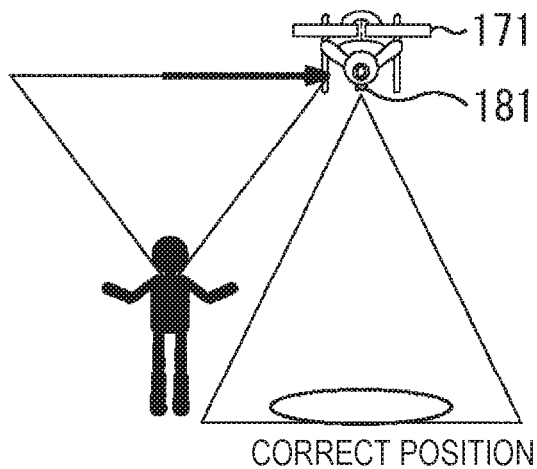

However, as illustrated in FIG. 34B, while the drone 171 moves to a correct position, the camera 181 may include a visually impaired person in the field of view, and a positional deviation of the visually impaired person may be detected as a deviation from the center of the captured current location image.

In addition, in the case where the drone 171 moves to a correct position, the camera 11 of the information processing apparatus 1 worn by a visually impaired person may image the drone 171, and detect a positional deviation of the visually impaired person on the basis of the detected position of the drone 171.

Figure 35A:
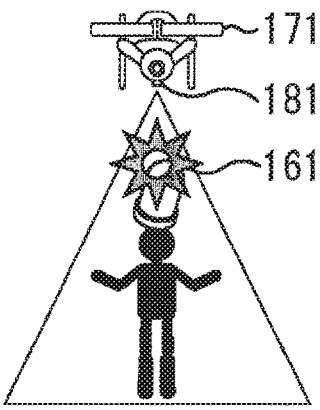
FIGS. 35A, 35B, and 35C is a are diagrams illustrating another example of a marker.
Figure 35B:
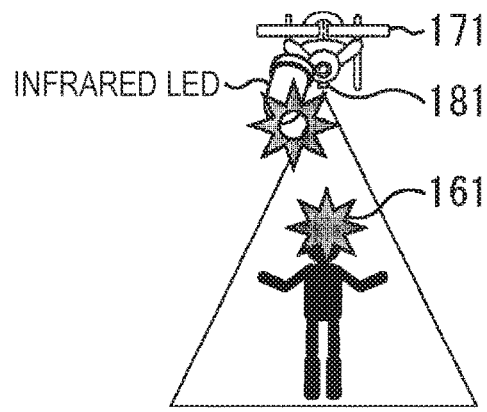
Figure 35C:
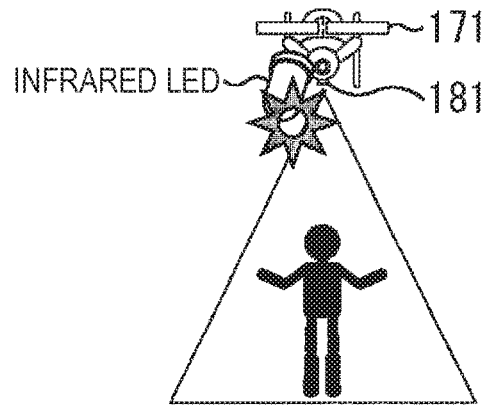

FIGS. 35A, 35B, and 35C illustrate another example of the marker 161 for reducing erroneous recognition.

The example described above adopts a two-dimensional code as the marker 161, but, as illustrated in FIG. 35A, the marker 161 may be an infrared LED that emits infrared light and the camera 181 of the drone 171 may be an infrared camera.

In addition, illustrated in FIG. 35B, the drone 171 may include an infrared LED to emit infrared light, the camera 181 of the drone 171 may serve as an infrared camera, and the marker 161 worn by a visually impaired person may be an infrared reflector.

Alternatively, as illustrated in FIG. 35C, the drone 171 may include an infrared LED to emit infrared light, the camera 181 of the drone 171 may serve as an infrared camera, and the position of a visually impaired person may be detected in accordance with image recognition.

In addition, the camera 181 included in the drone 171 may be a camera such as a structured light camera, a Time-of-Flight (ToF) camera, or a stereo camera that can detect the depth direction.

In the example described above, the positional deviation of the current location of a visually impaired person is detected on the basis of a Ref image captured in advance in the registration mode, but map information may be compared with a current location image to detect the positional deviation of the current location.

In the example described above, all the images captured by the drone 171 are transferred to the information processing apparatus 1, and the information processing apparatus 1 side detects the positional deviation of the current location of a visually impaired person. However, an image captured by the drone 171 may be stored in the storage unit 182, the drone 171 may detect a positional deviation according to a comparison with a current location image in the guide mode, and deviation information alone which indicates a detection result may be transmitted to the information processing apparatus 1.

<4. External Appearance Example of Smartphone Cover>
<4.1 External Appearance Example of Smartphone Cover>

Next, an embodiment of a smartphone cover will be described.

A smartphone including a touch panel is designed on the condition of visual information on the screen. The operation screen is also flat, so that it is difficult for a visually impaired person to recognize where an operation button and the like are disposed on the screen, and a visually impaired person is confronted with difficulty in operation.

Then, the following describes an embodiment of a smartphone cover that makes a smartphone favorable for a visually impaired person.

Figure 36:
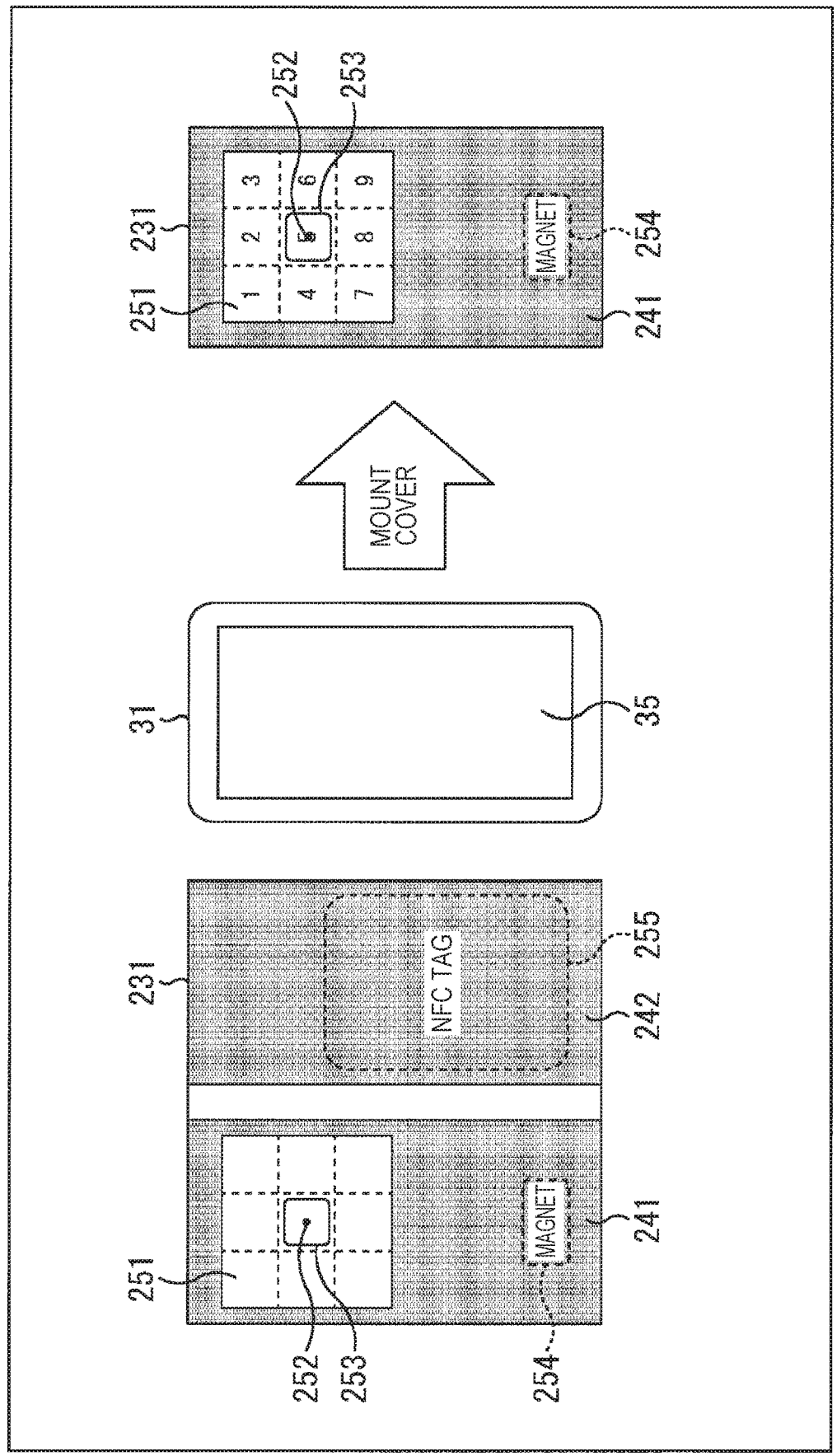
FIG. 36 is a diagram describing an external appearance example of a smartphone cover.

FIG. 36 is a diagram describing an external appearance example of the smartphone cover.

A smartphone cover 231 illustrated in FIG. 36 includes a front face cover 241 that protects a display 35 of a smartphone 31, and a back face cover 242 that protects the surface opposite to the display 35 side.

A small window 251 including a transmissive material such as plastic is disposed on the front face cover 241. The small window 251 allows a visually impaired person to perform a touch operation on a predetermined area of the display 35. A seal 253 is pasted to the small window 251. A protrusion 252 representing a reference position is formed on the central divided area of the seal 253 among nine divided areas obtained by dividing the open area into 3×3 (i.e., nine).

In addition, a magnet 254 is embedded in a predetermined area of the front face cover 241 which is different from the area on which the small window 251 is disposed.

Meanwhile, an NFC tag 255 including an IC chip and an antenna that perform near field communication (NFC) communication is embedded in the cover in the back face cover 242.

When the smartphone cover 231 is mounted on the smartphone 31, the smartphone 31 detects the magnet 254 embedded in the front face cover 241 to detect that the smartphone cover 231 is mounted.

In the case where the smartphone 31 detects that the smartphone cover 231 is mounted, the smartphone 31 switches the operation mode to a user interface dedicated to the visually impaired (which will be referred to as grid mode below) in which only the open area of the small window 251 on the front face cover 241 serves as an operation area.

In the grid mode, nine UI buttons are disposed as 3×3 disposition in the areas of the display 35 corresponding to the nine respective divided areas of the small window 251 on the front face cover 241. The UI buttons correspond to apps that execute a variety of functions of the smartphone 31. A visually impaired person has recognized what app is allocated to each of the nine UI buttons, and can select a desired UI button to start the app by easily recognizing the nine divided areas by using the protrusion 252 of the seal 253 bonded to the small window 251 as a reference position.

In addition, in the grid mode, when a predetermined UI button is touched, an audio reading function of reading the touched app or function by voice is enabled.

Note that, in the present embodiment, the seal 253 on which the protrusion 252 is formed is pasted to the small window 251 to form the protrusion 252, but the protrusion 252 may be directly molded on the small window 251.

<4.2 Block Diagram>

Figure 37:
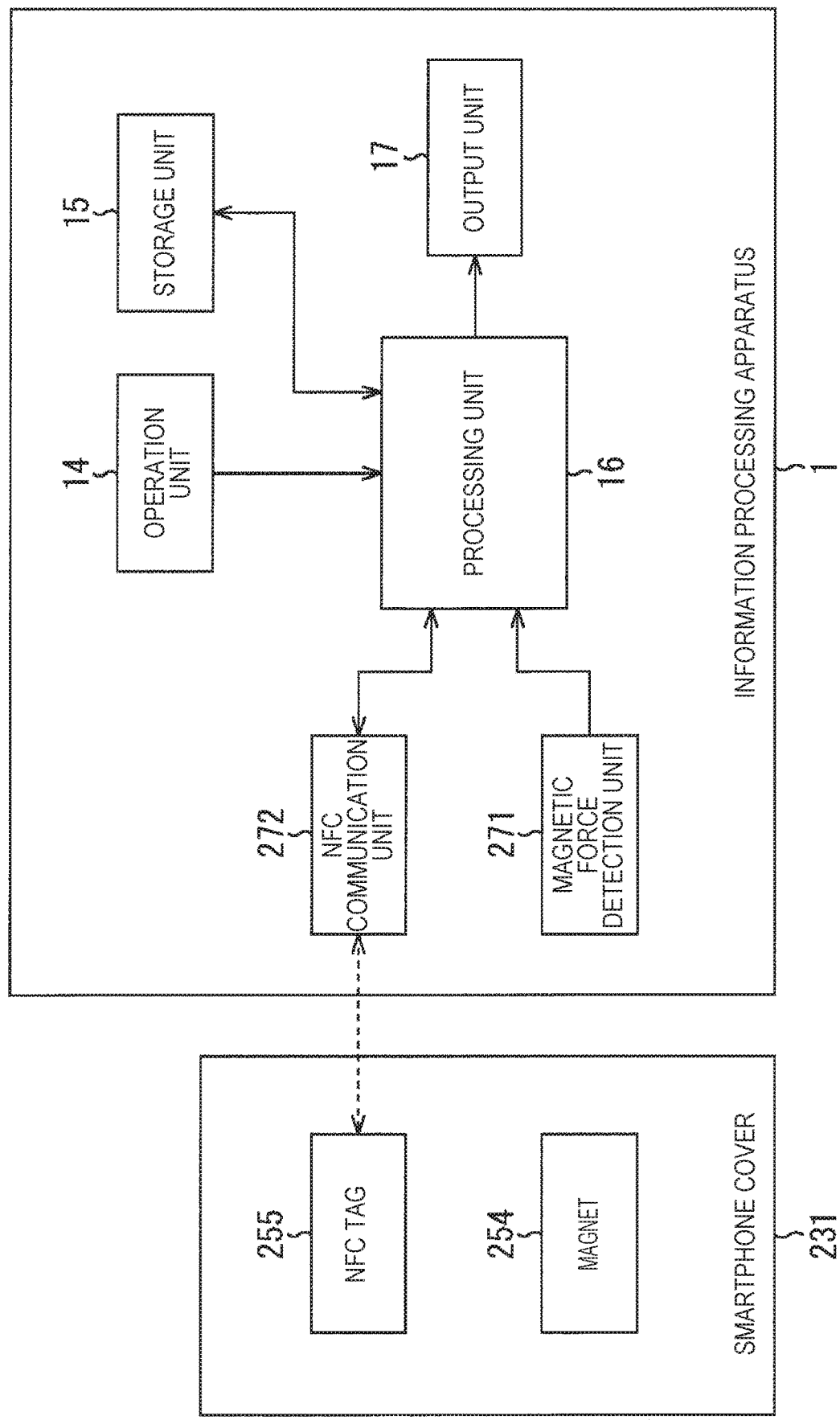
FIG. 37 is a block diagram regarding a UI operation of the information processing apparatus in cooperation with the smartphone cover.

FIG. 37 is a block diagram regarding a UI operation of the smartphone cover 231 and the information processing apparatus 1 serving as the smartphone 31.

Note that, in the configuration of the information processing apparatus 1 in FIG. 37, only minimum components necessary to perform a process cooperated with the smartphone cover 231 are illustrated. Thus, in the case where the information processing apparatus 1 serving as the smartphone 31 also includes the crosswalk walking guide function and other functions described above, the information processing apparatus 1 also includes components necessary to execute the functions.

The smartphone cover 231 includes the magnet 254 and an NFC tag 255.

The information processing apparatus 1 includes a magnetic force detection unit 271 and an NFC communication unit 272 in addition to the operation unit 14, the storage unit 15, the processing unit 16, and the output unit 17.

The NFC tag 255 is a communication device that performs near field communication according to ISO/IEC 18092 or ISO/IEC 14443. The NFC tag 255 stores UI disposition information in the internal memory. The UI disposition information includes UI button coordinate information that indicates the disposition (coordinate position) of the UI buttons, and UI button definition information that defines the UI buttons disposed in the 3×3 (i.e., nine) divided areas. In addition, the NFC tag 255 also stores NFC tag identification information for identifying the NFC tag 255 itself (each NFC tag for a reader/writer) in the internal memory.

In the case where the NFC communication unit 272 of the information processing apparatus 1 is brought closer, the NFC tag 255 transmits the UI disposition information to the NFC communication unit 272 through near field communication.

The magnetic force detection unit 271 detects the magnet 254 to detect whether or not the front face cover 241 of the smartphone cover 231 is closed, and supplies a detection result to the processing unit 16.

The NFC communication unit 272 is an NFC device serving as a reader/writer that performs near field communication with the NFC tag 255 according to ISO/IEC 18092 or ISO/IEC 14443. The NFC communication unit 272 supplies electromagnetic waves to the NFC tag 255 to supply a power source, and acquires (receives) the UI disposition information stored in the NFC tag 255 to supply the acquired (received) UI disposition information to the processing unit 16.

In the case where the NFC communication unit 272 detects the NFC tag 255 that is brought closer, the NFC communication unit 272 acquires NFC tag identification information. This acquired NFC tag identification information makes it possible to identify the type of the smartphone cover 231.

In the case where the fact that the front face cover 241 of the smartphone cover 231 is closed is supplied from the magnetic force detection unit 271, the processing unit 16 causes the NFC communication unit 272 to acquire the UI disposition information from the NFC tag 255 of the smartphone cover 231. Then, the processing unit 16 switches the display of a display that is a part of the output unit 17 to the grid mode corresponding to the open area of the small window 251 on the smartphone cover 231 in accordance with the UI disposition information acquired by the NFC communication unit 272. Thus, the processing unit 16 functions as a display control unit that switches the display of the display in accordance with whether or not the front face cover 241 is closed.

In addition, in the case where the display of the output unit 17 is an LCD, the processing unit 16 can also set off the back light to reduce power consumption when the grid mode dedicated to the visually impaired is set.

<4.3 Cover Close Detection Process>

Next, with reference to the flow chart of FIG. 38, a cover close detection process will be described that is a process in which the information processing apparatus 1 serving as the smartphone 31 detects that the front face cover 241 is closed and executes a predetermined process. This process is begun, for example, when the information processing apparatus 1 is powered on.

First, in step S201, the processing unit 16 determines, on the basis of a detection result of the magnetic force detection unit 271, whether or not the front face cover 241 is closed, and waits until it is determined that the front face cover 241 is closed.

Then, in the case where it is determined in step S201 that the front face cover 241 is closed, the process proceeds to step S202, and the processing unit 16 causes the NFC communication unit 272 to detect the NFC tag 255 of the mounted smartphone cover 231.

In step S203, the NFC communication unit 272 detects the NFC tag 255 in accordance with the control of the processing unit 16, and acquires the UI disposition information from the NFC tag 255. The acquired UI disposition information is supplied to the processing unit 16.

In step S204, the processing unit 16 switches the display of a display that is a part of the output unit 17 to the grid mode corresponding to the open area of the small window 251 on the smartphone cover 231 in accordance with the acquired UI disposition information. In the grid mode, the nine UI buttons defined in accordance with the UI button definition information are disposed in the areas of the display 35 corresponding to the open area of the small window 251 on the front face cover 241 in accordance with the UI disposition information acquired from the smartphone cover 231.

In step S205, the processing unit 16 executes a registration app execution operation detection process of detecting whether or not an operation of executing any of the apps (which will be referred to as registration apps below) allocated to the UI buttons disposed in the grid mode is performed. The details of this process will be described below with reference to FIG. 40 and the like. However, according to this process, it is determined whether or not an execution operation of a registration app is performed.

In step S206, the processing unit 16 determines whether an execution operation of a registration app is detected as a result of the registration app execution operation detection process.

In the case where it is determined in step S206 that an execution operation of a registration app is not detected, the process is returned to step S205, and the registration app execution operation detection process is executed again. That is, the processing unit 16 waits until it is determined that an execution operation of a registration app is detected.

Then, in the case where it is determined in step S206 that an execution operation of a registration app is detected, the process proceeds to step S207, and the processing unit 16 starts the registration app for which the execution operation is detected. The started registration app is executed in parallel with the cover close detection process.

After a registration app is started in step S207, the process is returned to step S205, and the registration app execution operation detection process is executed again. Thus, the processing unit 16 waits again until it is determined that an execution operation of a registration app is detected.

<4.4 Cover Open Detection Process>

Next, with reference to the flow chart of FIG. 39, a cover open detection process will be described that is a process in which the information processing apparatus 1 serving as the smartphone 31 detects that the front face cover 241 is opened and executes a predetermined process. This process is begun, for example, when the cover close detection process in FIG. 38 is executed, and executed in parallel with the cover close detection process.

First, in step S221, the processing unit 16 determines, on the basis of a detection result of the magnetic force detection unit 271, whether or not the front face cover 241 is opened, and waits until it is determined that the front face cover 241 is opened.

Then, in the case where it is determined in step S221 that the front face cover 241 is opened, the process proceeds to step S222, and the processing unit 16 terminates the grid mode of the display and terminates the cover open detection process.

According to the cover close detection process and the cover open detection process described above, the information processing apparatus 1 detects that the front face cover 241 of the smartphone cover 231 is closed, and automatically begins the grid mode that is easy for the visually impaired to operate. When detecting that the front face cover 241 is opened, the information processing apparatus 1 automatically terminates the grid mode. This makes it possible to automatically allocate a necessary UI button without a user setting, and allows a visually impaired person to easily start and operate an app. In addition, in the case where it is detected that the front face cover 241 is closed, a guide app for executing the crosswalk guide process or the checkpoint guide reproduction process may be started.

<4.5 Registration App Execution Operation Detection Process>

Figure 40:
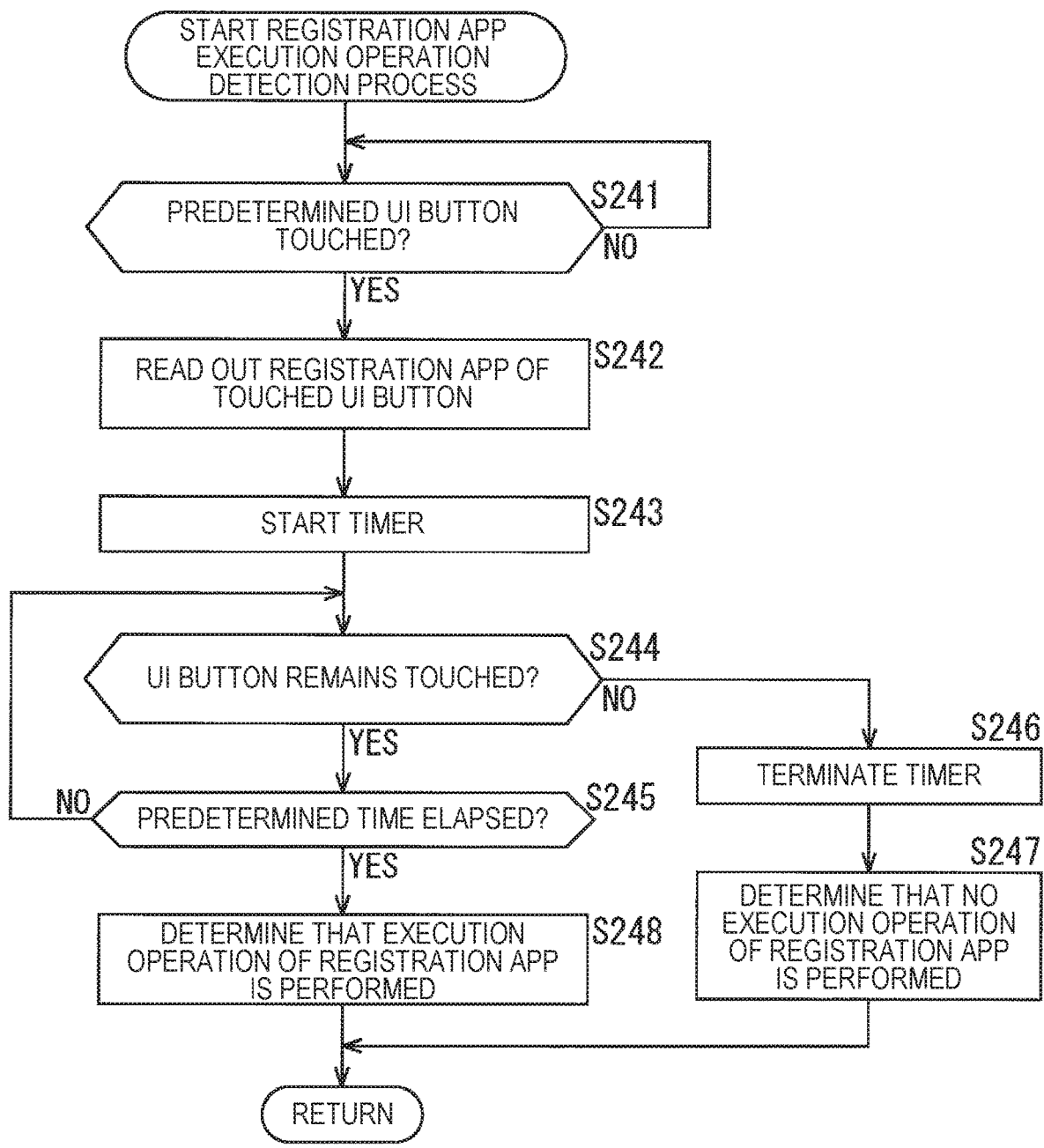
FIG. 40 is a flow chart describing a registration app execution operation detection process of step S205 in FIG. 38.

Next, with reference to the flow chart of FIG. 40, the details of the registration app execution operation detection process executed in step S205 of FIG. 38 will be described.

First, in step S241, the processing unit 16 determines whether a predetermined UI button disposed in the grid mode is touched, and waits until it is determined a predetermined UI button is touched.

In the case where it is determined in step S241 that a predetermined UI button is touched, the process proceeds to step S242, and the processing unit 16 controls a speaker that is a part of the output unit 17 and reads the registration app allocated to the touched UI button.

In step S243, the processing unit 16 starts a timer for counting the time elapsed since the UI button is touched.

In step S244, the processing unit 16 determines whether the UI button touch on which is detected in step S241 remains touched.

In the case where it is determined in step S244 that the UI button remains touched, the process proceeds to step S245, and it is determined whether a predetermined time elapses. Then, in the case where it is determined in step S245 that the predetermined time has not yet elapsed, the process is returned to step S244. Thus, it is determined in step S244 whether the UI button touch on which is detected in step S241 remains touched for a predetermined time that is decided in advance.

In the case where it is determined in step S244 that the touched UI button is no longer touched before the predetermined time elapses, the process proceeds to step S246, and the processing unit 16 terminates the timer started in step S243.

Figure 38:
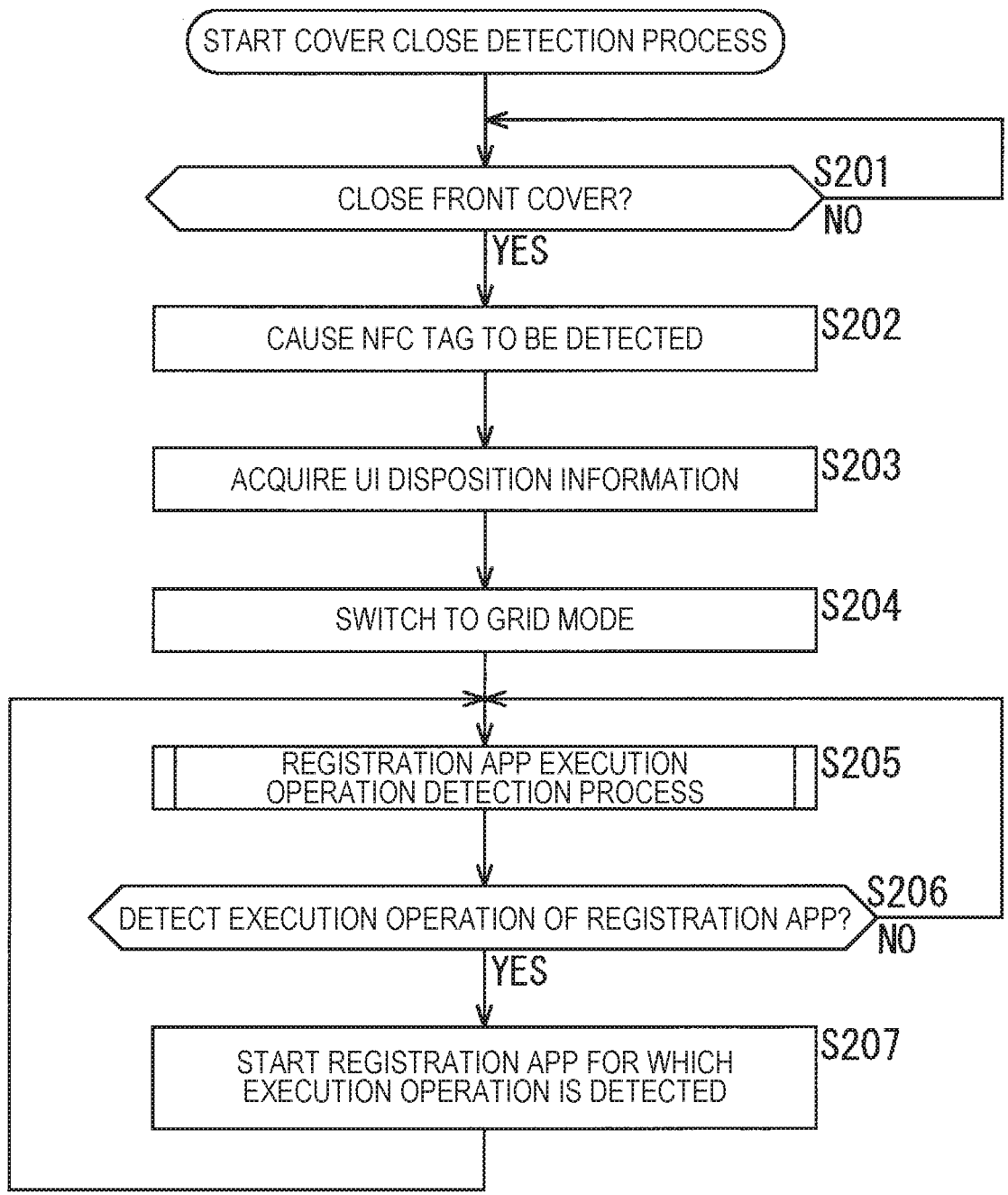
FIG. 38 is a flow chart describing a cover close detection process.
Figure 39:
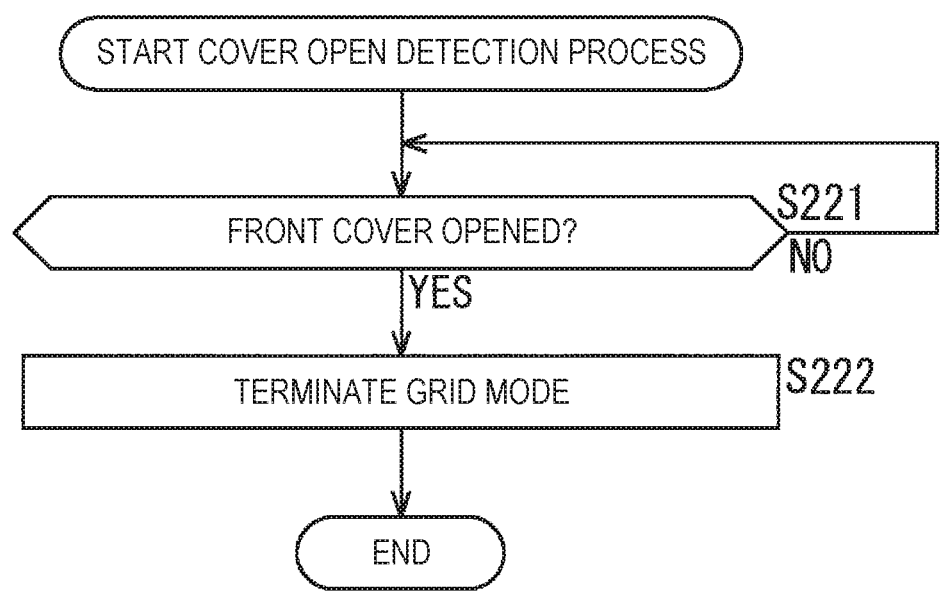
FIG. 39 is a flow chart describing a cover open detection process.

Then, in step S247, the processing unit 16 determines that no execution operation of a registration app is performed, terminates the registration app execution operation detection process, and returns the process to the cover close detection process in FIG. 38.

In contrast, in the case where it is determined in step S245 that the UI button touch on which is detected in step S241 remains touched and the predetermined time elapses, the process proceeds to step S248, and the processing unit 16 determines that an execution operation of a registration app is performed, terminates the registration app execution operation detection process, and returns the process to the cover close detection process in FIG. 38.

According to the registration app execution operation detection process described above, in the case where a predetermined UI button is not only simply touched, but remains touched for a predetermined time, it is determined that a visually impaired person performs an execution operation of a sense-of-sight registration app. This can prevent a visually impaired person from performing an erroneous operation of a touch operation.

Note that, in the case where a double tapping operation is detected instead of a so-called holding operation as described above, it may be determined that an execution operation of the sense-of-sight registration app is performed. Even in this case, it is possible to prevent a visually impaired person from performing an erroneous operation of a touch operation.

<4.6 Another Example of Registration App Execution Operation Detection Process>

Another example of the registration app execution operation detection process for preventing a visually impaired person from performing an erroneous operation of a touch operation will be described.

Figure 41:
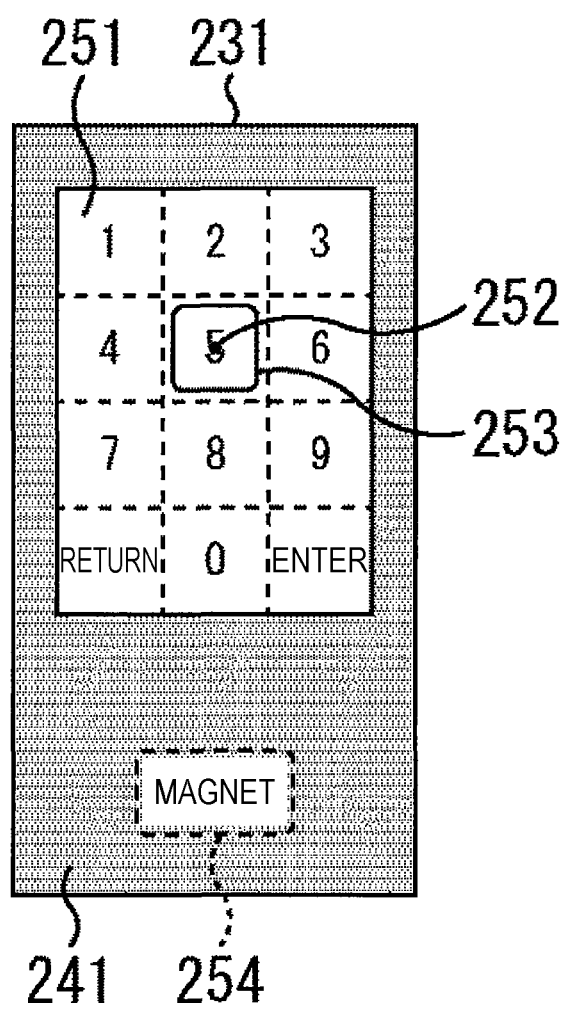
FIG. 41 is a diagram illustrating another display example of a grid mode.

FIG. 41 is a diagram illustrating another display example at the time of the grid mode.

In the example described above, when the grid mode is begun, a registration app is allocated to each of the 3×3 (i.e., nine) divided areas displayed in the open area of the small window 251 on the front face cover 241. In the next example, as illustrated in FIG. 41, 3×4 (i.e., twelve) divided areas are formed in association with the open area of the small window 251. Registration apps are allocated to ten divided areas, but a "return" button and a "enter" button are allocated to the two remaining divided areas (e.g., lower left corner position and lower right corner position in the example of FIG. 41). In this way, 3×3 (i.e., nine) divided areas may be disposed, or 3×4 (i.e., twelve) divided areas may be disposed in the open area of the small window 251.

Figure 42:
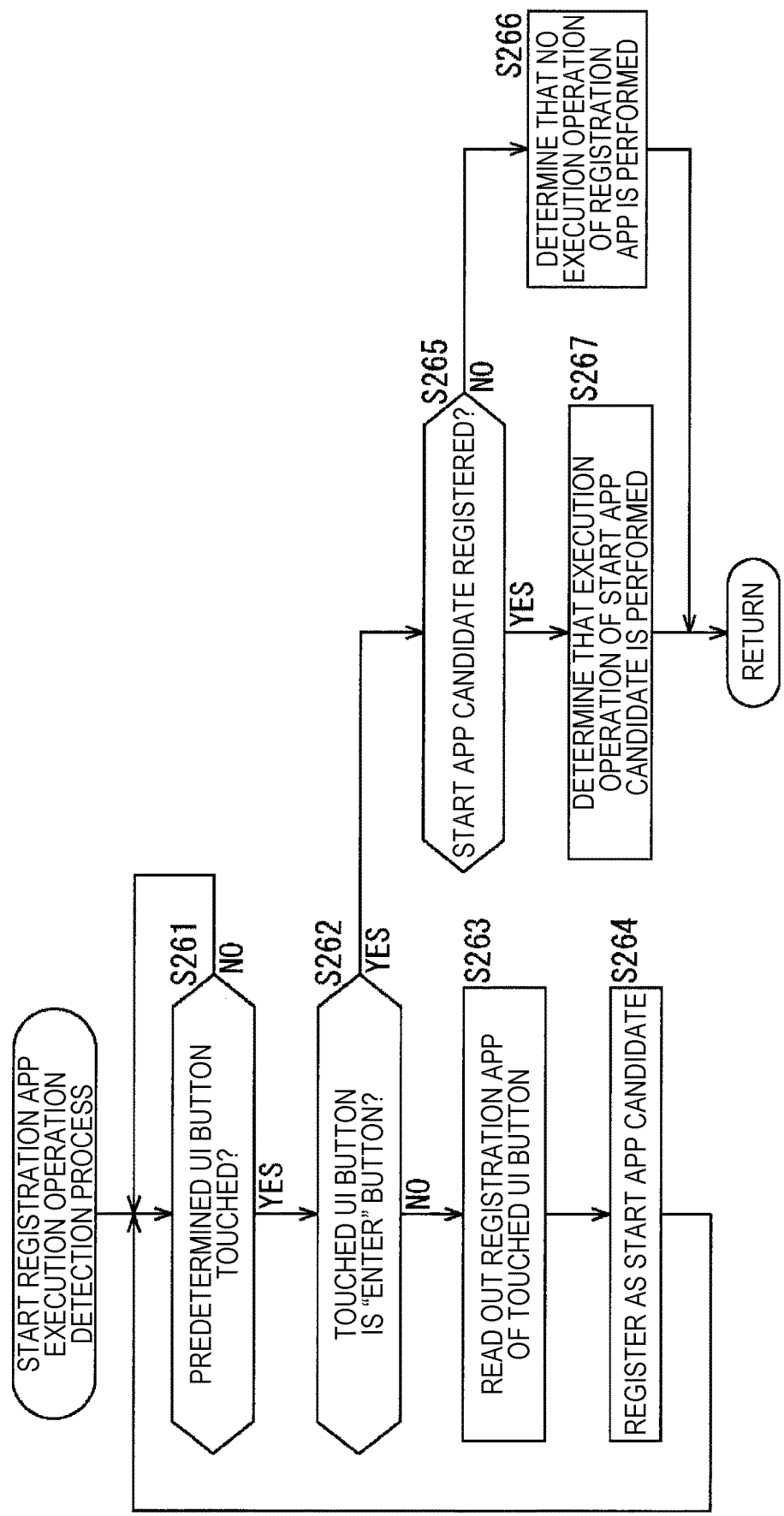
FIG. 42 is a flow chart describing a registration app execution operation detection process at time of the grid mode of FIG. 41.

FIG. 42 illustrates a flow chart of the registration app execution operation detection process in the case of the display illustrated in FIG. 41 at the time of the grid mode.

First, in step S261, the processing unit 16 determines whether a predetermined UI button disposed in the grid mode is touched, and waits until it is determined a predetermined UI button is touched.

In the case where it is determined in step S261 that a predetermined UI button is touched, the process proceeds to step S262, and the processing unit 16 determines whether the touched UI button is an "enter" button.

In the case where it is determined in step S262 that a touched UI button is not an "enter" button, the process proceeds to step S263, and the processing unit 16 controls a speaker that is a part of the output unit 17 and reads the registration app allocated to the touched UI button.

Moreover, in step S264, the processing unit 16 registers the registration app of the touched UI button as a start app candidate. In the case where the UI button to which the registration app is allocated should be repeatedly touched, the registered start app candidate is overwritten, and only information of the registration app that is touched for the last time is stored as a start app candidate. After step S264, the process is returned to step S261.

In contrast, in the case where it is determined in step S262 that the touched UI button is an "enter" button, the process proceeds to step S265, and the processing unit 16 determines whether a start app candidate is registered.

In the case where it is determined in step S265 that a start app candidate is not registered, the process proceeds to step S266, and the processing unit 16 determines that no execution operation of a registration app is performed and terminates the registration app execution operation detection process to return the process to the cover close detection process in FIG. 38.

In contrast, in the case where it is determined in step S265 that a start app candidate is registered, the process proceeds to step S267, and the processing unit 16 determines that an execution operation of a registration app is performed and terminates the registration app execution operation detection process to return the process to the cover close detection process in FIG. 38. In step S207 of FIG. 38, the registered start app candidate is started.

In the case where an enter button is disposed in one of the divided areas in the grid mode in the information processing apparatus 1, the registration app execution operation detection process described above is executed to prevent a visually impaired person from performing an erroneous operation of a touch operation and make it possible to start a desired registration app.

<4.7 Another Example of Seal Pasted to Small Window>

The seal 253 including the protrusion 252 is pasted to the central part of the small window 251 on the front face cover 241 of the smartphone cover 231 illustrated in FIG. 36 to allow a visually impaired person to recognize the disposition of 3×3 (i.e., nine) UI buttons.

Figure 43:
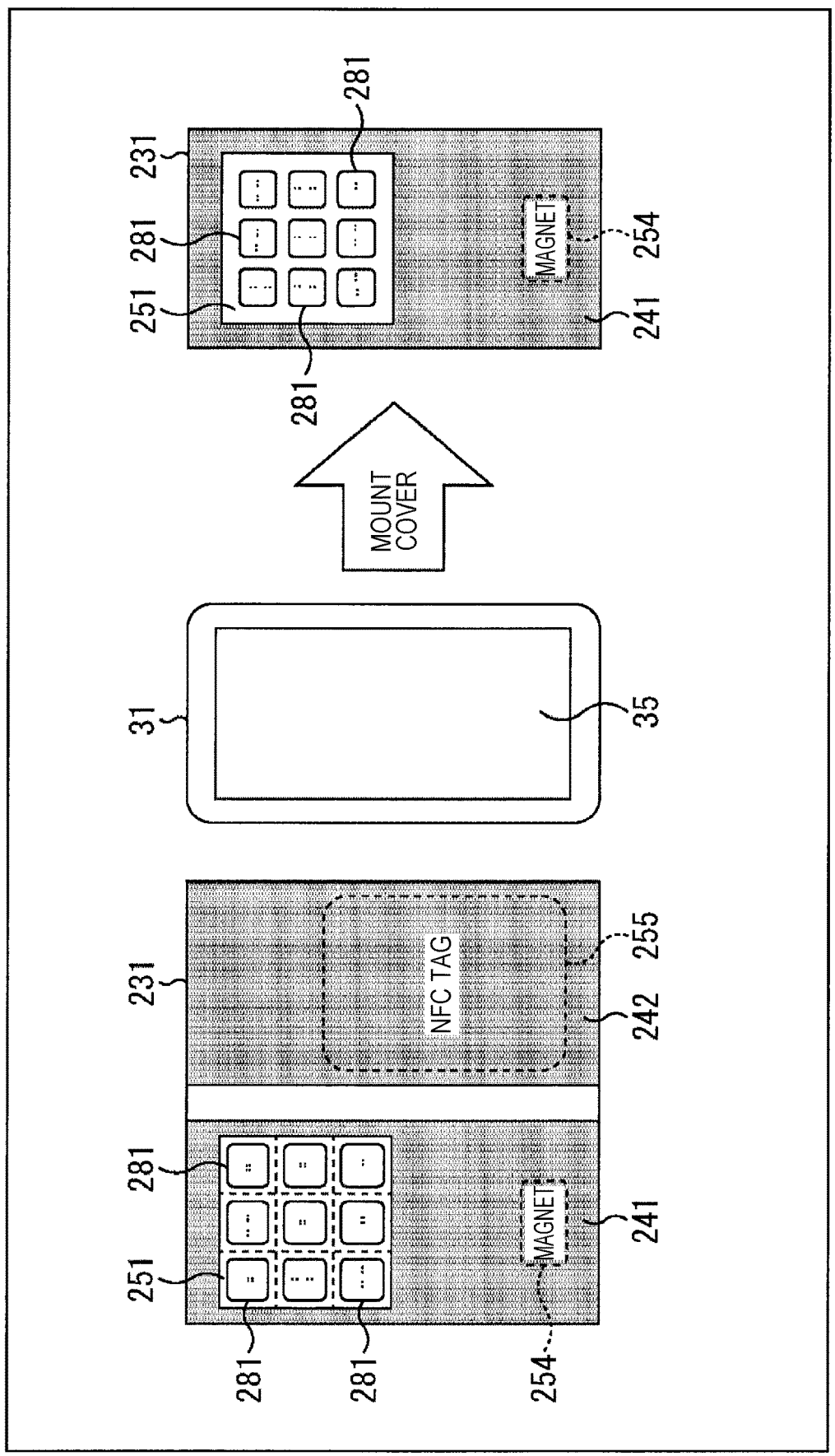
FIG. 43 is a diagram illustrating another example of a seal pasted to a small window of the smartphone cover.

Besides, for example, as illustrated in FIG. 43, a Braille seal 281 may be pasted to each of nine divided areas of the small window 251. The Braille alphabets of the Braille seals 281 may represent the positions of the nine divided areas, or represent the contents of the registration apps. In addition, square recesses or protrusions may be directly formed on the small window 251 including a transmissive material to make the nine divided areas recognizable.

<4.8 Another Example of UI App Disposition Allocated to Small Window>

Figure 44:
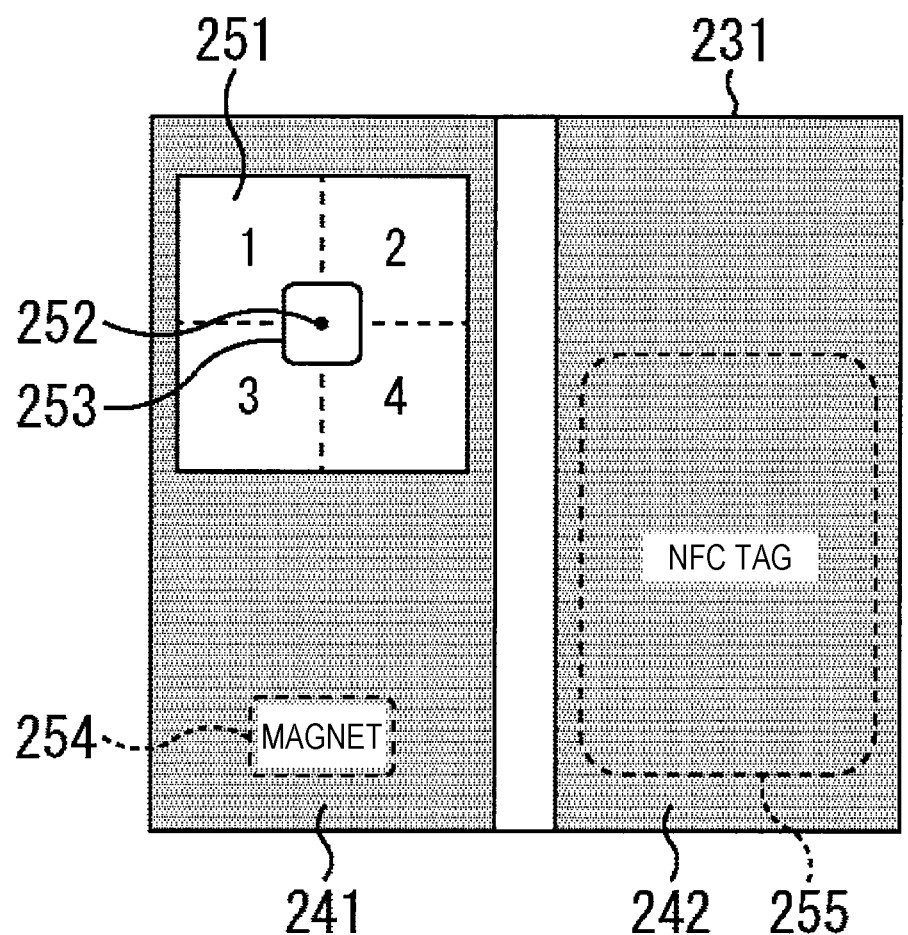
FIG. 44 is a diagram illustrating another display example of the grid mode.

In the smartphone cover 231 illustrated in FIG. 36, the information processing apparatus 1 allocates 3×3 (i.e., nine) UI apps to the open area of the small window 251 on the smartphone cover 231, but, as illustrated in FIG. 44, 2×2 (i.e., four) UI apps may be allocated. Alternatively, any other number of UI apps may be allocated.

In addition, UI disposition information stored in the NFC tag 255 can be different for each of the smartphone covers 231. This makes it possible to change a registration app by mounting the different smartphone cover 231. For example, the smartphone cover 231 for business is switched to the smartphone cover 231 for travel, thereby making it possible to changing apps of different use frequency. The smartphone cover 231 can be identified with NFC tag identification information.

The processing unit 16 of the information processing apparatus 1 may refrain from adopting UI button definition information among UI button coordinate information and the UI button definition information included in UI disposition information acquired from the NFC tag 255 of the smartphone cover 231, but may adopt UI button definition information set by a visually impaired person himself or herself in the information processing apparatus 1.

That is, a visually impaired person himself or herself who is a user of the information processing apparatus 1 may set, for example, what app is allocated to each of nine divided areas in the information processing apparatus 1, and the processing unit 16 may dispose UI buttons in accordance with the setting. In other words, UI button definition information acquired from the NFC tag 255 of the smartphone cover 231 is acquired as default UI button definition information, but in the case where there is UI button definition information set by a user himself or herself, it is preferentially used.

In addition, the processing unit 16 may be capable of controlling the NFC communication unit 272 to transmit UI button definition information set by a user of the information processing apparatus 1 to the NFC tag 255 through near field communication, and overwriting the UI button definition information stored in the NFC tag 255.

<5. Hardware Configuration Example of Information Processing Apparatus>

Next, the hardware configuration of an information processing apparatus 1 will be described with reference to FIG. 45.

Figure 45:
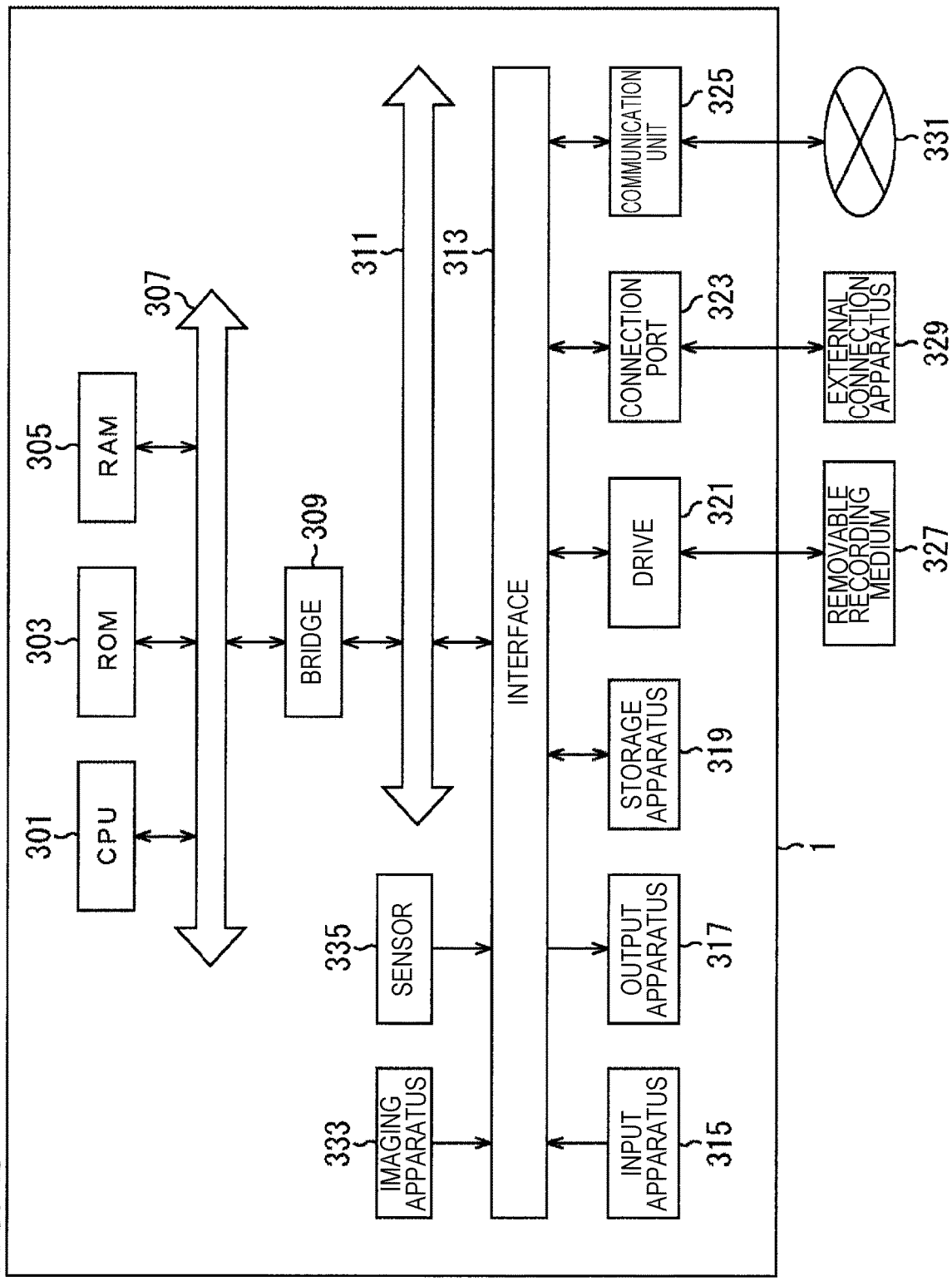
FIG. 45 is a block diagram illustrating a hardware configuration example of the information processing apparatus.

FIG. 45 is a block diagram illustrating a hardware configuration example of the information processing apparatus 1.

The information processing apparatus 1 includes a central processing unit (CPU) 301, read only memory (ROM) 303, and random access memory (RAM) 305. In addition, the information processing apparatus 1 may include a host bus 307, a bridge 309, an external bus 311, an interface 313, an input apparatus 315, an output apparatus 317, a storage apparatus 319, a drive 321, a connection port 323, and a communication apparatus 325. Moreover, the information processing apparatus 1 may include an imaging apparatus 333, and a sensor 335, as necessary. The information processing apparatus 1 may include a processing circuit such as a digital signal processor (DSP), an application-specific integrated circuit (ASIC), or a field-programmable gate array (FPGA), alternatively or in addition to the CPU 301.

The CPU 301 serves as an arithmetic processing apparatus and a control apparatus, and controls the overall operation or a part of the operation of the information processing apparatus 1 according to various programs recorded in the ROM 303, the RAM 305, the storage apparatus 319, or a removable recording medium 327. The ROM 303 stores programs, operation parameters, and the like used by the CPU 301. The RAM 305 transiently stores programs used when the CPU 301 is executed, and various parameters that change as appropriate when executing such programs. The CPU 301, the ROM 303, and the RAM 305 are connected with each other via the host bus 307 configured from an internal bus such as a CPU bus or the like. Further, the host bus 307 is connected to the external bus 311 such as a Peripheral Component Interconnect/Interface (PCI) bus via the bridge 309.

The input apparatus 315 is an apparatus operated by a user such as a mouse, a keyboard, a touch panel, a button, a switch, and a lever. The input apparatus 315 may be a remote control apparatus that uses, for example, infrared radiation and another type of radio wave. Alternatively, the input apparatus 315 may be an external connection apparatus 329 such as a mobile phone that corresponds to an operation of the information processing apparatus 1. The input apparatus 315 includes an input control circuit that generates input signals on the basis of information which is input by a user to output the generated input signals to the CPU 301. A user inputs various types of data to the information processing apparatus 900 and instructs the information processing apparatus 1 to perform a processing operation by operating the input apparatus 315.

The output apparatus 317 includes an apparatus that can report acquired information to a user visually, audibly, or haptically. The output apparatus 317 may be, for example, a display apparatus such as a liquid crystal display (LCD) or an organic electro-luminescence (organic EL), an audio output apparatus such as a speaker or a headphone, or a vibrator. The output apparatus 317 outputs a result obtained through a process performed by the information processing apparatus 1, in the form of video such as text and an image, sounds such as voice and audio sounds, or vibration.

The storage apparatus 319 is an apparatus for data storage that is an example of a storage unit of the information processing apparatus 1. The storage apparatus 319 includes, for example, a magnetic storage device such as a hard disk drive (HDD), a semiconductor storage device, an optical storage device, or a magneto-optical storage device. The storage apparatus 319 stores therein the programs and various data executed by the CPU 301, various data acquired from an outside, and the like.

The drive 321 is a reader/writer for the removable recording medium 327 such as a magnetic disk, an optical disc, a magneto-optical disk, and a semiconductor memory, and built in or externally attached to the information processing apparatus 1. The drive 321 reads out information recorded on the mounted removable recording medium 327, and outputs the information to the RAM 305. Further, the drive 321 writes the record into the mounted removable recording medium 327.

The connection port 323 is a port used to connect devices to the information processing apparatus 1. The connection port 323 may include a Universal Serial Bus (USB) port, an IEEE1394 port, and a Small Computer System Interface (SCSI) port. The connection port 323 may further include an RS-232C port, an optical audio terminal, a High-Definition Multimedia Interface (HDMI) (registered trademark) port, and so on. The connection of the external connection apparatus 329 to the connection port 323 makes it possible to exchange various data between the information processing apparatus 1 and the external connection apparatus 329.

The communication apparatus 325 is a communication interface including, for example, a communication apparatus for connection to a communication network 331. The communication apparatus 325 may be, for example, a communication card for a local area network (LAN), Bluetooth (registered trademark), Wi-Fi, or a wireless USB (WUSB). The communication apparatus 325 may also be, for example, a router for optical communication, a router for asymmetric digital subscriber line (ADSL), or a modem for various types of communication. For example, the communication apparatus 325 transmits and receives signals in the Internet or transits signals to and receives signals from another communication apparatus by using a predetermined protocol such as TCP/IP. The communication network 331 to which the communication apparatus 325 connects is a network established through wired or wireless connection. The communication network 331 may include, for example, the Internet, a home LAN, infrared communication, radio communication, or satellite communication.

The imaging apparatus 333 is an apparatus that captures an image of a real space by using an image sensor such as a charge coupled device (CCD) and a complementary metal oxide semiconductor (CMOS) sensor, and various members such as a lens for controlling image formation of a subject image onto the image sensor, and generates the captured image. The imaging apparatus 333 may capture a still image or a moving image.

The sensor 335 is various sensors such as an acceleration sensor, an angular velocity sensor, a geomagnetic sensor, an illuminance sensor, a temperature sensor, a barometric sensor, and a sound sensor (microphone). The sensor 335 acquires information regarding a state of the information processing apparatus 1 such as a posture of a housing of the information processing apparatus 1, and information regarding an environment surrounding the information processing apparatus 1 such as luminous intensity and noise around the information processing apparatus 1. The sensor 335 may include a GPS receiver that receives global positioning system (GPS) signals to measure latitude, longitude, and altitude of the apparatus.

The example of the hardware configuration of the information processing apparatus 1 has been described. Each of the structural elements described above may be configured by using a general purpose component or may be configured by hardware specialized for the function of each of the structural elements. The configuration may be changed as necessary in accordance with the state of the art at the time of working of the present disclosure.

An embodiment of the present disclosure may include, for example, an information processing apparatus, a system (visually impaired person walking support system), an information processing method to be executed in the information processing apparatus or the system, a program for causing the information processing apparatus to function, and a non-transitory tangible medium having the program recorded thereon, as described above.

Note that the steps described herein in the flow charts may be naturally performed chronologically in the described order, but do not necessarily have to be processed chronologically. The steps described herein in the flow charts may be executed in parallel, or at necessary timing like when invoked or the like.

Further, in the present disclosure, a system has the meaning of a set of a plurality of configured elements (such as an apparatus or a module (part)), and does not take into account whether or not all the configured elements are in the same casing. Therefore, the system may be either a plurality of apparatuses, stored in separate casings and connected through a network, or a plurality of modules within a single casing.

An embodiment of the present technology is not limited to the embodiments described above, and various changes and modifications may be made without departing from the scope of the technology.

For example, it is possible to employ a combination of all or part of the above-described multiple embodiments.

For example, the present technology can adopt a configuration of cloud computing which processes by allocating and connecting one function by a plurality of apparatuses through a network.

Further, each step described by the above-mentioned flow charts can be executed by one apparatus or by allocating a plurality of apparatuses.

In addition, in the case where a plurality of processes are included in one step, the plurality of processes included in this one step can be executed by one apparatus or by sharing a plurality of apparatuses.

Note that the effects described in the present specification are not limiting but are merely examples, and there may be additional effects.

Additionally, the present technology may also be configured as below.

(1)

An information processing apparatus including:

a direction decision unit configured to decide a direction in which a person who behaves without a sense of sight walks; and a first guide information generation unit configured to generate guide information for the person who behaves without the sense of sight to walk in the decided direction.

(2)

The information processing apparatus according to (1), in which the direction decision unit decides the direction in which the person who behaves without the sense of sight walks on the basis of a matching result obtained by matching a reference image stored in advance with a still image captured at a current time point.

(3)

The information processing apparatus according to (2), in which the direction decision unit extracts a feature point corresponding to a feature point of the reference image from the still image, and decides the direction in which the person who behaves without the sense of sight walks on the basis of a matching result obtained by matching the corresponding feature points.

(4)

The information processing apparatus according to (3), in which the direction decision unit changes an area of the still image in which the corresponding feature points are matched in accordance with a color of a traffic light shown in the still image.

(5)

The information processing apparatus according to any of (2) to (4), in which the direction decision unit binarizes the still image, and then matches the reference image with the still image.

(6)

The information processing apparatus according to any of (2) to (5), in which the direction decision unit calculates an azimuth in the still image and an azimuth of an imaging unit when the imaging unit captures the still image to estimate a direction in which the person who behaves without the sense of sight faces, and decide the direction in which the person who behaves without the sense of sight walks.

(7)

The information processing apparatus according to any of (2) to (6), in which the direction decision unit integrates pieces of direction information estimated in a plurality of the respective still images, estimates a direction in which the person who behaves without the sense of sight faces, and decides the direction in which the person who behaves without the sense of sight walks.

(8)

The information processing apparatus according to (7), in which the direction decision unit weights and averages directions estimated in the plurality of respective still images, estimates the direction in which the person who behaves without the sense of sight faces, and decides the direction in which the person who behaves without the sense of sight walks.

(9)

The information processing apparatus according to any of (2) to (8), further including:

a registration unit configured to register the reference image.

(10)

The information processing apparatus according to any of (1) to (9), in which the first guide information generation unit includes a calculation unit that calculates an amount of deviation from the decided direction on the basis of pedestrian dead reckoning, and the calculation unit calculates an amount of deviation from the decided direction in a horizontal direction, and a body orientation deviation with respect to the decided direction.

(11)

The information processing apparatus according to any of (1) to (10), in which the direction decision unit decides, in front of a crosswalk, the direction in which the person who behaves without the sense of sight walks, and while the person who behaves without the sense of sight is walking on a crosswalk, the first guide information generation unit generates the guide information for the person who behaves without the sense of sight to walk in the decided direction.

(12)

The information processing apparatus according to any of (1) to (11), further including:

an output unit configured to output the generated guide information, in which the guide information is a voice message or electronic sound.

(13)

The information processing apparatus according to any of (1) to (12), further including:

a second guide information generation unit configured to generate guide information regarding a checkpoint where the person who behaves without the sense of sight walks.

(14)

The information processing apparatus according to (13), in which the second guide information generation unit generates a voice stored in association with a checkpoint near a current location as guide information regarding the checkpoint.

(15)

The information processing apparatus according to any of (1) to (14), further including:

a third guide information generation unit configured to recognize a positional relationship between the person who behaves without the sense of sight and an unmanned aircraft that tracks the person, and generate guide information for guiding the person who behaves without the sense of sight to a correct position.

(16)

The information processing apparatus according to any of (1) to (14), further including:

a third guide information generation unit configured to compare an image captured by an unmanned aircraft with a current location image obtained by imaging a current location of the person who behaves without the sense of sight, and generate guide information for guiding the person who behaves without the sense of sight to a correct position.

(17)

The information processing apparatus according to any of (1) to (16), in which the information processing apparatus is a smartphone, and the information processing apparatus further includes a detection unit configured to detect whether or not a smartphone cover is closed, and a display control unit configured to switch display of a display in a case where the smartphone cover is closed.

(18)

The information processing apparatus according to (17), further including:

a near field communication unit configured to perform near field communication with the smartphone cover, in which the display control unit switches the display of the display on the basis of information acquired through the near field communication in the case where the smartphone cover is closed.

(19)

An information processing method including, by an information processing apparatus:

a step of deciding a direction in which a person who behaves without a sense of sight walks; and a step of generating guide information for the person who behaves without the sense of sight to walk in the decided direction.

(20)

A program for causing a computer to function as:

a direction decision unit configured to decide a direction in which a person who behaves without a sense of sight walks; and a guide information generation unit configured to generate guide information for the person who behaves without the sense of sight to walk in the decided direction.

REFERENCE SIGNS LIST 1 information processing apparatus
11 camera
12 direction sensor
13 GPS sensor
14 operation unit
15 storage unit
16 processing unit
17 output unit
51 Ref image registration unit
61 direction decision unit
62 guide information generation unit
63 PDR calculation unit
121 microphone
141 voice registration unit
142 checkpoint notification unit
191 short-range wireless communication unit
211 Ref image registration unit
212 guide information generation unit
231 smartphone cover
241 front face cover
254 magnet
255 NFC tag
271 magnetic force detection unit
272 NFC communication unit
301 CPU
303 ROM
305 RAM
315 input apparatus
317 output apparatus
319 storage apparatus
333 imaging apparatus
335 sensor

The invention claimed is:

1. An information processing apparatus, comprising:
an image sensor configured to capture a current image at a specific time duration after a start of walk of a person; and
a central processing unit (CPU) configured to:
compare the current image and a reference image, wherein a time of capture of the reference image corresponds to the specific time duration;
determine a first direction of the walk of the person based on the comparison of the current image and the reference image; and
generate guide information for the person based on the determined first direction, wherein the guide information indicates the person to walk in the first direction.

2. The information processing apparatus according to claim 1, wherein
the reference image is stored in advance, and
the image sensor is further configured to capture the current image in real time.

3. The information processing apparatus according to claim 2, wherein the CPU is further configured to:
extract a first feature point from the current image, wherein the first feature point corresponds to a second feature point of the reference image;

compare the first feature point and the second feature point; and determine the first direction based on the comparison of the first feature point and the second feature point.

4. The information processing apparatus according to claim 3, wherein the CPU is further configured to change an area of the current image to match the first feature point with the second feature point, the area corresponds to the first feature point, and the first feature point corresponds to a color of a traffic light in the current image.

5. The information processing apparatus according to claim 2, wherein the CPU is further configured to:

binarize the current image; and compare the reference image with the binarized current image.

6. The information processing apparatus according to claim 2, wherein the CPU is further configured to:

calculate an azimuth in the current image; and calculate an azimuth of the image sensor based on the capture of the current image;

determine a second direction in which the person faces, wherein the second direction is determined based on the azimuth of the current image and the azimuth of the image sensor; and determine the first direction based on the second direction.

7. The information processing apparatus according to claim 2, wherein the image sensor is further configured to capture a plurality of first images, the plurality of first images includes the current image, and the CPU is further configured to:

estimate pieces of direction information in the plurality of first images;

integrate the pieces of direction information;

determine a second direction in which the person faces, wherein the second direction is determined based on the integration; and determine the first direction based on the second direction.

8. The information processing apparatus according to claim 2, wherein the CPU is further configured to register the reference image.

9. The information processing apparatus according to claim 1, wherein the CPU is further configured to:

calculate an amount of deviation from the first direction, wherein the calculation is based on pedestrian dead reckoning, and the amount of deviation is in a horizontal direction;

calculate a body orientation deviation, wherein the body orientation deviation is an angular deviation of the person with respect to the first direction; and generate the guide information for the person based on the amount of deviation and the body orientation deviation.

10. The information processing apparatus according to claim 1, wherein the CPU is further configured to:

determine the first direction based on the person who is in front of a crosswalk; and generate the guide information based on the walk of the person on the crosswalk.

11. The information processing apparatus according to claim 1, further comprising:

an output interface configured to output the generated guide information, wherein the guide information is a voice message or electronic sound.

12. The information processing apparatus according to claim 1, wherein the guide information is associated with a checkpoint, and the checkpoint is on a route of the walk of the person.

13. The information processing apparatus according to claim 12, wherein the guide information is a voice message.

14. The information processing apparatus according to claim 1, wherein the CPU is further configured to:

determine a positional relationship between the person and an unmanned aircraft that tracks the person; and generate the guide information based on the positional relationship.

15. The information processing apparatus according to claim 1, wherein the CPU is further configured to:

compare an aerial image captured by an unmanned aircraft with the current image; and generate the guide information based on the comparison of the aerial image and the current image.

16. The information processing apparatus according to claim 1, further comprising a display screen, wherein the information processing apparatus is a smartphone, and the CPU is further configured to:

detect that a smartphone cover is in a closed state with respect to the smartphone; and control the display screen based on the closed state of the smartphone cover.

17. The information processing apparatus according to claim 16, further comprising:

a near field communication unit configured to:

establish a near field communication between the smartphone cover and the smartphone; and acquire information from the smartphone cover via the near field communication, wherein, in the closed state of the smartphone cover, the CPU is further configured to control the display screen based on the acquired information.

18. An information processing method, comprising, in an information processing apparatus:

capturing a current image at a specific time duration after a start of walk of a person;

comparing the current image and a reference image, wherein a time of capture of the reference image corresponds to the specific time duration;

determining a direction of the walk of the person based on the comparison of the current image and the reference image; and generating guide information for the person based on the determined direction, wherein the guide information indicates the person to walk in the determined direction.

19. A non-transitory computer-readable medium having stored thereon, computer executable-instructions that, when executed by a processor, cause the processor to execute operations, the operations comprising:

capturing a current image at a specific time duration after a start of walk of a person;

comparing the current image and a reference image, wherein a time of capture of the reference image corresponds to the specific time duration;

determining a direction of the walk of the person based on the comparison of the current image and the reference image; and generating guide information for the person based on the determined direction, wherein the guide information indicates the person to walk in the determined direction.

\* \* \* \* \*